(12) United States Patent
Kondo

(10) Patent No.: US 9,952,129 B2
(45) Date of Patent: Apr. 24, 2018

(54) FAILURE DETECTION SENSOR, FAILURE DETECTION SYSTEM, AND STRUCTURE

(71) Applicant: HIEI KENSETSU CORPORATION, Sapporo-shi, Hokkaido (JP)

(72) Inventor: Tsukasa Kondo, Hokkaido (JP)

(73) Assignee: Hiei Kensetsu Corporation, Hokkaido (JP)

( * ) Notice: Subject to any disclaimer, the term of this patent is extended or adjusted under 35 U.S.C. 154(b) by 0 days.

(21) Appl. No.: 14/784,181

(22) PCT Filed: Jan. 27, 2015

(86) PCT No.: PCT/JP2015/052099
§ 371 (c)(1),
(2) Date: Oct. 13, 2015

(87) PCT Pub. No.: WO2015/115391
PCT Pub. Date: Aug. 6, 2015

(65) Prior Publication Data
US 2016/0370268 A1 Dec. 22, 2016

(30) Foreign Application Priority Data
Jan. 31, 2014 (JP) ................................ 2014-016414

(51) Int. Cl.
*F16B 31/02* (2006.01)
*G01N 3/08* (2006.01)
(Continued)

(52) U.S. Cl.
CPC ............ *G01N 3/08* (2013.01); *F16B 5/0642* (2013.01); *F16B 31/02* (2013.01); *F16B 31/021* (2013.01);
(Continued)

(58) Field of Classification Search
None
See application file for complete search history.

(56) References Cited

U.S. PATENT DOCUMENTS 4,481,902 A 11/1984 Meyer
5,426,973 A * 6/1995 Hartt ...................... G01N 17/00
106/640
(Continued)

FOREIGN PATENT DOCUMENTS

JP 51-081682 7/1976
JP 51-044834 10/1976
(Continued)

OTHER PUBLICATIONS

International Search Report issued in connection with International Patent Application No. PCT/JP2015/052099, dated May 19, 2015. (2 pages).
(Continued)

*Primary Examiner* — Andre Allen
(74) *Attorney, Agent, or Firm* — K&L Gates LLP

(57) ABSTRACT

Provided is a failure detection sensor which, when attached to structural members of various structures such as buildings can easily detect the risk of the failure of the structural members, and thus the structure, before such failure occurs and has a simple structure, which leads to realization at a low price.
The failure detection sensor comprises: the first member 10 and the second member 20 provided in parallel with the first member 10 such that one end of the second member 20 is fixed to or restricted by the first member 10 and the other end of the second member 20 is not fixed to or restricted by the first member 10, having fracturing characteristics such that the second member 20 fractures during elastic deformation or plastic deformation of the first member 10. The failure detection sensor may have a compression coil spring 40
(Continued)

which applies a tensile force to the other end of the second member 20 on the opposite side of the one end. The first member 10 and the second member 20 are constituted of, for example, a round rod or a square rod and the first member 10 is constituted of, for example, a hollow rod. The second member 20 has a notch 24 which is a stress concentration site between the one end and the other end. The second member 20 is made of brittle materials.

5 Claims, 46 Drawing Sheets

(51) Int. Cl.
    *H01H 35/00* (2006.01)
    *F16B 5/06* (2006.01)
(52) U.S. Cl.
    CPC ......... *F16B 31/025* (2013.01); *H01H 35/006* (2013.01)

(56) References Cited

U.S. PATENT DOCUMENTS

| | | | | |
|---|---|---|---|---|
| 5,728,943 A * | 3/1998 | Colter, Jr. | ............ | G01N 17/043 324/700 |
| 6,012,337 A * | 1/2000 | Hodge | ............ | G01B 11/16 324/700 |
| 6,181,841 B1 * | 1/2001 | Hodge | ............ | G01B 11/16 385/12 |
| 6,487,914 B1 * | 12/2002 | Hodge | ............ | G01B 11/16 73/800 |
| 6,647,161 B1 * | 11/2003 | Hodge | ............ | G01B 11/16 385/12 |
| 7,908,928 B2 * | 3/2011 | Vik | ............ | G01M 5/0033 73/806 |
| 2006/0260402 A1 * | 11/2006 | Kim | ............ | G01H 9/004 73/587 |
| 2016/0237804 A1 * | 8/2016 | Papadimitriou | .... | E21B 47/0006 |

FOREIGN PATENT DOCUMENTS

| | | |
|---|---|---|
| JP | 11-118637 | 4/1999 |
| JP | 2004-183817 | 7/2004 |
| JP | 2011-164080 | 8/2011 |
| JP | 2012-057709 | 3/2012 |

OTHER PUBLICATIONS

Office Action issued in connection with Japanese Patent Application No. 2014-020155, dated Apr. 8, 2014. (7 pages).

* cited by examiner

SHEAR LOAD

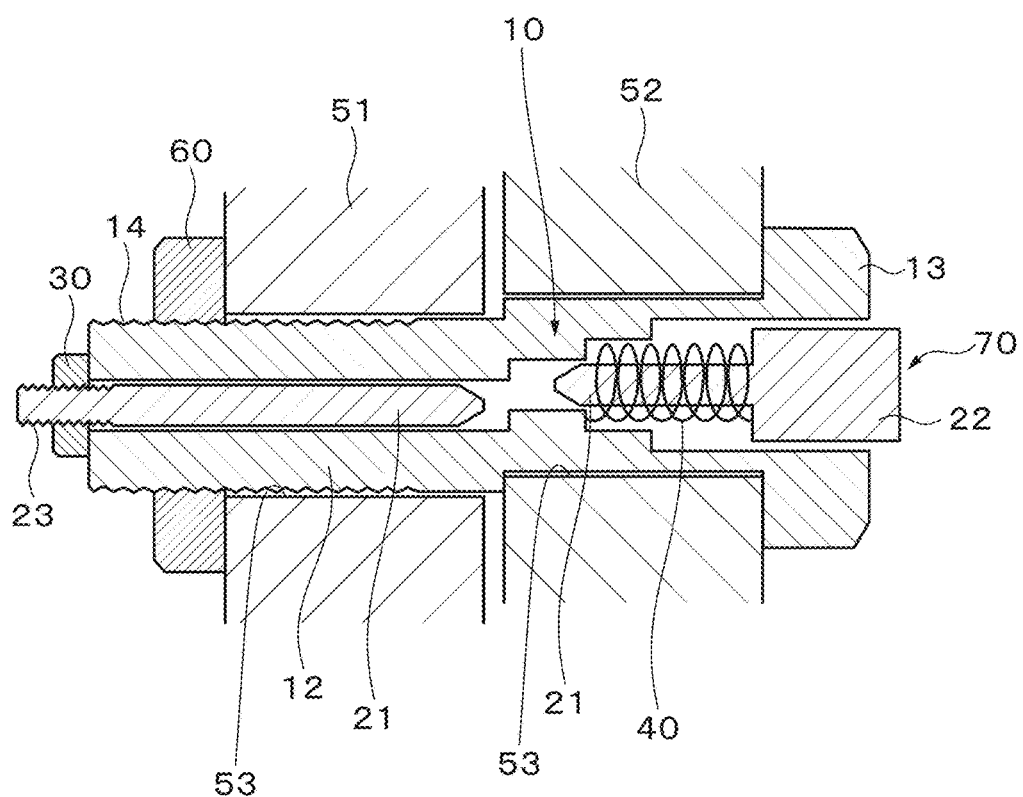

TORSIONAL MOMENT

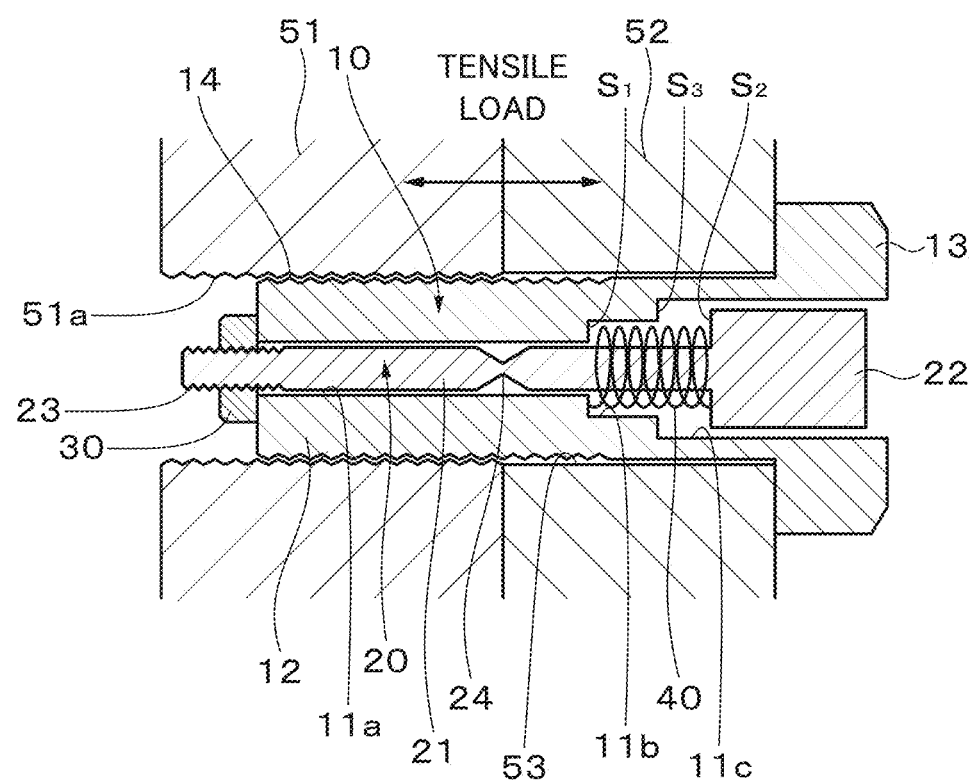

FIRST MEMBER    COMPRESSION COIL SPRING    SECOND MEMBER

FAILURE DETECTION SENSOR
FOR DETECTING TENSILE FRACTURE

TENSILE FRACTURE EXPERIMENT DEVICE

TENSILE FRACTURE EXPERIMENT DEVICE

Fig. 50
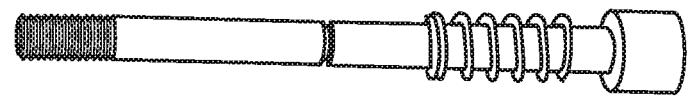
SECOND MEMBER
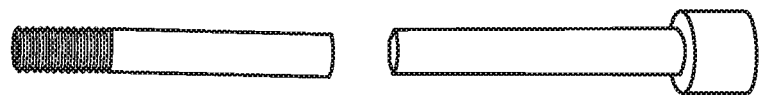
SECOND MEMBER (AFTER FRACTURED)
Fig. 51
FAILURE DETECTION SENSOR
FOR DETECTING BEND FRACTURE

FIRST MEMBER AND MOVABLE PART

TEST PIECE FOR MEASURING DISPLACEMENT
USING POTENTIOMETER

FAILURE DETECTION SENSOR, FAILURE DETECTION SYSTEM, AND STRUCTURE

CROSS REFERENCES TO RELATED APPLICATIONS

The present application is a national stage of International Application No. PCT/JP2015/052099 filed on Jan. 27, 2015 and claims priority to Japanese Patent Application No. 2014-016414 filed on Jan. 31, 2014, the disclosure of which is incorporated herein by reference.

BACKGROUND

This invention relates to a failure detection sensor, a failure detection system, and a structure, which are suitably applied, for example, to detect the risk of the failure of joints of various structures such as buildings.

For the purpose of joint (wide sense joint including connection and fastening) of structural members of various structures such as buildings, bridges, and tunnels, various joint technologies such as welding, rivets, bolts and nuts have been used. Since the failure of the joints of the structural members has a close relation to damage of the structure from the view of safety of the structure, it is necessary to examine damage of joints and a periodic examination must be made. Conventional general examination methods for this purpose are mainly a hammering test and visual inspection. However, especially the hammering test requires intuition and skill of inspectors, and therefore the inspectors are limited. Furthermore, generally, the joints of the structural members frequently locate at a high place or a place which is difficult to be seen by persons, so it is very difficult to carry out the hammering test and visual inspection. Also, examination work using a high place working car is an inefficient work which needs time and energy and the risk is high. Therefore, demanded is a technology which detects and notifies the risk of the failure of the joints in a short time and completely automatically around the clock.

For this purpose, known is a watching method which detects immediately when fracture of bolts fixing an object occurs or an object fixed falls off (see patent literature 1). According to the watching method, the state of the bolts fixing the object or the object attached to the structure is always watched contactless, and when fracture of the bolts occurs or the object attached falls off, it is immediately detected and an alarm is caused. Furthermore, known is an axial force control bolt which can fasten an object to be fastened with a predetermined axial force or an axial force reaching a plastic region and easily know whether the bolt is of before plastic deformation or after plastic deformation (see patent literature 2). The axial force control bolt comprises an axial part and a screw part and can control the axial force applied in the axial direction. Axial force detecting materials which fracture when the strain in the axial direction of the bolt exceeds a predetermined value are applied to the outer surface of at least the axial part of the bolt. The axial force detecting materials are applied in the state where the tension in the axial direction is applied to the bolt in advance. In addition, known is a high strength bolt having the capability of preventing scattering, provided with materials in the inside of the high strength bolt in the axial direction which can be elongated larger than the materials of the high strength bolt and have a cross section gradually increasing from the position near the end surface to the end in respective ends (see patent literature 3).

PRIOR ART LITERATURE

Patent Literature

[PATENT LITERATURE 1] Laid-open gazette 2011-164080
[PATENT LITERATURE 2] Laid-open gazette 2012-57709
[PATENT LITERATURE 3] Laid-open gazette 2004-183817

SUMMARY

Subjects to be Solved by Invention

However, the watching method described in patent literature 1 only detects that fracture of the bolt occurs or the object attached to the structure falls off and cannot detect before fracture of the bolt occurs or the object attached to the structure falls off. Furthermore, the axial force control bolt described in patent literature 2 can control only the axial force of the bolt, and therefore can detect only tensile fracture and cannot detect shear fracture, bend fracture, torsional fracture, etc. The high strength bolt described in patent literature 3 is only for preventing an accident caused by scattering and falling off of the bolt from happening.

Therefore, the subject to be solved by the invention is to provide a failure detection sensor which, when attached to structural members of the various structures such as buildings, can easily detect the risk of the failure of the structural members, and thus the structure, before such failure occurs, easily detect a fracture signal, and detect and notify the risk of the fracture in a short time and completely automatically around the clock by using the fracture signal and further has a simple structure, which leads to realization at a low price, and a failure detection system using the failure detection sensor.

Further subject to be solved by the invention is to provide a structure such as buildings, using the failure detection sensor.

Means for Solving the Subjects

To solve the above subject, according to the invention, there is provided a failure detection sensor, comprising:

the first member; and the second member provided in parallel with the first member such that one end of the second member is fixed to or restricted by the first member and the other end of the second member is not fixed to or restricted by the first member, having fracturing characteristics such that the second member fractures during elastic deformation or plastic deformation of the first member.

The failure detection sensor is constructed so that when the first member produces elastic deformation or plastic deformation, a force to fracture the second member is applied to the second member. When the second member fractures during elastic deformation or plastic deformation of the first member is determined as needed. Although the position at which the second member fractures is not particularly limited, it becomes easy to design the failure detection sensor by determining in advance the position at which the second member fractures. Therefore, the second member preferably has a stress concentration site between its one end and the other end. The stress concentration site is typically a notch formed on the outer peripheral surface of the second member. The shape and depth (notch length) of the notch are properly selected, taking into consideration the failure sensitivity etc. of the failure detection sensor. The notch may be formed over the whole circumference of the outer peripheral surface or may be formed on only a part of the circumference, as needed. The stress concentration site is not limited to the notch and may be, for example, cavities formed in the inside of the second member, parts made of materials having elastic modulus different from that of materials constituting the second member, etc. The second member is constructed with materials determined properly depending on materials of structural members of the structure to which the failure detection sensor is attached, materials used for the first member, etc. In order to improve the failure sensitivity of the failure detection sensor, the second member is typically made of brittle materials. The brittle materials are, for example, cast iron, glass, ceramics, plastics, concrete, etc., but they are not limited to these. Thermoplastic resin such as acrylic resin is exemplified as plastics, but not limited to this. For example, when structural members of the structure are made of steel with the possibility of hydrogen embrittlement, the second member is also made of steel with the possibility of hydrogen embrittlement. With this, when the structural members and the failure detection sensor are exposed to atmosphere containing hydrogen by accident etc., the second member becomes brittle due to hydrogen brittlement. As a result, the risk of the failure of the structural members due to hydrogen brittlement can be detected by the failure detection sensor. Furthermore, when structural members of the structure are made of steel with the possibility of low temperature brittleness, the second member is also made of steel with the possibility of low temperature brittleness. With this, when the structural members and the failure detection sensor are cooled to low temperatures for some reason, the second member becomes brittle due to low temperature brittleness. As a result, the risk of the failure of the structural members due to low temperature brittleness can be detected by the failure detection sensor. When the notch is formed on the outer peripheral surface of the second member, the second member may be made of ductile steel with the possibility of notch brittleness etc. Materials of the first member is selected as needed. Generally, the first member is made of materials with ductility higher than that of the second member. For example, the first member is made of steel, wood, plastics, etc., but not limited to these.

In the failure detection sensor suitable for detection of tensile fracture, the first member typically has a press part for pressing the second member in the direction toward the other end from its one end when the first member produces elastic deformation or plastic deformation, and the second member has a part to be pressed which is pressed by the press part. With this, when the first member produces elastic deformation or plastic deformation, its press part presses the part to be pressed of the second member, so that a force which fractures the second member is applied to the second member. In the failure detection sensor suitable for detection of shear fracture, compression fracture, bend fracture and torsion fracture, the press part of the first member and the part to be pressed of the second member are not necessary, but the first member and the second member may have the press part and the part to be pressed, respectively. The failure detection sensor preferably has an energizing mechanism for applying a tensile force to the other end of the second member on the opposite side of the one end. When the second member fractures, the energizing mechanism moves a fractured piece in the direction toward the other end from the one end. The energizing mechanism is, for example, a mechanism using a restoring force of a spring or a mechanism using a magnetic force, but not limited to these. The mechanism using the restoring force of the spring typically is a compression coil spring, a leaf spring or an air spring, but not limited to these. When the mechanism using the magnetic force is used, for example, at least a part of the second member on the side of the other end is made of ferromagnetic substance or permanent magnet and the mechanism using the magnetic force is a permanent magnet or an electromagnet. In this case, an attractive force is applied between the part made of the ferromagnetic substance of the second member and the permanent magnet or the electromagnet.

Typically, the first member is constituted of a hollow rod and the second member is constituted of an inner rod inserted into the hollow part of the hollow rod. The hollow rod and the inner rod may be coaxially provided or may be not coaxially as needed. In the failure detection sensor suitable for detection of tensile fracture, typically, the hollow part of the hollow rod has the first part, the second part and the third part in order in the direction toward the other end from the one end and the inner rod has the fourth part and the fifth part in order in the direction toward the other end from the one end. The fourth part of the inner rod is accommodated in the first part and the second part of the hollow part of the hollow rod, and the fifth part and a part of the fourth part on the side of the fifth part are accommodated in the third part of the hollow part of the hollow rod. In this case, for example, the side surface of a step between the second part and the third part of the hollow part of the hollow rod is used as the press part, and the end surface of the fifth part of the inner rod on the side of the fourth part is used as the part to be pressed. In the failure detection sensor suitable for detection of shear fracture, compression fracture, bend fracture and torsion fracture, the second part of the hollow part of the hollow rod can be omitted. In this case, the fourth part of the inner rod is accommodated in the first part and the third part of the hollow part of the hollow rod, and the fifth part and a part of the fourth part on the side of the fifth part of the inner rod are accommodated in the third part of the hollow part of the hollow rod. The hollow rod and the inner rod are preferably a round rod or a square rod. The shape of a cross section of the square rod is selected as needed, but specifically, for example, triangle, quadrangle (rectangle or square), pentagon, hexagon, octagon, etc. For example, accommodated is in the space between the first part of the hollow part of the hollow rod and the fifth part of the inner rod a compression coil spring through which the fourth part of the inner rod pierces, a leaf spring or an air spring in a compressed state. Alternatively, a spring retainer is provided on one end of the inner rod on the side of the fifth part of the inner rod, a leaf spring or a coil spring is held in the spring retainer and a tensile force is applied to the fifth part of the inner rod. In this case, one end of the leaf spring or the coil spring held in the spring retainer is fixed to the fifth part of the inner rod, and the other end is fixed to the spring retainer. Since in this state the leaf spring or the coil spring is elongated as compared with its natural state, a tensile force is applied to the fifth part of the inner rod.

The failure detection sensor may be for detection of tensile fracture, compression fracture, shear fracture, bend fracture or torsion fracture, or for detection of complex fracture in which two or more of them are combined.

The failure detection sensor can be constructed like a bolt as a whole. In this case, the first member is made to have a shape comprising an axial part on which outer peripheral surface a screw is cut and a head part, and the second member is inserted into the hollow part provided in the first member. The shape of the head part is not limited and selected as needed. The shape of the head part is specifically, for example, hexagonal. The bolt-like failure detection sensor is inserted into a through hole provided in structural members to be joined and attached to the structural members by fitting a nut to a male screw of the axial part protruding from the through hole and fastening it. Alternatively, a female screw is cut on the inner peripheral surface of the through hole of one or both of the structural members to be joined, and the failure detection sensor can be attached to the structural members without using the nut by inserting the axial part of the bolt-like failure detection sensor into the through hole of the structural members to be joined and screwing the male screw of the axial part into the female screw cut on the inner peripheral surface of the through hole. The bolt-like failure detection sensor can be said as a bolt with a failure detection sensor.

The failure detection sensor has, as needed, a fracture and/or displacement detection device for detecting fracture and/or displacement of the second member. Preferably, the failure detection sensor further has a notification and/or display device for notifying and/or displaying outside information of fracture and/or displacement when fracture and/or displacement of the second member is detected by the fracture and/or displacement detection device.

Furthermore, according to the invention, there is provided a failure detection system, comprising:
a failure detection sensor, comprising the first member and the second member provided in parallel with the first member such that one end of the second member is fixed to or restricted by the first member and the other end of the second member is not fixed to or restricted by the first member, having fracturing characteristics such that the second member fractures during elastic deformation or plastic deformation of the first member; and
a notification and/or display device for detecting fracture and/or displacement of the second member of the failure detection sensor and notifying and/or displaying outside information of fracture and/or displacement of the second member which is detected.

Furthermore, according to the invention, there is provided a structure comprising:
one or more failure detection sensors,
at least one of the failure detection sensors being a failure detection sensor, comprising:
the first member; and
the second member provided in parallel with the first member such that one end of the second member is fixed to or restricted by the first member and the other end of the second member is not fixed to or restricted by the first member, having fracturing characteristics such that the second member fractures during elastic deformation or plastic deformation of the first member.

The structure may be basically anything. For example, the structure is the architecture, a bridge, a tunnel, a tower, etc. More specifically, the architecture is a building, an apartment house, a house, a station building, a schoolhouse, a government office building, a stadium, a ballpark, a hospital, a church, a factory, a warehouse, a thermal power plant, a hydroelectric power station, a nuclear power plant, an incinerator, a chemical plant, a blast furnace, etc. The structure may be also various machines (for example, various industrial machines such as a machine tool, a crane, etc.), various vehicles (for example, a crane truck, a bulldozer, a shovel car, etc.), various ships, various airplanes, an advertising tower, a display tower, etc.

In each invention of the failure detection system and the structure, the explanation mentioned above in connection with the invention of the failure detection sensor comes into effect unless it is contrary to its character.

Effect of the Invention

According to the invention, when the failure detection sensor is attached to structural members of a structure, if the first member produces elastic deformation or plastic deformation due to any force applied to the structure, fracture and/or displacement of the second member occurs. Therefore, by detecting the fracture and/or displacement of the second member, it is possible to detect that the first member fractures or excess displacement of the first member occurs. As a result, it is possible to detect the risk of the fracture before the structural members, and thus the structure fractures. Furthermore, for example, if the failure detection sensor is constructed so that when the second member fractures, a fractured piece of the second member springs out from the first member, it is possible to detect easily a fracture signal by detecting spring out of the fractured piece. Therefore, using the fracture signal, it is possible to detect and notify the risk of the fracture completely automatically in a short time around the clock. In addition, since the failure detection sensor can be constructed by the first member and the second member, its structure is simple and it can be realized in a low price. According to the failure detection system using the failure detection sensor, it is possible to notify and/or display outside the risk of the failure before the failure of the structure occurs. Therefore, it is possible to take measures to prevent the failure of the structure. Or, it is possible for persons to evacuate from the structure. As a result, it is possible to prevent human and physical damages from occurring. Furthermore, by selecting an attaching method of the failure detection sensor to the structure, it is possible to detect any one of tensile fracture, shear fracture, compression fracture, bend fracture, torsion fracture, etc.

Additional features and advantages are described herein, and will be apparent from the following Detailed Description and the figures.

BRIEF DESCRIPTION OF THE FIGURES

FIG. 7 A cross sectional view showing a state of the joints and the failure detection sensor when a strong shear load is applied to the joints of the structure shown in FIG. 3.

FIG. 25 A cross sectional view showing a state in which a failure detection sensor according to the tenth embodiment of the invention is attached to junctions of the structure.

FIG. 50 A substitute picture for a drawing showing parts constituting a failure detection sensor for detecting bend fracture made in the example.

FIG. 51 A substitute picture for a drawing showing the failure detection sensor for detecting bend fracture made in the example.

DETAILED DESCRIPTION

Modes for carrying out the invention (hereafter referred as "embodiments") will now be explained below.

1. The First Embodiment

[Failure Detection Sensor]

Figure 1A:
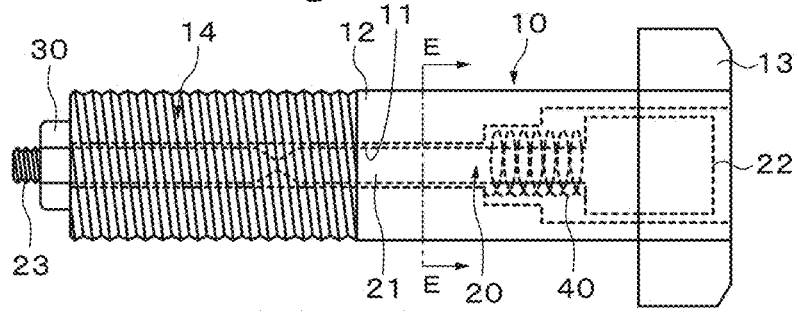
FIG. 1A A front view showing a failure detection sensor according to the first embodiment of the invention.
Figure 1B:
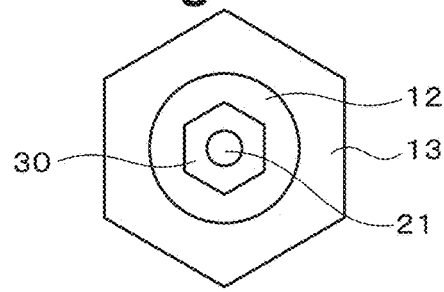
FIG. 1B A left side view showing the failure detection sensor according to the first embodiment of the invention.
Figure 1C:
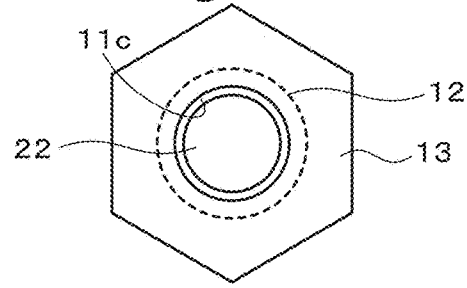
FIG. 1C A right side view showing the failure detection sensor according to the first embodiment of the invention.
Figure 1D:
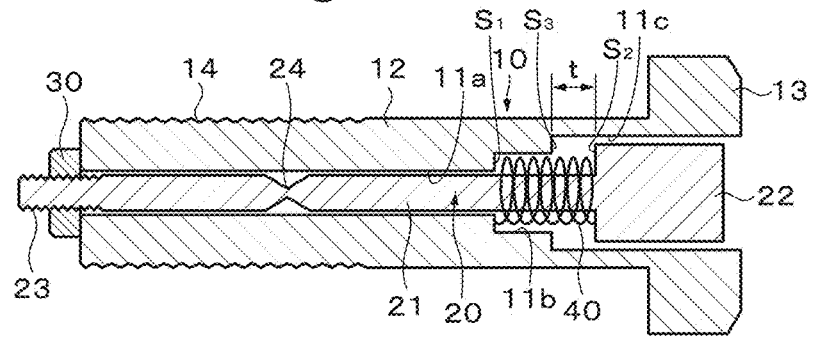
FIG. 1D A longitudinal cross sectional view showing the failure detection sensor according to the first embodiment of the invention.
Figure 1E:
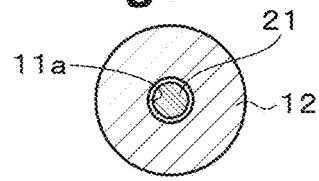
FIG. 1E A cross sectional view showing the failure detection sensor according to the first embodiment of the invention.

FIG. 1A, FIG. 1B, FIG. 1C, FIG. 1D and FIG. 1E show the failure detection sensor according to the first embodiment, where FIG. 1A is a front view, FIG. 1B is a left side view, FIG. 1C is a right side view, FIG. 1D is a longitudinal cross sectional view and FIG. 1E is a cross sectional view along the E-E line of FIG. 1A. The failure detection sensor is especially suitable for detection of tensile fracture.

As shown in FIG. 1A, FIG. 1B, FIG. 1C, FIG. 1D and FIG. 1E, the failure detection sensor comprises a hexagonal bolt-like first member 10 with a hollow part 11 and a circular rod-like second member 20 which is inserted into the hollow part 11 of the first member 10. The second member 20 has fracturing characteristics such that it fractures during elastic deformation or plastic deformation of the first member 10.

Figure 2A:
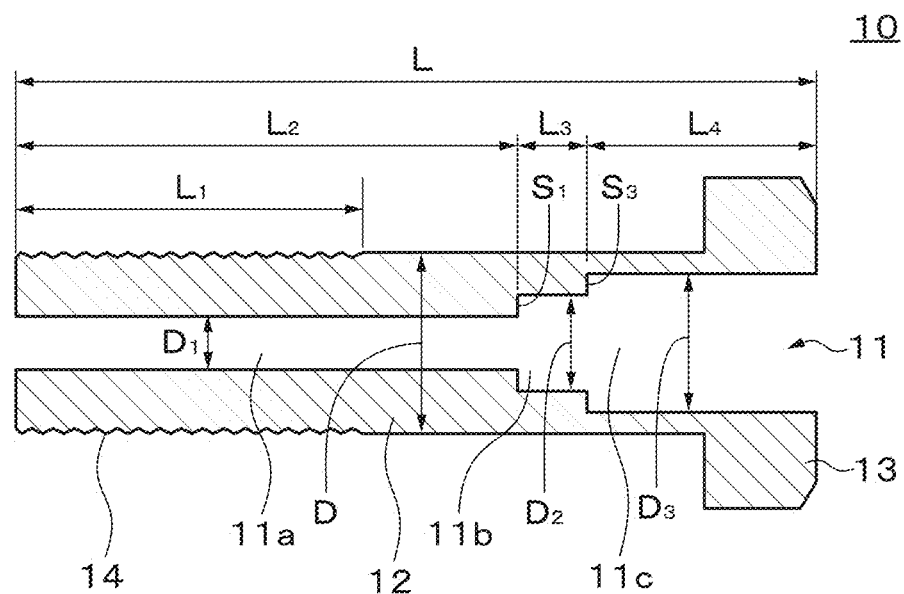
FIG. 2A A longitudinal cross sectional view showing the first member constituting the failure detection sensor according to the first embodiment of the invention.
Figure 2B:
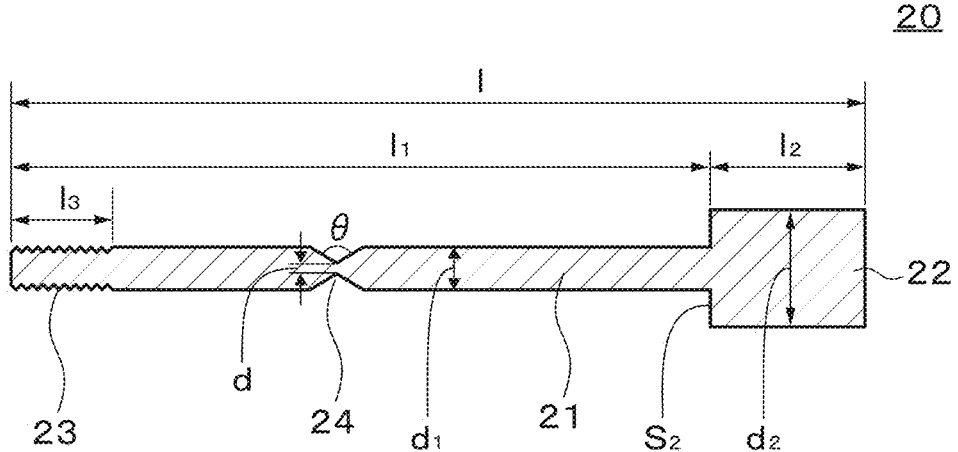
FIG. 2B A longitudinal cross sectional view showing the second member constituting the failure detection sensor according to the first embodiment of the invention.

FIG. 2A shows details of the first member 10, and FIG. 2B shows details of the second member 20. The total length of the first member 10 is denoted as L, and the total length of the second member 20 is denoted as l. Typically, L<l, but not limited to this.

As shown in FIG. 2A, the first member 10 comprises a cylinder-like axial part 12 with a diameter D and a hexagonal cylinder-like head part 13 thicker than the axial part 12. A male screw 14 is cut on the outer peripheral surface of the axial part 12 over a length $L_1$ from its front end. The male screw 14 is used to fit a nut when the failure detection sensor is attached to the structure which is an object to be detected its failure, or to screw into a female screw cut on the inner peripheral surface of a hole formed on the structure. The cross section of the hollow part 11 of the first member 10 has a circular shape centered in the central axis of the first member 10 at any position. The hollow part 11 comprises the first part 11a with a diameter $D_1$ (here, $D_1<D$) and a length $L_2$, the second part 11b with a diameter $D_2$ (here, $D_2>D_1$) and a length $L_3$, and the third part 11c with a diameter $D_3$ (here, $D>D_3>D_2$) and a length $L_4$ in order from the front end of the axial part 12. Here, $L_2+L_3+L_4=L$.

As shown in FIG. 2B, the second member 20 comprises a cylinder-like axial part 21 with a diameter $d_1$ and a length $l_1$ and a cylinder-like head part 22 with a diameter $d_2$ (here, $d_2>d_1$) and a length $l_2$. Here, $l_1+l_2=l$. In addition, $l_1>L_2+L_3$, and $l_2<L_4$. In order to make it possible the axial part 21 of the second member 20 move in the axial direction inside the first part 11a of the hollow part 11 of the first member 10, the diameter $d_1$ of the axial part 21 is selected to be smaller than the diameter $D_1$ of the first part 11a of the hollow part 11 of the first member 10. That is, $d_1<D_1$. In order to decrease play of the axial part 21 inside the first part 11a, typically, for example, the length of the gap between the inner peripheral surface of the first part 11a and the axial part 21, $(D_1-d_1)/2$ is made to be within 5% of the diameter $D_1$ of the first part 11a. That is, typically, it is selected that $(D_1-d_1)/2 \leq 0.05 D_1$ is satisfied. A male screw 23 is cut on the outer peripheral surface of the axial part 21 over a length $l_3$ from its front end. Furthermore, formed on the outer peripheral surface of the axial part 21 over the whole circumference is a V groove-like notch 24 which becomes a stress concentration site. The notch angle of the notch 24 is θ. The diameter $d_2$ of the head part 22 is selected to be smaller than the diameter $D_3$ of the third part 11c of the hollow part 11 of the first member 10. That is, $d_2<D_3$. In order to decrease play of the head part 22 inside the third part 11c, typically, for example, the distance of the gap between the inner peripheral surface of the third part 11c and the head part 22, $(D_3-d_2)/2$ is made to be within 5% of the diameter $D_3$ of the third part 11c. That is, typically, it is selected that $(D_3-d_2)/2 \leq 0.05 D_3$ is satisfied.

As shown in FIG. 1A, FIG. 1B, FIG. 1C, FIG. 1D and FIG. 1E, the axial part 21 of the second member 20 is inserted into the first part 11a and the second part 11b of the hollow part 11 of the first member 10, and its front end protrudes from the end surface of the first member 10. And a nut 30 is fitted to the male screw 23 on the front end of the axial part 21.

The head part 22 and a part of the axial part 21 on the side of the head part 22 of the second member 20 are accommodated in the third part 11c of the hollow part 11 of the first member 10. A compression coil spring 40 is provided on a part of the axial part 21 of the second member 20 on the side of the head part 22 such that it is penetrated by the axial part 21. The compression coil spring 40 is accommodated in the second part 11b and the third part 11c of the hollow part 11 of the first member 10 in a compressed state. The diameter of the compression coil spring 40 is smaller than the diameter $D_2$ of the second part 11b. By a restitutive force applied by the compression coil spring 40 being compressed, one end of the compression coil spring 40 presses a ring-like side surface of a step $S_2$ between the first part 11a and the second part 11b, and the other end of the compression coil spring 40 presses a ring-like end surface $S_2$ of the head 22 of the second member 20 on the side of the axial part 21. Since the end surface $S_2$ of the head part 22 is pressed by the restitutive force of the compression coil spring 40, the axial part 21 of the second member 20 is pulled on the side of the head part 22. With this, the front part of the second member 20 is restricted to the front part of the first member 10. The ring-like side surface of a step $S_3$ between the second part 11b and the third part 11c of the hollow part 11 of the first member 10 constitutes a press part, and the ring-like end surface $S_2$ of the head part 22 of the second member 20 on the side of the axial part 21 constitutes a part to be pressed.

Sizes (L, $L_1$~$L_4$, l, $l_1$~$l_3$, D, $D_1$~$D_3$, d, $d_1$, $d_2$, θ, etc.) of each part of the failure detection sensor are selected depending on the structure to which the failure detection sensor is attached etc. as needed.

Materials of the first member 10 are selected depending on materials of structural members of the structure to be detected its failure by the failure detection sensor etc. as needed, and is, for example, steel, woods, plastics, etc. The second member 20 is made of materials having fracturing characteristics such that it fractures during elastic deformation or plastic deformation of the first member 10, for example, brittle materials such as cast iron, glass, ceramics, plastics, concrete, etc.

[Method of Controlling Failure Sensitivity of the Failure Detection Sensor]

The failure sensitivity (permissible deformation amount of the first member 10) of the failure detection sensor can be controlled by the shape and depth (notch length) of the notch 24 of the second member 20, in other words, a notch angle θ of the tip of the notch 24 and a diameter d of the axial part 21 at the tip of the notch 24, and a distance t between the side surface of a step $S_3$ between the second part 11b and the third part 11c of the hollow part 11 of the first member 10 and the end surface $S_2$ of the head part 22 of the second member 20 on the side of the axial part 21. Here, d can be determined depending on the displacement (elongation) δ from the beginning of the deformation of the second member 20 to its fracture. The distance t is the distance between a position of the side surface of a step $S_3$ of the first member 10 before elastic deformation or plastic deformation of the first member 10 and a position at which the side surface of a step $S_3$ comes in contact with the end surface $S_2$ of the second member 20 by elastic deformation or plastic deformation of the first member 10 and begins to press it, and for determining a position at which deformation of the second member 20 begins. Larger t is, the failure sensitivity of the failure detection sensor becomes low and the permissible deformation amount of the first member 10 becomes large.

[Method of Using the Failure Detection Sensor]

Figure 3:
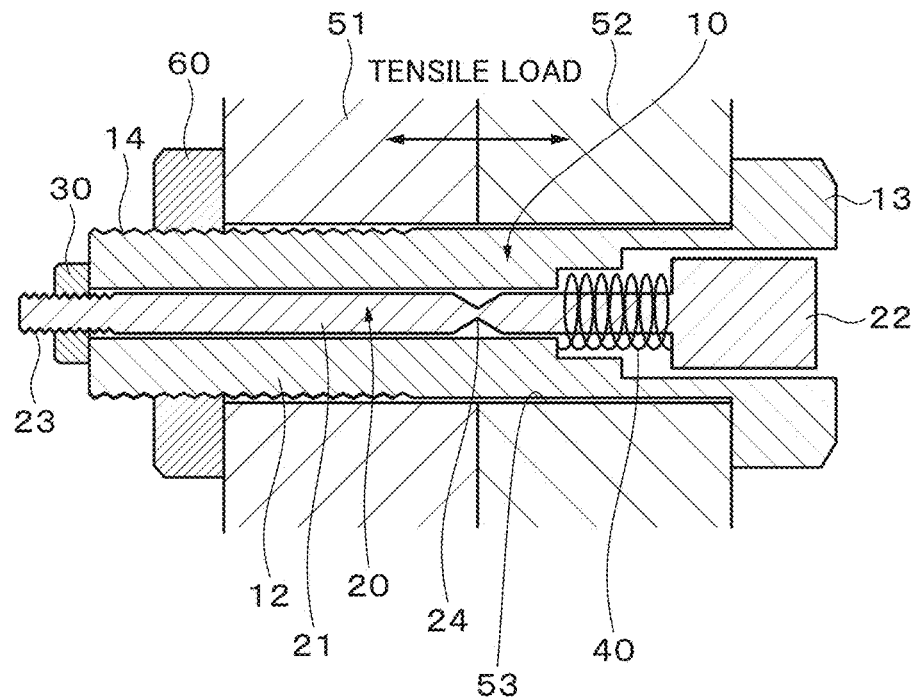
FIG. 3 A cross sectional view showing a state in which the failure detection sensor according to the first embodiment of the invention is attached to joints of the structure.

As shown in FIG. 3, considered is a case where structural members 51, 52 of the structure to be detected failure are the ones joined by bolts and nuts, rivets, welding, etc. Provided is in the structural members 51, 52 a circular through hole 53 with a diameter a little larger than the diameter D of the axial part 12 of the first member 10 of the failure detection sensor. And the axial part 12 is inserted into the through hole 53 until the head part 13 comes in contact with the structural member 52, so that the front part of the axial part 12 is protruded outside the structural member 51. Then, as the same as a general case of fastening by a bolt and a nut, a nut 60 is fitted to the male screw 14 of the axial part 12, and the head part 13 or the nut 60 or both of them is or are rotated by a hexagonal spanner etc. to fasten them. Fastening is carried out with an enough fastening torque so that the failure detection sensor is securely fixed to the structural members 51, 52.

Figure 4:
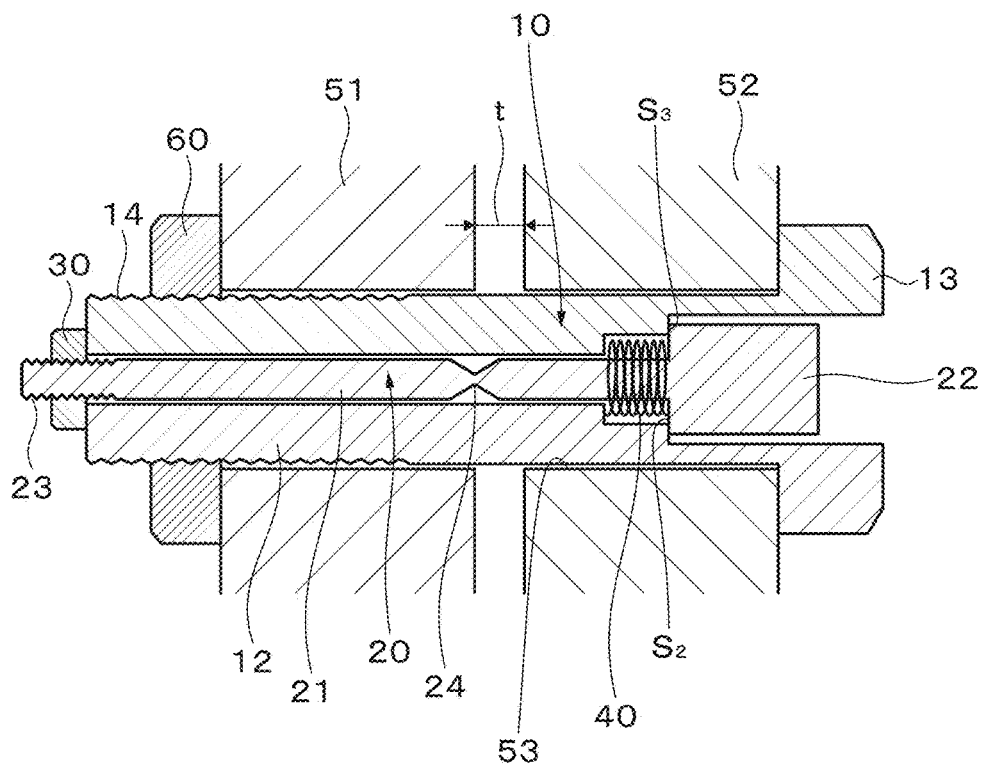
FIG. 4 A cross sectional view showing the joints and the failure detection sensor when a tensile load is applied to the joints of the structure shown in FIG. 3.

First, as shown in FIG. 3, described is a case where the structural members 51, 52 are given a tensile load which separates them. As shown in FIG. 4, when the structural members 51, 52 are given a tensile load, they are separated, so that the axial part 12 of the first member 10 is elongated.

Figure 5:
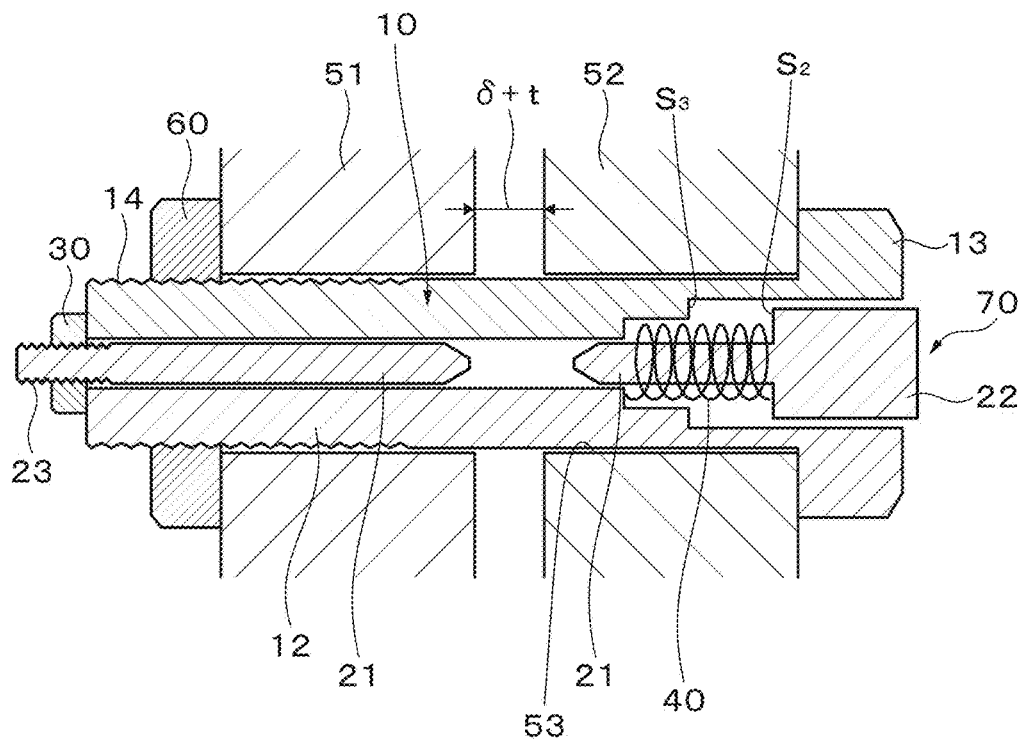
FIG. 5 A cross sectional view showing a state of the joints and the failure detection sensor when a stronger tensile load is applied to the joints of the structure shown in FIG. 3.

When the structural members 51, 52 are given a larger tensile load, elongation of the axial part 12 becomes larger. When elongation of the axial part 12 reaches t, the side surface of a step $S_3$ (the press surface) between the second part 11b and the third part 11c of the hollow part 11 of the first member 10 comes in contact with the end surface $S_2$ (the surface to be pressed) of the head part 22 of the second member 20 on the side of the axial part 21 and begins to press it. As elongation of the axial part 12 becomes further large, the side surface of a step $S_3$ presses the end surface $S_2$ of the second member 20 more intensely. When the side surface of a step $S_3$ of the first member 10 presses the end surface $S_2$ of the second member 20, the second member 20 is given a tensile load in the axial direction and elongated. And, as shown in FIG. 5, when elongation of the axial part 12 becomes δ+t, the second member 20 fractures at the notch 24 which is a stress concentration site, and is divided into two pieces. At this time, a fractured piece 70 which corresponds to a part of the second member 20 on the side of the head part 22 from the fractured part becomes free from mechanical restriction by the first member 10 at one end of the second member 20. As a result, the head part 22 of the fractured piece 70 moves inside the third part 11c of the hollow part 11 of the first member 10 outward by the restitutive force of the compression coil spring 40 and protrudes outward. In other words, a natural length of the compression coil spring 40 is determined so that the head part 22 protrudes outward when the length of the compression coil spring 40 becomes the natural length.

It is easy to recognize visually from the outside, for example, that the head part 22 of the fractured piece 70 protrudes outside the first member 10 as described above. From the result, it is possible to decide that there is the risk of the fracture since the structural members 51, 52 are given the tensile load.

Figure 6:
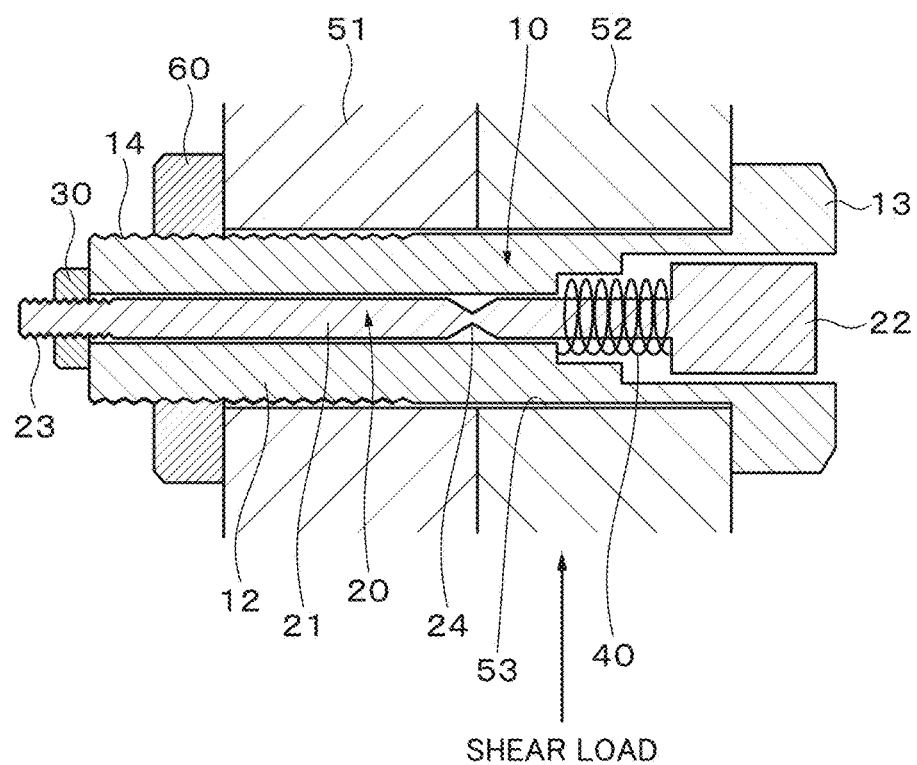
FIG. 6 A cross sectional view showing a state of the joints and the failure detection sensor when a shear load is applied to the junctions of the structure shown in FIG. 3.

The failure detection sensor can also be used to detect shear fracture when the structural members 51, 52 are given a shear load as shown in FIG. 6. In this case, preferably, the notch 24 of the second member 20 is formed so as to locate in the junction of the structural members 51, 52. However, the position of the notch 24 is not limited to this and can be selected as needed. Consider now a case where the structural member 52 is given a shear load such that it slides relative to the structural member 51. As shown in FIG. 7, when the structural members 51, 52 are given the shear load to produce shear deformation, the first member 10 is also given the shear load to produce shear deformation of elastic deformation or plastic deformation. With this, the second member 20 is also given the shear load to produce shear deformation. As a result, the second member 20 fractures at the notch 24, and is divided into two pieces. At this time, the head part 22 of the fractured piece 70 protrudes outward from the first member 10. In this way, by visually recognizing from the outside, for example, that the head part 22 of the second member 20 protrudes outside the first member 10, it is possible to decide that there is the risk of the failure since the structural members 51, 52 are given the shear load.

As described above, according to the first embodiment, when the failure detection sensor is attached to the structural members 51, 52 of the structure, if the first member 10 produces elastic deformation or plastic deformation due to any force given to the structure, the second member 20 fractures or results in displacement. Therefore, by detecting the fracture or displacement, it is possible to detect that the first member 10 fractures or results in excess displacement. As a result, it is possible to easily detect the risk of the failure before failure the structural members 51, 52, and thus the structure occurs. Furthermore, as described later, since it is possible to easily detect a fracture signal by protrusion of the head part 22 of the fractured piece 70 from the first member 10 when the second member 20 fractures, it is possible to detect and notify the risk of the fracture by using the fracture signal in a short time fully automatically around the clock. In addition, since the failure detection sensor can be constructed by the first member 10 and the second member 20, it has a simple structure and can be realized in a low cost.

2. The Second Embodiment

[Failure Detection Sensor]

Figure 8A:
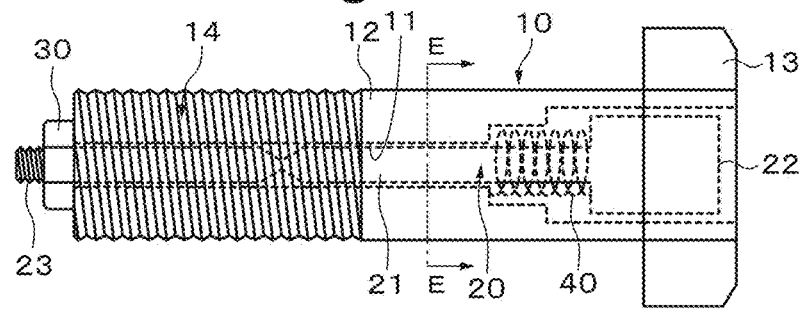
FIG. 8A A front view showing a failure detection sensor according to the second embodiment of the invention.
Figure 8B:
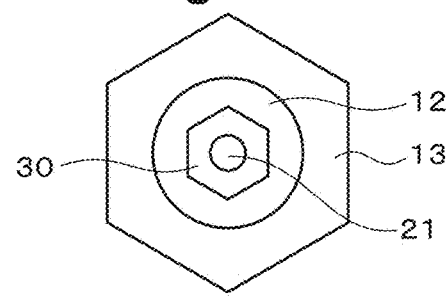
FIG. 8B A left side view showing the failure detection sensor according to the second embodiment of the invention.
Figure 8C:
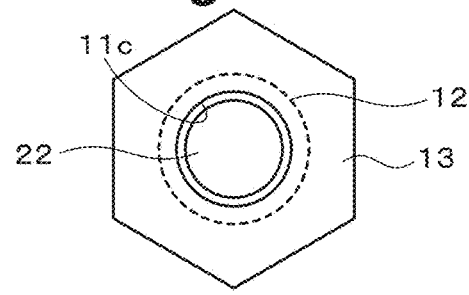
FIG. 8C A right side view showing the failure detection sensor according to the second embodiment of the invention.
Figure 8D:
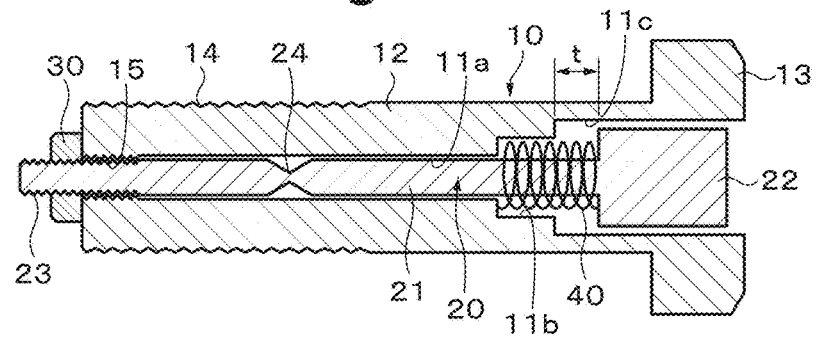
FIG. 8D A longitudinal cross sectional view showing the failure detection sensor according to the second embodiment of the invention.
Figure 8E:
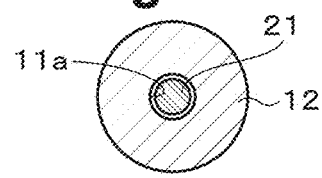
FIG. 8E A cross sectional view showing the failure detection sensor according to the second embodiment of the invention.
Figure 9A:
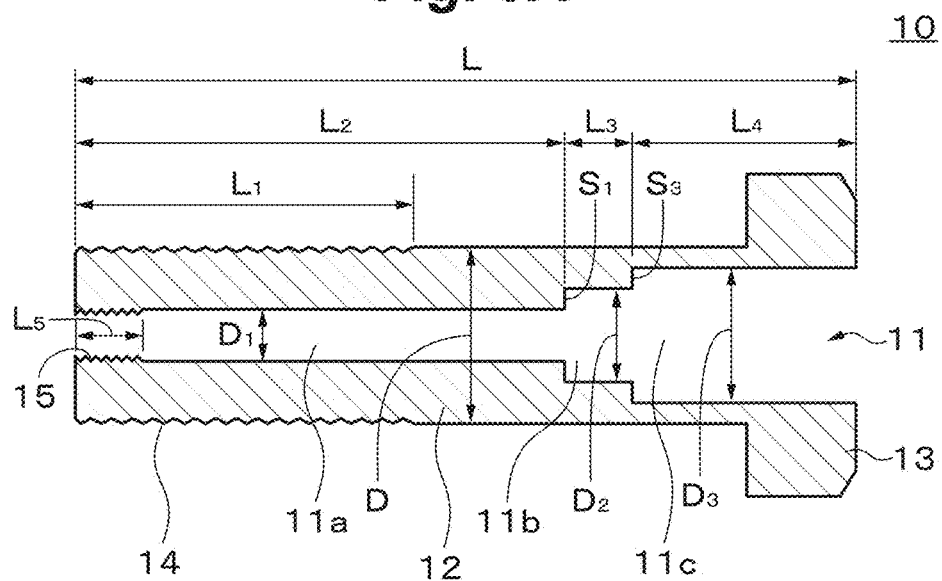
FIG. 9A A longitudinal cross sectional view showing the first member constituting the failure detection sensor according to the second embodiment of the invention.
Figure 9B:
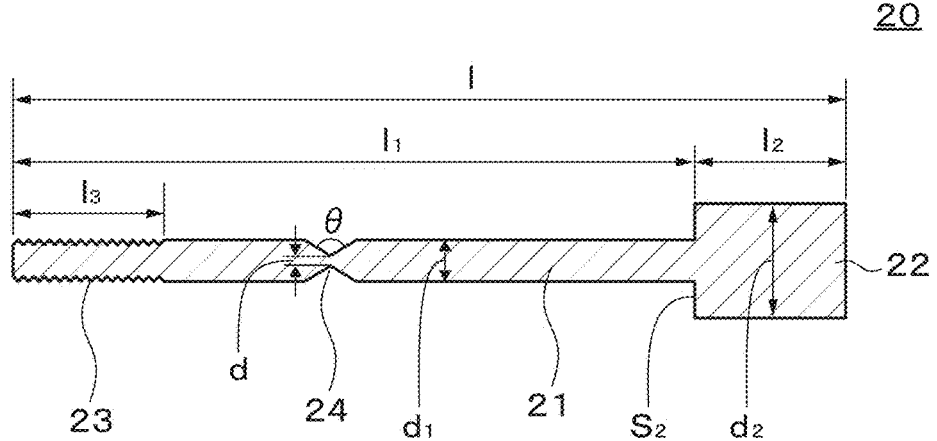
FIG. 9B A longitudinal cross sectional view showing the second member constituting the failure detection sensor according to the second embodiment of the invention.

FIG. 8A, FIG. 8B, FIG. 8C, FIG. 8D and FIG. 8E show the failure detection sensor according to the second embodiment, where FIG. 8A is a front view, FIG. 8B is a left side view, FIG. 8C is a right side view, FIG. 8D is a longitudinal cross sectional view and FIG. 8E is a cross sectional view along the E-E line of FIG. 8A. FIG. 9A shows details of the first member 10, and FIG. 9B shows details of the second member 20.

As shown in FIG. 8A, FIG. 8B, FIG. 8C, FIG. 8D, FIG. 8E, FIG. 9A and FIG. 9B, in the failure detection sensor, a female screw 15 is cut on the inner peripheral surface of the hollow part 11 of the axial part 12 of the first member 10 over a length $L_5$ from the front end of the axial part 12. The male screw 23 is cut on the outer peripheral surface of the axial part 21 of the second member 20 over the length $l_3$ from the front end of the axial part 21 larger than that of the first embodiment. And the male screw 23 on the outer peripheral surface of the axial part 21 of the second member 20 is screwed into the female screw 15 on the inner peripheral surface of the hollow part 11 of the axial part 12 of the first member 10. With this, the front part of the second member 20 is fixed to the front part of the first member 10.

Other than the above of the failure detection sensor is the same as the failure detection sensor according to the first embodiment.

According to the second embodiment, the same advantages as the first embodiment can be obtained.

3. The Third Embodiment

[Failure Detection Sensor]

In the failure detection sensor according to the third embodiment, the nut 30 fitted to the male screw 23 of the axial part 21 of the second member 20 is fixed to the front part of the first member 10 by welding, gluing, brazing, etc. With this, the front part of the second member 20 is fixed to the front part of the first member 10.

Other than the above of the failure detection sensor is the same as the failure detection sensor according to the first embodiment.

According to the third embodiment, the same advantages as the first embodiment can be obtained.

4. The Fourth Embodiment

[Failure Detection Sensor]

Figure 10A:
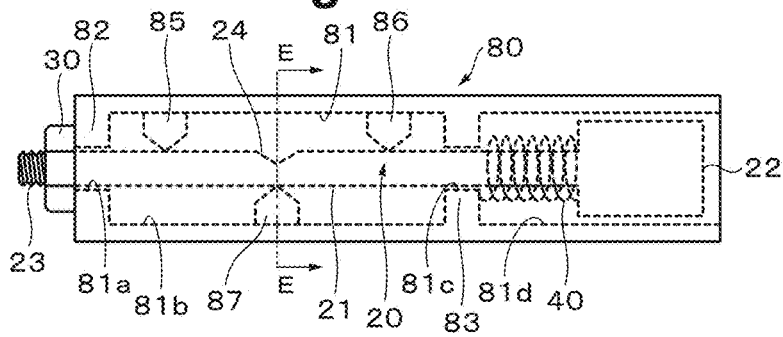
FIG. 10A A front view showing a failure detection sensor according to the fourth embodiment of the invention.
Figure 10B:
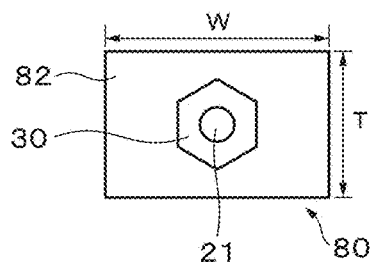
FIG. 10B A left side view showing the failure detection sensor according to the fourth embodiment of the invention.
Figure 10C:
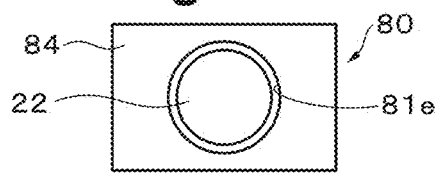
FIG. 10C A right side view showing the failure detection sensor according to the fourth embodiment of the invention.
Figure 10D:
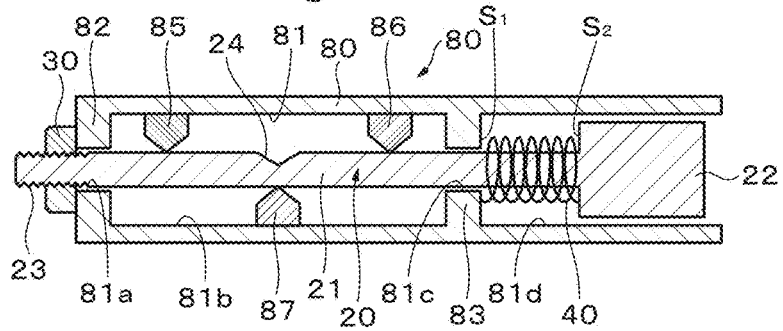
FIG. 10D A longitudinal cross sectional view showing the failure detection sensor according to the fourth embodiment of the invention.
Figure 10E:
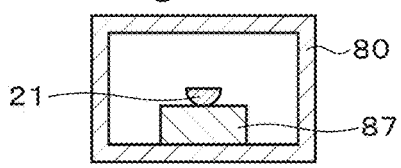
FIG. 10E A cross sectional view showing the failure detection sensor according to the fourth embodiment of the invention.

FIG. 10A, FIG. 10B, FIG. 10C, FIG. 10D and FIG. 10E show the failure detection sensor according to the fourth embodiment, where FIG. 10A is a front view, FIG. 10B is a left side view, FIG. 10C is a right side view, FIG. 10D is a longitudinal cross sectional view and FIG. 10E is a cross sectional view along the E-E line of FIG. 10A. The failure detection sensor is especially suitable for detection of bend fracture.

As shown in FIG. 10A, FIG. 10B, FIG. 10C, FIG. 10D and FIG. 10E, the failure detection sensor comprises a rectangular parallelepiped-like first member 80 with a hollow part 81, and the circular rod-like second member 20 inserted into the hollow part 81 of the first member 80. The second member 20 has fracturing characteristics such that it fractures during elastic deformation or plastic deformation of the first member 80.

Figure 11A:
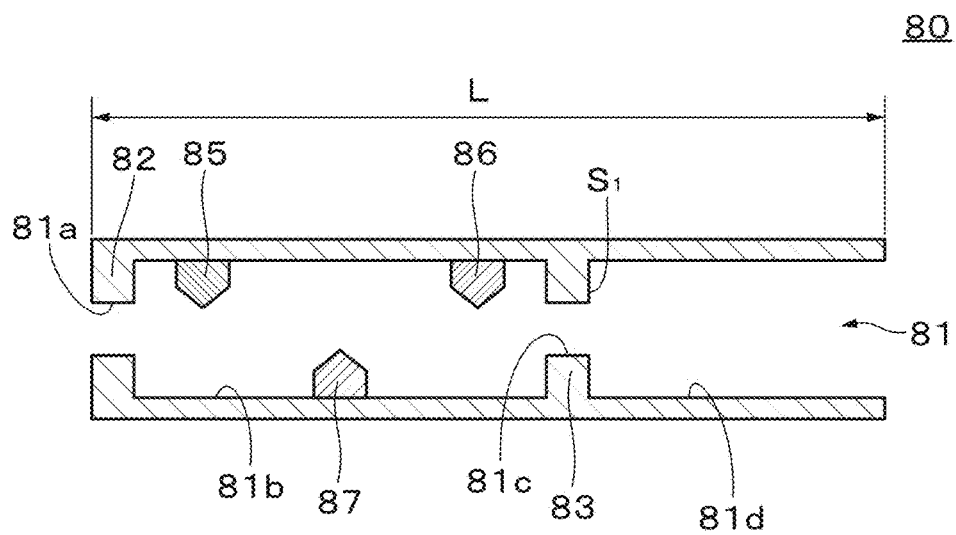
FIG. 11A A longitudinal cross sectional view showing the first member constituting the failure detection sensor according to the fourth embodiment of the invention.
Figure 11B:
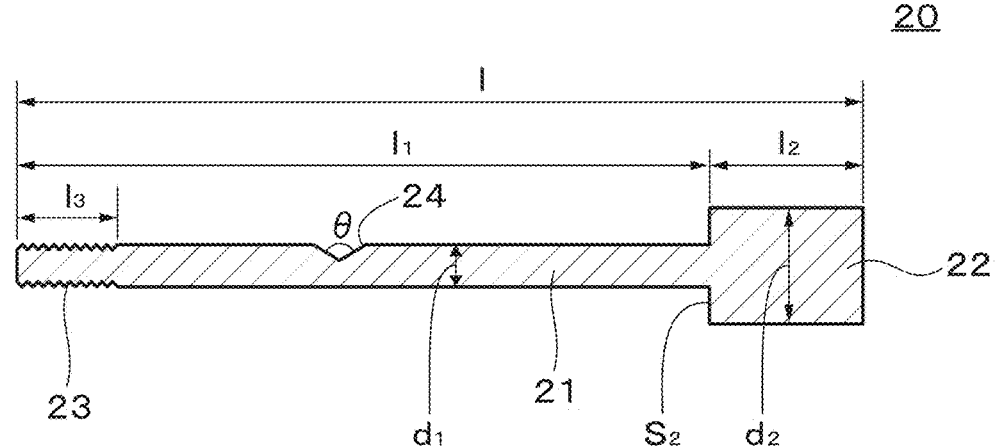
FIG. 11B A longitudinal cross sectional view showing the second member constituting the failure detection sensor according to the fourth embodiment of the invention.

FIG. 11A shows details of the first member 80, and FIG. 11B shows details of the second member 20. When the total length of the first member 80 is denoted as L and the total length of the second member 20 is denoted as l, typically, L<l, but not limited to this.

As shown in FIG. 10A, FIG. 10B, FIG. 10C, FIG. 10D, FIG. 10E and FIG. 11A, the first member 80 has a length L, a width W and a thickness T. The hollow part 81 of the first member 80 comprises the eleventh part 81a, the twelfth part 81b, the thirteenth part 81c, the fourteenth part 81d and the fifteenth part 81e in order from one end to the other end of the first member 80. The eleventh part 81a is a cylindrical hole with a diameter $D_1$ which is provided in an outer wall 82 on one end of the first member 80. The twelfth part 81b has a rectangular parallelepiped shape. The thirteenth part 81c is a cylindrical hole with the diameter $D_1$ which is provided in a partition wall 83 in the hollow part 81. The fourteenth part 81d has a rectangular parallelepiped shape. The fifteenth part 81e is a cylindrical hole provided in an outer wall 84 on the other end of the first member 80. The cross sectional shape of the twelfth part 81b and the fourteenth part 81d is rectangular at any position. The eleventh part 81a, the thirteenth part 81c and the fifteenth part 81e are provided coaxially one another. Two projections 85, are provided on the ceiling of the twelfth part 81b perpendicularly to the ceiling plane at positions apart from each other in the longitudinal direction of the first member 80. Front ends (lower ends) of the projections 85, 86 locate at a height a little lower than the topmost ends of the eleventh part 81a and the thirteenth part 81c and are in contact with or lie adjacent to the upper end of the axial part 21 of the second member 20. A projection 87 is provided on the base of the twelfth part 81b perpendicularly to the base. The projection 87 is provided, for example, so as to locate on a plane bisecting between the projection 85 and the projection 86, but not limited to this. The front end of the projection 87 locates at a height a little higher than the lower most ends of the eleventh part 81a and the thirteenth part 81c and is in contact with or lies adjacent to the lower end of the axial part 21 of the second member 20. As shown in FIG. 10E, the projection 87 extends in a plane perpendicular to the central axis of the first member 80 and has a rectangular shape when it is seen from the direction of the central axis of the first member 80. This is the same for the projections 85, 86.

As shown in FIG. 10B, the second member 20 comprises the cylinder-like axial part 21 with a diameter $d_1$ and a length $l_1$, and the cylinder-like head part 22 with a diameter $d_2$ (here, $d_2>d_1$) and a length $l_2$. The V groove-like notch 24 which becomes a stress concentration site is provided horizontally on the outer peripheral surface of the axial part 21 at the upper part of the axial part 21. The position of the notch 24 is preferably adjusted to the position of the front end of the projection 87, but not limited to this.

As shown in FIG. 10A, FIG. 10B, FIG. 10C, FIG. 10D and FIG. 10E, the axial part 21 of the second member 20 is inserted into the eleventh part 81a, the twelfth part 81b, the thirteenth part 81c, the fourteenth part 81d and the fifteenth part 81e of the hollow part 81 of the first member 80, and the front end of the axial part 21 protrudes from the end surface of the first member 80. And the nut 30 is fitted to the male screw 23 of the front end of the axial part 21.

The head part 22 of the second member 20 is accommodated in the fourteenth part 81d of the hollow part 81 of the first member 80. The compression coil spring 40 is provided on a part of the axial part 21 of the second member 20 on the side of the head part 22 such that it is penetrated by the axial part 21. The compression coil spring 40 is accommodated in the fourteenth part 81d of the hollow part 81 of the first member 80 in a compressed state. The diameter of the compression coil spring 40 is a litter smaller than the height of the fourteenth part 81d. By the restituitive force applied by compression of the compression coil spring 40, one end of the compression coil spring 40 presses the side surface of a $S_1$ between the thirteenth part 81c and the fourteenth part 81d, and the other end of it presses the end surface $S_2$ of the head part 22 of the second member 20 on the side of the axial part 21. Since the end surface $S_2$ of the head part 22 is pressed by the restituitive force of the compression coil spring 40, the axial part 21 of the second member is pulled on the side of the head part 22. With this, the front part of the second member 20 is restricted to the front part of the first member 80.

Sizes (L, l, $l_1$~$l_3$, $d_1$, $d_2$, θ, etc.) of each part of the failure detection sensor are selected depending on the structure to which the failure detection sensor is attached etc. as needed.

Other than the above constitution of the failure detection sensor is the same as the failure detection sensor according to the first embodiment.

[Method of Controlling Failure Sensitivity of the Failure Detection Sensor]

The failure sensitivity (permissible deformation amount) of the failure detection sensor can be controlled by the shape and depth (notch length) of the notch 24 of the second member 20, in other words, the notch angle θ of the tip of the notch 24 and a height in the vertical direction of the tip of the notch 24, a length $\Delta=D_1-d_1$ of the gap between the inner peripheral surface of the eleventh part 81a and the thirteenth part 81c of the hollow part 81 of the first member 80 and the axial part 21 of the second member 20, etc. Here, when Δ is large, the time from occurrence of bend deformation of the first member 80 to the beginning of affecting the second member 20 is long, which results in degradation of the failure sensitivity. The shape and depth of the notch 24 affect the bend strength of the second member 20.

[Method of Using the Failure Detection Sensor]

Figure 12A:
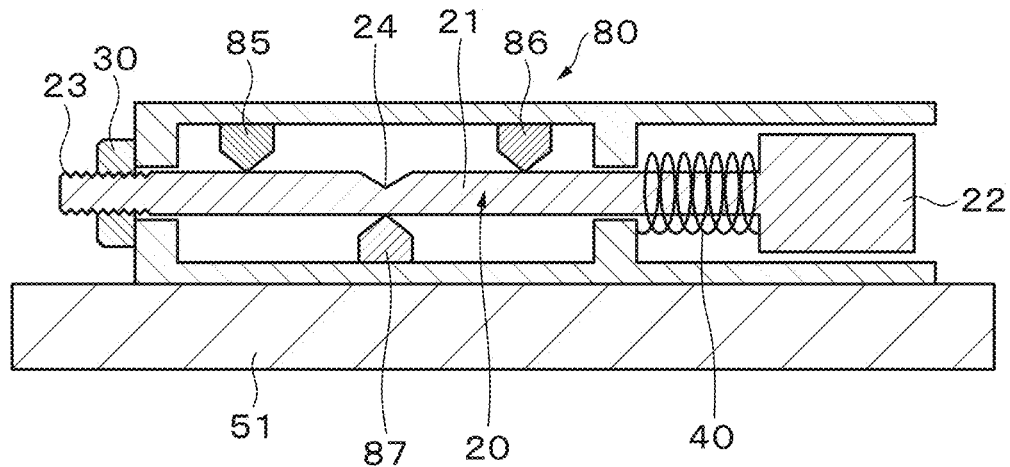
FIG. 12A A longitudinal cross sectional view showing a state in which the failure detection sensor according to the fourth embodiment of the invention is attached to the structure.
Figure 12B:
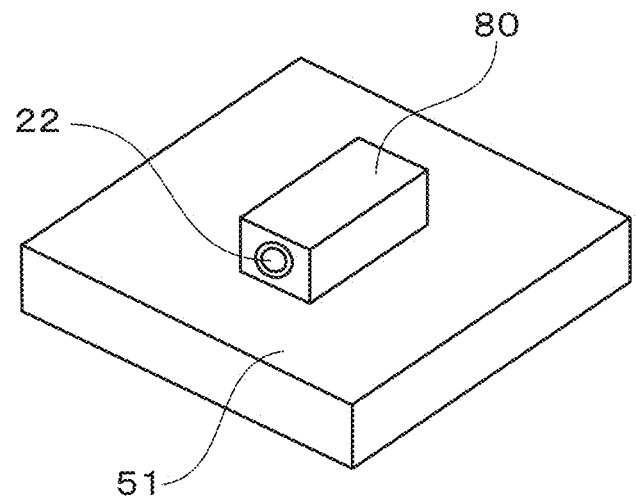
FIG. 12B A perspective view showing the state in which the failure detection sensor according to the fourth embodiment of the invention is attached to the structure.

As shown in FIG. 12A and FIG. 12B, the failure detection sensor is attached to the structural member 51 to be detected failure. As an attaching method of the failure detection sensor various methods can be used as far as the failure detection sensor can be fixed with the strength enough to suppress detachment of the failure detection sensor from the structural member 51 when mechanical deformation of the structural member 51 occurs. The attaching method is, for example, screw clamp, welding, etc.

Figure 13A:
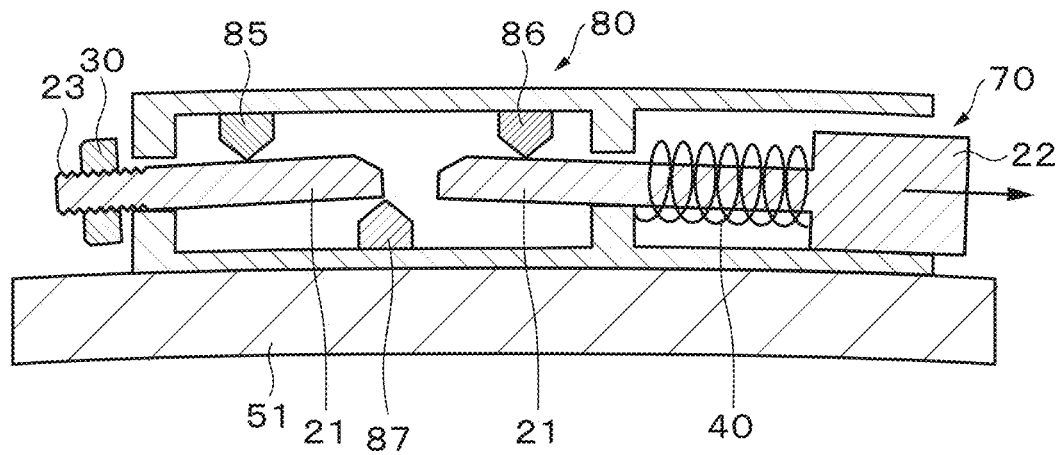
FIG. 13A A longitudinal cross sectional view showing a state in which a strong bending moment acts on the structure to which the failure detection sensor according to the fourth embodiment of the invention is attached.
Figure 13B:
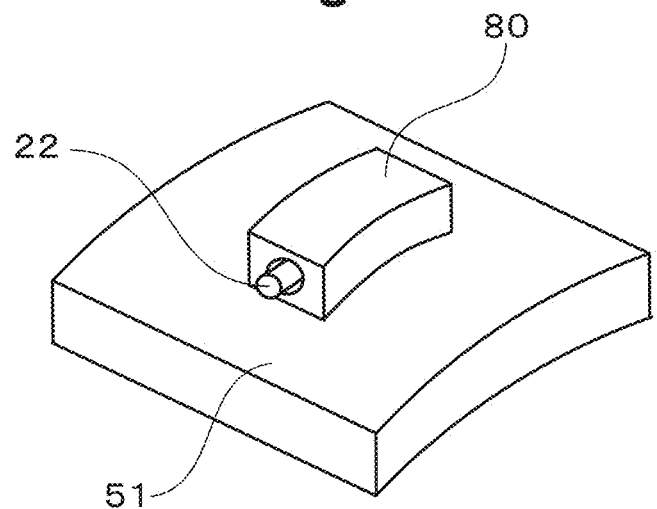
FIG. 13B A perspective view showing the state in which a strong bending moment acts on the structure to which the failure detection sensor according to the fourth embodiment of the invention is attached.

Described is now a case where the structural member 51 is given a bending moment which bends the structural member 51 upward. When the structural member 51 is given a bending moment, it is bent upward, and finally, the first member 80 is also bent upward. As a result, the second member 20 is bent with supporting points of three points consisting of each tip of the projections 85 to 87. That is, the second member 20 is given a three-point bending. When the structural member 51 is given a larger bending moment, the structural member 51, and thus the first member 80 is bent more. When the degree of bending reaches a certain level, as shown in FIG. 13A and FIG. 13B, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 80 at one end of the second member 20. As a result, the head part 22 of the fractured piece 70 moves outward inside the fourteenth part 81d and the fifteenth part 81e of the hollow part 81 of the first member 80 by the restituitive force of the compression coil spring 40, and protrudes outward.

It is easy to recognize visually from the outside, for example, that the head part 22 of the fractured piece 70 protrudes outside the first member 10 as described above. From the result, it is possible to decide that there is the risk of the failure since the structural members 51 is given the bending moment.

As described above, according to the fourth embodiment, the same advantages as the first embodiment can be obtained with respect to bend fracture of the structure.

5. The Fifth Embodiment

[Failure Detection Sensor]

Figure 14:
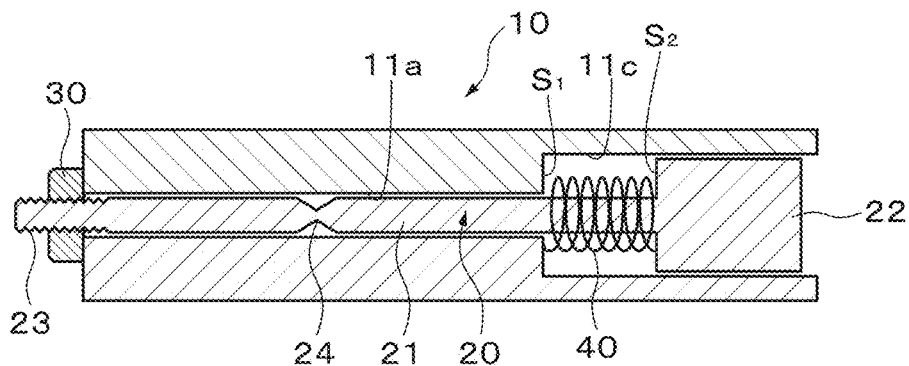
FIG. 14 A longitudinal cross sectional view showing a failure detection sensor according to the fifth embodiment of the invention.

FIG. 14 shows the failure detection sensor according to the fifth embodiment. The failure detection sensor is especially suitable for detection of torsion fracture, shear fracture, bend fracture, compression fracture, etc.

As shown in FIG. 14, the failure detection sensor is different from the failure detection sensor according to the first embodiment in that the first member 20 does not have a bolt-like shape but a quadratic prism-like shape, and the hollow part 11 of the first member 10 comprises only the first part 11a and the third part 11c. In this case, the compression coil spring 40 is accommodated in the third part 11c. Other constitution is the same as the failure detection sensor according to the first embodiment.

[Method of Controlling Failure Sensitivity of the Failure Detection Sensor]

The failure sensitivity (permissible deformation amount) of the failure detection sensor can be controlled by the shape and depth (notch length) of the notch 24 of the second member 20, in other words, the notch angle θ of the tip of the notch 24 and the diameter d of the axial part 21 at the tip of the notch 24, and the length $\Delta=D_1-d_1$ of the gap between the inner peripheral surface of the first part 11a of the hollow part 11 of the first member and the axial part 21 of the second member 20, etc. Here, when Δ is large, the time from occurrence of torsional deformation etc. to the beginning of affecting the second member 20 is long, which results in degradation of the failure sensitivity. The shape and depth of the notch 24 affect the bend strength of the second member 20.

[Method of Using the Failure Detection Sensor]

Figure 15:
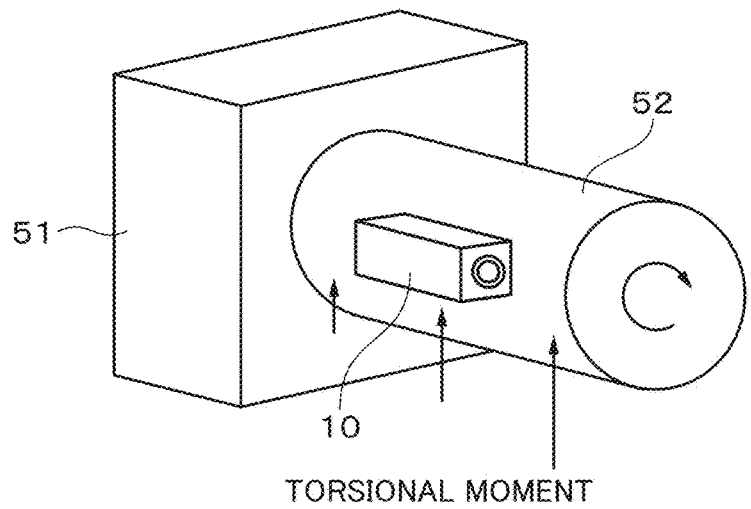
FIG. 15 A perspective view showing a state in which the failure detection sensor according to the fifth embodiment of the invention is attached to the structure.

Described as an example is a case where the failure detection sensor is applied for detection of torsion fracture, but it can also be applied for detection of shear fracture, bend fracture and compression fracture. As shown in FIG. 15, the cylinder-like structural member 52 is vertically provided on the structural member 51 of the structure to be detected failure. The structural member 52 is a cantilever with the fixed end on the structural member 51. The failure detection sensor shown in FIG. 14 is attached to the outer peripheral surface of the structural member 52 such that the longitudinal direction of the failure detection sensor coincides with the longitudinal direction of the structural member 52 and is parallel with the central axis of the structural member 52. As an attaching method of the failure detection sensor various methods can be used as far as the failure detection sensor can be fixed with the strength enough to suppress detachment of the failure detection sensor from the structural member 52 when torsional deformation occurs. The attaching method is, for example, screw clamp, welding, etc.

Figure 16:
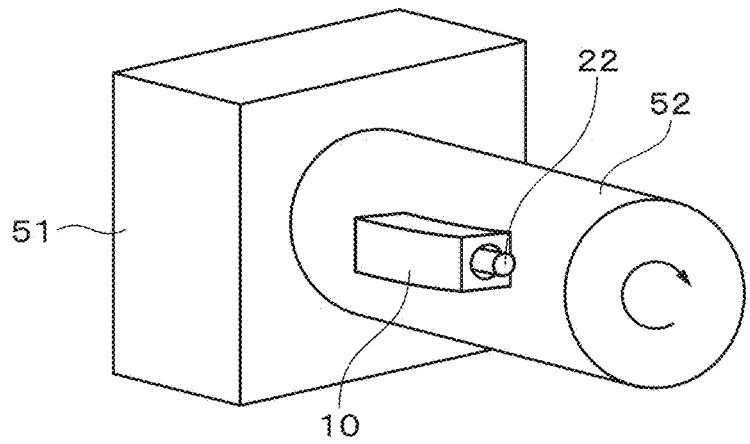
FIG. 16 A perspective view showing a state in which a strong torsional moment acts on the structure to which the failure detection sensor according to the fifth embodiment of the invention is attached.
Figure 17:
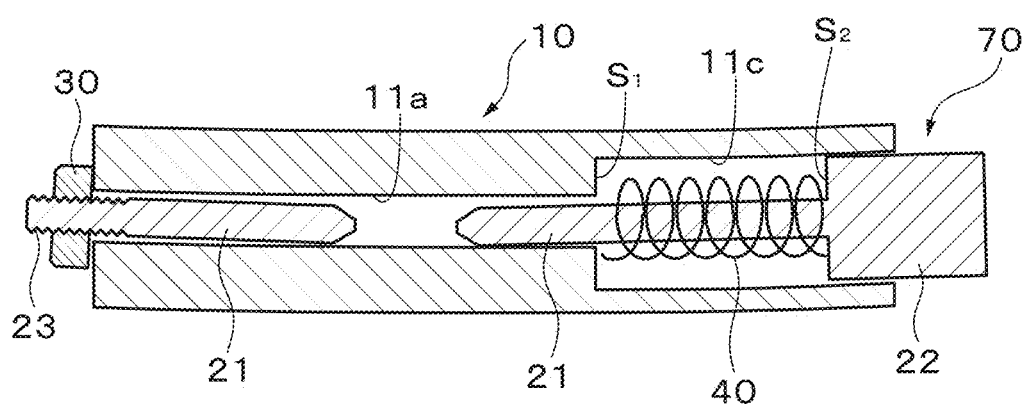
FIG. 17 A longitudinal cross sectional view showing a state in which a strong torsional moment acts on the structure to which the failure detection sensor according to the fifth embodiment of the invention is attached and the second member fractures.

As shown in FIG. 15, described is now a case where the structural member 52 is given a torsional moment which twists the structural member 52 around its central axis. As shown in FIG. 16, when the structural member 52 is given a torsional moment, the first member 10 of the failure detection sensor is also given a torsional moment and twisted. An amount of torsion of the structural member 52 increases from the side of the structural member 51 toward the other end. When the structural member 52 is given a larger torsional moment, the first member 10 is also given a larger torsional moment, and finally, the second member 20 produces bend deformation from the front end toward the other end. As shown in FIG. 16 and FIG. 17, when the degree of torsion of the first member 10 reaches a certain level, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 10 at one end of the second member 20. As a result, the head part 22 of the fractured piece 70 moves outward inside the third part 11c of the hollow part 11 of the first member 10 by the restituitive force of the compression coil spring 40, and protrudes outward. In this case, since the notch 24 is formed over the whole circumference of the second member 20, the second member 20 securely fractures at the notch 24 without depending on the direction of torsion of the first member 10 and how the second member 20 is bent.

It is easy to recognize visually from the outside, for example, that the head part 22 of the fractured piece 70 protrudes outside the first member 10 as described above. From the result, it is possible to decide that there is the risk of the failure since the structural member 52 is given the torsional moment.

As described above, according to the fifth embodiment, the same advantages as the first embodiment can be obtained with respect to detection of torsion fracture, shear fracture, bend fracture or compression fracture of the structure.

6. The Sixth Embodiment

[Failure Detection Sensor]

Figure 18A:
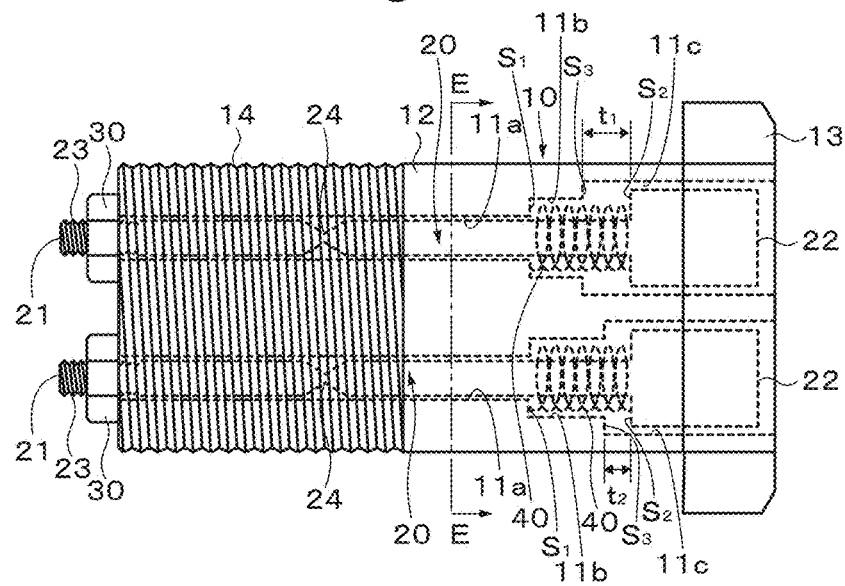
FIG. 18A A front view showing a failure detection sensor according to the sixth embodiment of the invention.
Figure 18B:
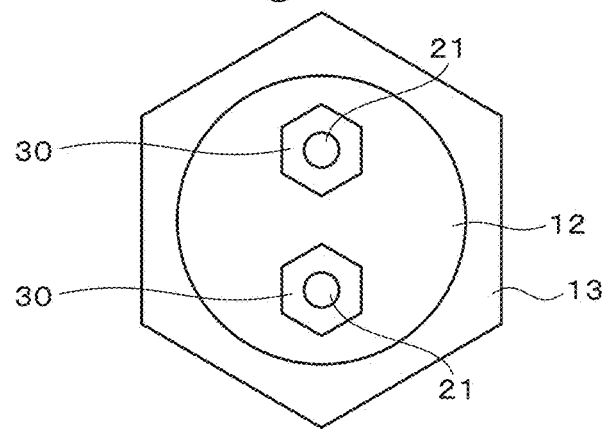
FIG. 18B A left side view showing the failure detection sensor according to the sixth embodiment of the invention.
Figure 18C:
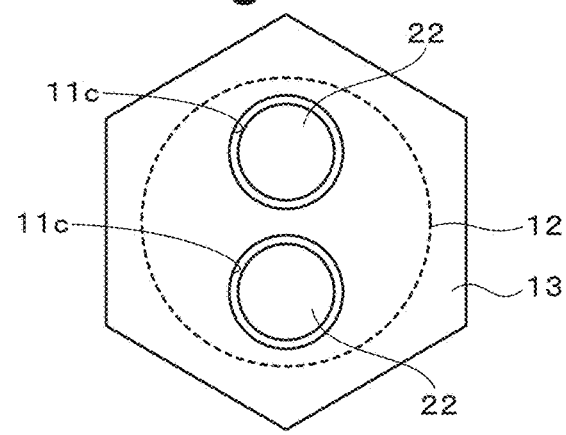
FIG. 18C A right side view showing the failure detection sensor according to the sixth embodiment of the invention.
Figure 19A:
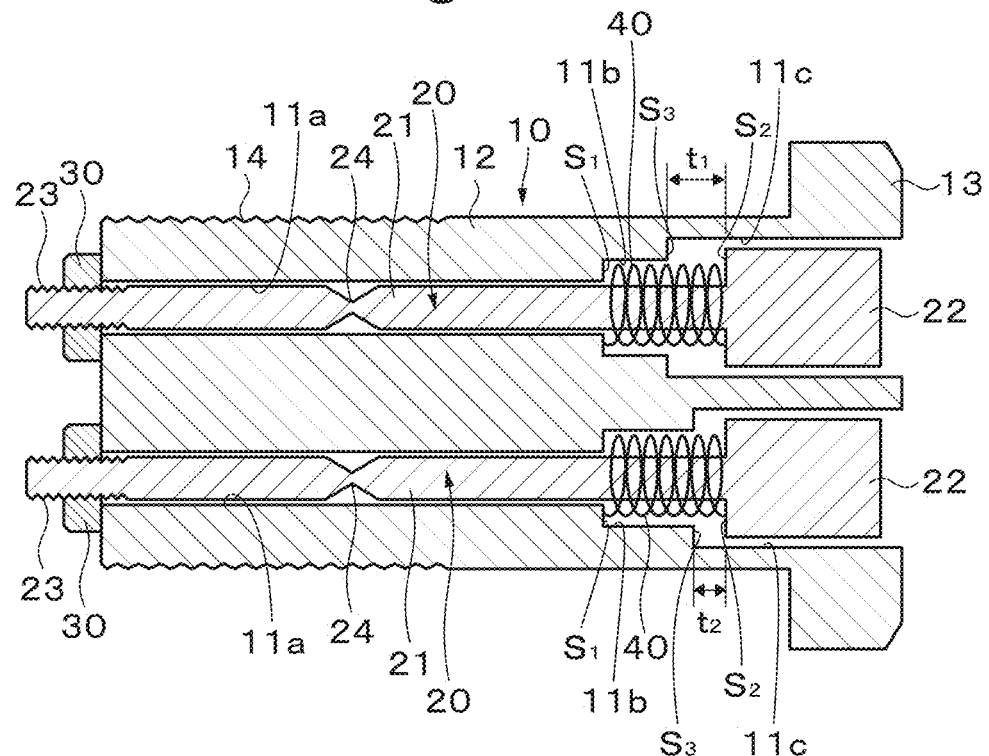
FIG. 19A A longitudinal cross sectional view showing the failure detection sensor according to the sixth embodiment of the invention.
Figure 19B:
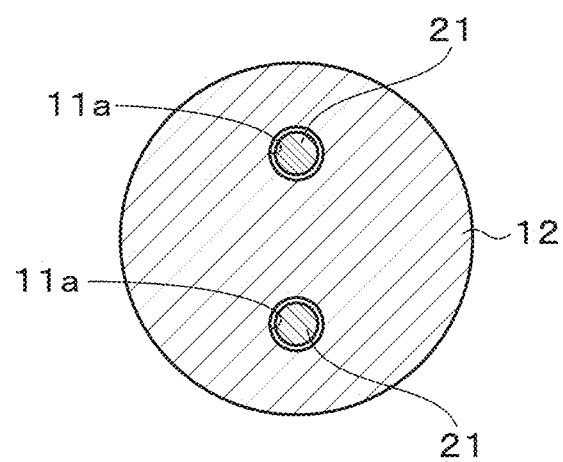
FIG. 19B A cross sectional view showing the failure detection sensor according to the sixth embodiment of the invention.

FIG. 18A, FIG. 18B, FIG. 18C, FIG. 19A and FIG. 19B show the failure detection sensor according to the sixth embodiment, where FIG. 18A is a front view, FIG. 18B is a left side view, FIG. 18C is a right side view, FIG. 19A is a longitudinal cross sectional view and FIG. 19B is a cross sectional view along the E-E line of FIG. 18A. The failure detection sensor is constituted of two types of failure detection sensor with different failure sensitivity each other which are provided in parallel and unified.

As shown in FIG. 18A, FIG. 18B, FIG. 18C, FIG. 19A and FIG. 19B, the failure detection sensor is constituted of the failure detection sensors according to the first embodiment built in the hexagonal bolt-like first member 10 as one body. That is, the failure detection sensor comprises the hexagonal bolt-like first member 10 with two hollow parts 11 which are parallel each other and the two circular rod-like second member 20 which are inserted into the two hollow parts 11 of the first member 10 respectively. The second members 20 have fracturing characteristics such that they fracture during elastic deformation or plastic deformation of the first member 10. The two hollow parts 11 are provided in positions which are distant from the central axis of the first member 10 by the same distance, and sandwich the central axis in one diameter direction of the cross section of the first member 10. Hereunder, as shown in FIG. 18A, FIG. 18B, FIG. 18C, FIG. 19A and FIG. 19B, the upper hollow part 11 of one of the two hollow parts 11 and the second member 20 inserted therein are referred as an upper failure detection sensor and the lower hollow part 11 of another one of the two hollow parts 11 and the second member 20 inserted therein are referred as a lower failure detection sensor. Although both the upper failure detection sensor and the lower failure detection sensor have the same constitution as the failure detection sensor according to the first embodiment, positions of the ring-like side surface of a step $S_3$ between the second part 11b and the third part 11c are different each other, and the position of the side surface of a step $S_3$ of the lower failure detection sensor is nearer to the head part 13 of the first member 10 than that of the upper failure detection sensor. Therefore, when the distance between the side surface of a step $S_3$ of the first member 10 and the end surface $S_2$ of the head 22 of the second member 20 of the upper failure detection sensor is denoted as $t_1$, and the distance between the side surface of a step $S_3$ of the first member 10 and the end surface $S_2$ of the head 22 of the second member 20 of the lower failure detection sensor is denoted as $t_2$, $t_2 < t_1$ is satisfied. That is, the failure sensitivity of the upper failure detection sensor and the lower failure detection sensor are different each other, and the failure sensitivity of the lower failure detection sensor is higher than that of the upper failure detection sensor. As a result, when the first member 10 produces elastic deformation or plastic deformation, the second member 20 of the lower failure detection sensor fractures first, and then the second member 20 of the upper failure detection sensor fractures. That is, the failure detection sensor can detect failure in two stages.

Other than the above of the failure detection sensor is the same as the first embodiment.

[Method of Using the Failure Detection Sensor]

Figure 20:
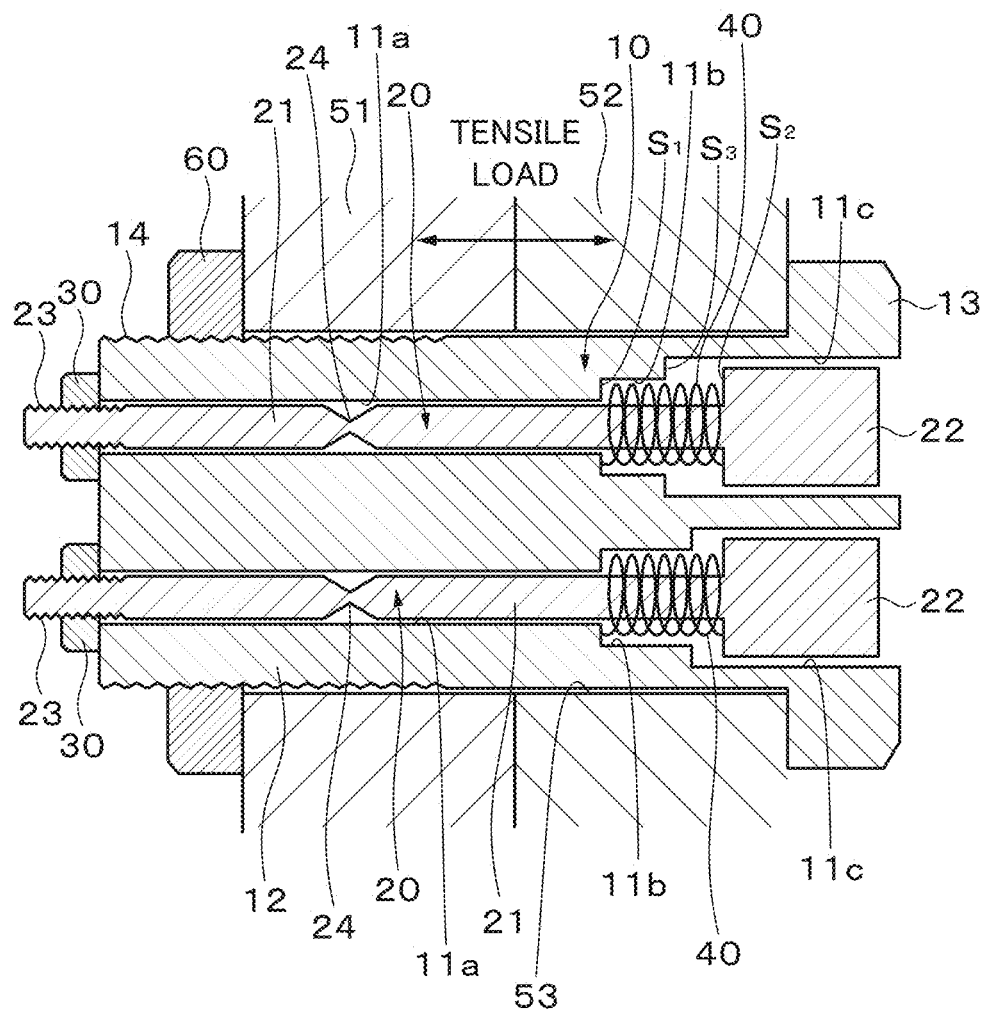
FIG. 20 A cross sectional view showing a state in which the failure detection sensor according to the sixth embodiment of the invention is attached to the junction of the structure shown in FIG. 3.

As shown in FIG. 20, the failure detection sensor is attached to the structural members 51, 52 to be detected failure as the same as the first embodiment.

As the same as the failure detection sensor according to the first embodiment, when the structural members 51, 52 are given a tensile load, they are separated, and thus the axial part 11 of the first member 10 is elongated. When the structural members 51, 52 are given a larger tensile load, elongation of the axial part 11 becomes larger. When elongation of the axial part 11 reaches to a certain extent, first, the side surface of a step $S_3$ (the press surface) of the first member 10 of the lower failure detection sensor comes in contact with the end surface $S_2$ (the surface to be pressed) of the second member 20, and begins to press it. As elongation of the axial part 11 becomes further larger, the side surface of a step $S_3$ presses the end surface $S_2$ more strongly. In this way, when the side surface of a step $S_3$ of the first member 10 of the lower failure detection sensor presses the end surface $S_2$ of the second member 20, the second member 20 is given a tensile load in the axial direction and elongated. And when elongation of the axial part 11 becomes $t_2 + \delta$, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 10 at one end of the second member 20. As a result, the head part 22 of the second member 20 moves inside the third part 11s of the hollow part 11 of the first member 10 outward by the restituitive force of the compression coil spring 40, and protrudes outward. When the tensile load given to the structural members 51, 52 becomes larger, the side surface of a step $S_3$ (the press surface) of the first member 10 of the upper failure detection sensor comes in contact with the end surface $S_2$ (the surface to be pressed), and begins to press it. As elongation of the axial part 21 becomes further larger, the side surface of a step $S_3$ presses the end surface $S_2$ more strongly. In this way, when the side surface of a step $S_3$ of the first member 10 presses the end surface $S_2$ of the second member 20, the second member 20 is given a tensile load in the axial direction and elongated. And when elongation of the axial part 11 becomes $t_1+\delta$, the second member 20 fractures at the notch 24 which is a stress concentration site, and is divided into two pieces. At this time, the fractured piece 70 which corresponds to the part of the second part 20 on the side of the head part 22 from the fractured part becomes free from mechanical restriction by the first member 10 at one end of the second member 20. As a result, the head part 22 of the second member 20 moves inside the third part 11c of the hollow part 11 of the first member 10 outward by the restituitive force of the compression coil spring 40, and protrudes outward.

It is easy to recognize visually from the outside, for example, that the head parts 22 of the two second members 20 protrude outside the first member 10 as described above. As a result, it can be decided in two stages that there is the risk of the fracture of the structural members 51, 52 because they are given the tensile load.

According to the sixth embodiment, in addition to the same advantages as the first embodiment, it is possible to obtain an advantage that since detection of failure can be carried out in two stages, mechanical deformation produced in the structure by the tensile load can be decided more correctly and more accurate detection of the risk can be carried out.

7. The Seventh Embodiment

[Failure Detection Sensor]

Figure 21A:
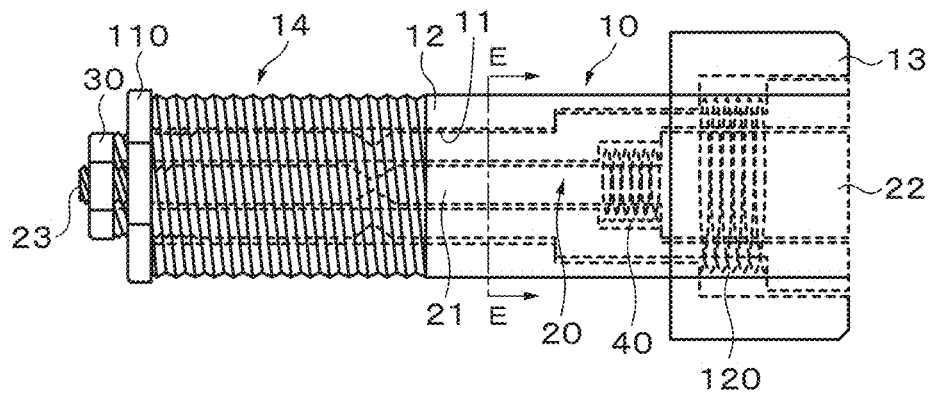
FIG. 21A A front view showing a failure detection sensor according to the seventh embodiment of the invention.
Figure 21B:
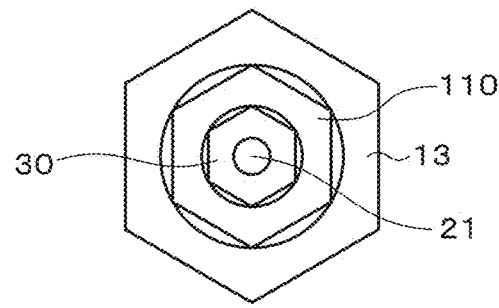
FIG. 21B A left side view showing the failure detection sensor according to the seventh embodiment of the invention.
Figure 21C:
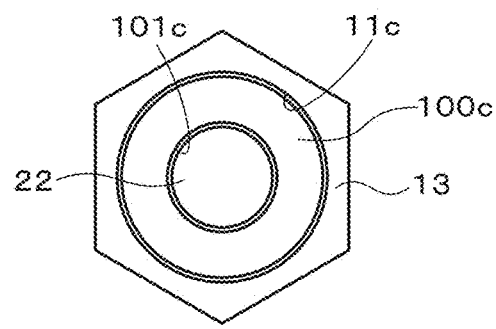
FIG. 21C A right side view showing the failure detection sensor according to the seventh embodiment of the invention.
Figure 21D:
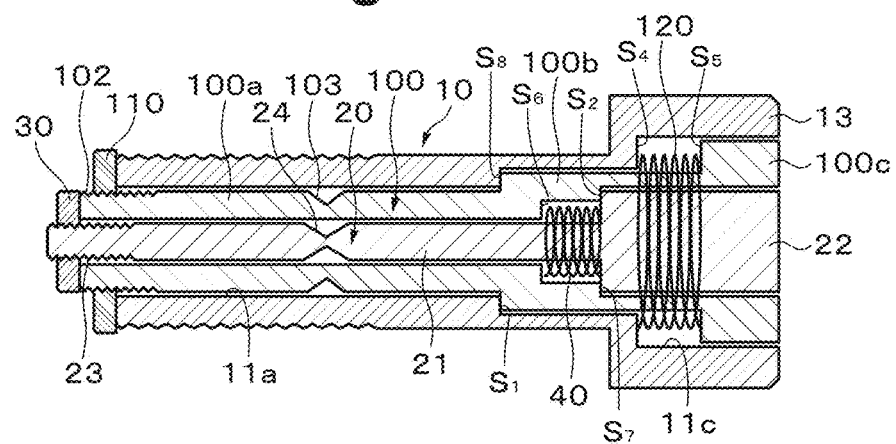
FIG. 21D A longitudinal cross sectional view showing the failure detection sensor according to the seventh embodiment of the invention.
Figure 21E:
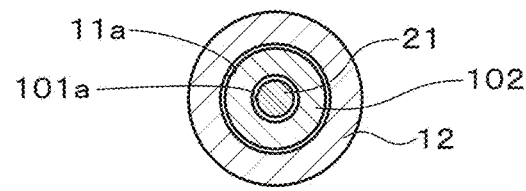
FIG. 21E A cross sectional view showing the failure detection sensor according to the seventh embodiment of the invention.

FIG. 21A, FIG. 21B, FIG. 21C, FIG. 21D and FIG. 21E show the failure detection sensor according to the seventh embodiment, where FIG. 21A is a front view, FIG. 21B is a left side view, FIG. 21C is a right side view, FIG. 21D is a longitudinal cross sectional view and FIG. 21E is a cross sectional view along the E-E line of FIG. 21A. The failure detection sensor has a double structure and can carry out detection of failure in two stages.

As shown in FIG. 21A, FIG. 21B, FIG. 21C, FIG. 21D and FIG. 21E, the failure detection sensor comprises the hexagonal bolt-like first member 10 with the hollow part 11, a rod-like third member 100 with a hollow part 101 and the circular rod-like second member 20. The third member 100 is inserted into the hollow part 11 of the first member 10, and the second member 20 is inserted into the hollow part 101 of the third member 100. The first member 10, the third member 100 and the second member 20 are provided coaxially. The second member 20 and the third member 100 have fracturing characteristics such that they fracture during elastic deformation or plastic deformation of the first member 10.

Figure 22A:
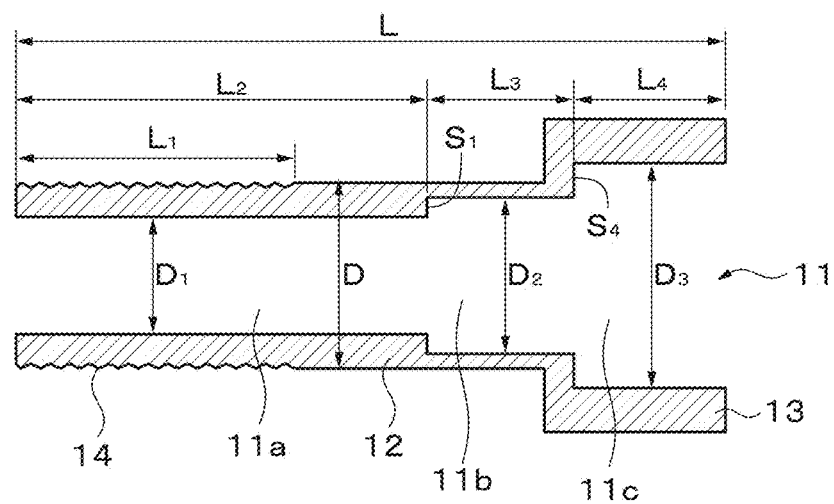
FIG. 22A A longitudinal cross sectional view showing the first member constituting the failure detection sensor according to the seventh embodiment of the invention.
Figure 22B:
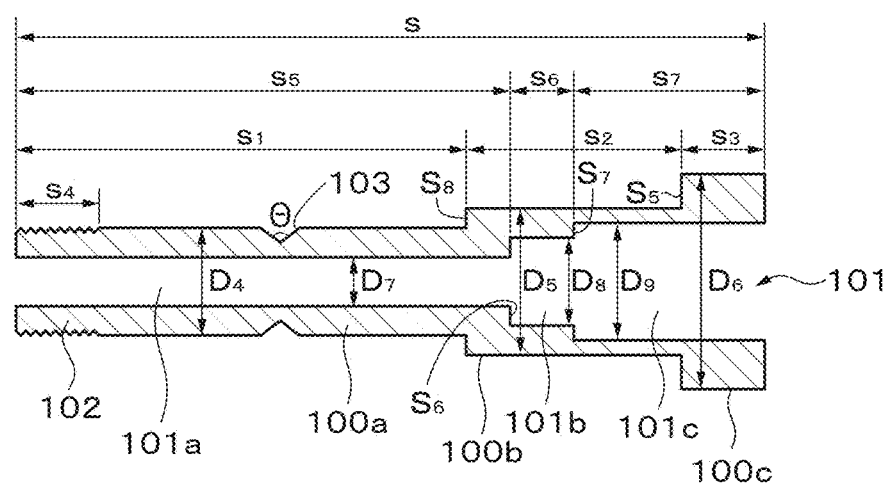
FIG. 22B A longitudinal cross sectional view showing the second member constituting the failure detection sensor according to the seventh embodiment of the invention.
Figure 22C:
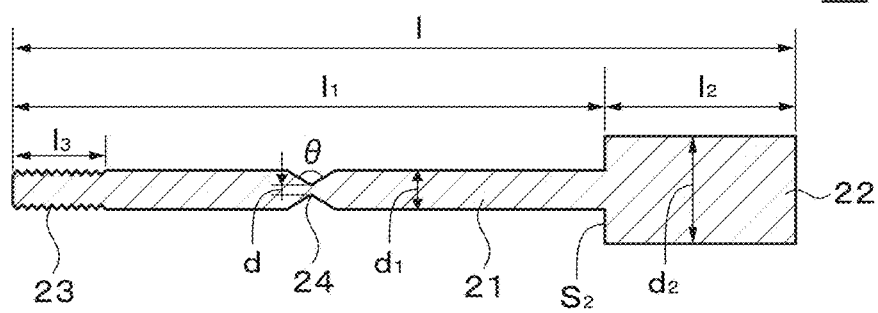
FIG. 22C A longitudinal cross sectional view showing the third member constituting the failure detection sensor according to the seventh embodiment of the invention.

FIG. 22A shows details of the first member 10, FIG. 22B shows details of the third member 100, and FIG. 22C shows details of the second member 20. When the total length of the first member 10 is denoted as L, the total length of the second member 20 is denoted as l, and the total length of the third member 100 is denoted as s, typically L<s<l is satisfied, but not limited to this.

As shown in FIG. 22A, the first member 10 comprises the cylinder-like axial part 12 with the diameter D, and the hexagonal cylinder-like head part 13 thicker than the axial part 12. The male screw 14 is cut on the outer peripheral surface of the axial part 12 over an area of the length $L_1$ from the front edge of the axial part 12. The male screw 14 is used to fit a nut or screw into a female screw formed in the inner peripheral surface of a hole formed in the structure when the failure detection sensor is attached to the structure to be detected failure. The shape of the cross section of the hollow part 11 of the first member 10 is a circle centered in the central axis of the first member 10 in any position. The hollow part 11 comprises the first part 11a with the diameter $D_1$ (here, $D_1$<D) and the length $L_2$, the second part 11b with the diameter $D_2$ (here, $D_2$>$D_1$) and the length $L_3$, and the third part 11c with the diameter $D_3$ (here, D>$D_3$>$D_2$) and the length $L_4$ in order from the front end of the axial part 12. Here, $L_2+L_3+L_4=L$.

As shown in FIG. 22B, the third member 100 comprises a front end part 100a with an outer diameter $D_4$, an intermediate part 100b with an outer diameter $D_5$, and a head part 100c with an outer diameter $D_6$. Lengths of the front end part 100a, the intermediate part 100b and the head part 100c are $s_1$, $s_2$ and $s_3$, respectively. Here, $s_1+s_2+s_3=s$. A male screw 102 is cut on the outer peripheral surface of the front end part 100a over an area of the length $s_4$ from the front end of the front end part 100a. The male screw 102 is used to fit a nut to restrict the third member 100. The shape of the cross section of the hollow part 101 of the third member 100 is a circle centered in the central axis of the third member 100 in any position. The hollow part 101 comprises a front part 101a with a diameter $D_7$ (here, $D_7$<$D_4$) and a length $s_5$, an intermediate part 101b with a diameter $D_8$ (here, $D_8$<$D_5$) and a length $s_6$ and a rear part 101C with a diameter $D_9$ (here, $D_9$>$D_5$) and a length $s_7$ in order from the front end of the front end part 100a. A V groove-like notch 103 is formed on the outer peripheral surface of the front end part 100a over the whole circumference. The notch angle of the notch 103 is $\Theta$.

As shown in FIG. 22C, the second member 20 has the same constitution as the second member 20 of the first embodiment.

As shown in FIG. 21A, FIG. 21B, FIG. 21C, FIG. 21D and FIG. 21E, the third member 100 is inserted into the hollow part 11 of the first member 10, and the front end of the front end part 100a protrudes from the end surface of the first member 10. And a nut 110 is fitted to the male screw 102 of the front end of the front end part 100a. Furthermore, the axial part 21 of the second member 20 is inserted into the hollow part 101 of the third member 100, and the front end of the axial part 21 protrudes from the end surface of the third member 100. And the nut 30 is fitted to the male screw 23 of the front end of the axial part 21.

The front end part 100a of the third member 100 is accommodated in the first part 11a of the hollow part 11 of the first member 10. A compression coil spring 120 is provided in the intermediate part 100b of the third member 100 on the side of the head part 100c such that it is penetrated by the intermediate part 100b. The compression coil spring 120 is accommodated in the third part 11c of the hollow part 11 of the first member 10 in a compressed state.

A diameter of the compression coil spring 120 is smaller than the diameter $D_3$ of the third part 11c. By a restitutive force applied by the compression coil spring 120 being compressed, one end of the compression coil spring 120 presses a ring-like side surface of a step $S_4$ between the second part 11b and the third part 11c, and the other end of the compression coil spring 120 presses a ring-like end surface $S_5$ of the head part 100c of the third member 100 on the side of the intermediate part 100b. Since the end surface $S_5$ of the head part 100c is pressed by the restitutive force of the compression coil spring 120, the front end part 100a of the third member 100 is pulled on the side of the head part 100c. With this, the front end part of the third member 100 is restricted to the front end part of the first member 10.

The head part 22 of the second member 20 is accommodated in the rear part 101c of the hollow part 101 of the third member 100. The compression coil spring 40 is provided on the part of the axial part 21 of the second member 20 on the side of the head part 22 such that it is penetrated by the axial part 21. The compression coil spring 40 is accommodated in the intermediate part 101b of the hollow part 101 of the third member 100 in a compressed state. The diameter of the compression coil spring 40 is smaller than the diameter $D_8$ of the intermediate part 101b. By a restitutive force applied by the compression coil spring 40 being compressed, one end of the compression coil spring 40 presses a ring-like side surface of a step $S_6$ between the front part 101a and the intermediate part 101b, and the other end of the compression coil spring 40 presses the ring-like end surface $S_2$ of the head part 22 of the second member 20 on the side of the axial part 21. Since the end surface $S_2$ of the head part 22 is pressed by the restitutive force of the compression coil spring 40, the axial part 21 of the second member 20 is pulled on the side of the head part 22. With this, the front end part of the second member 20 is restricted to the front end part of the third member 100.

Sizes (L, $L_1 \sim L_4$, l, $l_1$, $l_2$, s, $s_1 \sim s_7$, D, $D_1 \sim D_9$, d, $d_1$, $d_2$, θ, Θ, etc.) of each part of the failure detection sensor are selected depending on the structure to which the failure detection sensor is attached etc. as needed.

Materials of the first member 10 are selected depending on materials of structural members of the structure to be detected its failure by the failure detection sensor etc. as needed, and is, for example, steel. The second member 20 and the third member 100 are made of materials with fracturing characteristics such that they fractures during elastic deformation or plastic deformation of the first member 10, for example, brittle materials such as cast iron, glass, ceramics, plastics, concrete, etc.

[Method of Controlling Failure Sensitivity of the Failure Detection Sensor]

The failure sensitivity (permissible deformation amount) of the failure detection sensor can be set in two stages. That is, first, the first stage failure sensitivity can be controlled by the shape and notch length (depth) of the notch 24 of the second member 20, in other words, the notch angle θ of the tip of the notch 24 and the diameter d of the axial part 21 at the tip of the notch 24, and the distance t between a side surface of a step $S_7$ of the third member 100 and the end surface $S_2$ of the second member 20. The second stage failure sensitivity can be controlled by the shape and notch length (depth) of the notch 103 of the third member 100, in other words, the notch angle Θ of the tip of the notch 103, the notch length and the diameter $D_4$ of the front end part 100a, and the distance $t_3$ between the side surface of a step $S_1$ of the first member 10 and a side surface of a step $S_8$ of the third member 100. Here, in FIG. 21A, FIG. 21B, FIG. 21C, FIG. 21D and FIG. 21E, a case where $t=t_3=0$ is shown.

[Method of Using the Failure Detection Sensor]

As the same as the first embodiment, the failure detection sensor is inserted into the through hole 53 formed in the structural members 51, 52 to be detected failure and fixed.

When the structural members 51, 52 are given a tensile load which separates them and the tensile load becomes large to some extent, first, the side surface of a step $S_1$ (the press surface) of the first member 10 comes in contact with the side surface of a step $S_8$ (the surface to be pressed) of the third member 100 and begins to press it. With this, the side surface of a step $S_7$ of the third member 100 begins to press the end surface $S_2$ of the second member 20. When the tensile load becomes further large, the second member 20 fractures at the notch 24 which is a stress concentration site, and is divided into two pieces. At this time, since the fractured piece 70 which corresponds to a part of the second member 20 on the side of the head part 22 from the fractured part becomes free from mechanical restriction by the third member 100 at one end of the second member 20, the head part 22 of the second member 20 moves inside the rear part 101c of the hollow part 101 of the third member 100 outward by the restituitive force of the compression coil spring 40, and protrudes outward. When the tensile load becomes still large, the side surface of a step $S_1$ (the press surface) of the first member 10 presses the side surface of a step $S_8$ (the surface to be pressed) of the third member 100 more strongly. When the tensile load becomes large to some extent, the third member 100 fractures at the notch 103 which is a stress concentration site, and is divided into two pieces. At this time, since the fractured piece which corresponds to a part of the third member 100 on the side of the head part 100c from the fractured part becomes free from mechanical restriction by the first member 10 at one end of the third member 100, the head part 100c of the fractured piece moves inside the third part 11c of the hollow part 11 of the first member 10 outward by the restitutive force of the compression coil spring 120, and protrudes outward.

It is easy to recognize visually from the outside, for example, that the head part 22 of the fractured piece 70 and the head part 100c of the fractured piece formed by fracture of the third member 100 protrude outside the first member 10. From the result, it is possible to decide in two stages that there is the risk of the fracture since the structural members 51, 52 are given the tensile load.

According to the seventh embodiment, the same advantages as the sixth embodiment can be obtained.

8. The Eighth Embodiment

[Failure Detection Sensor]

Figure 23:
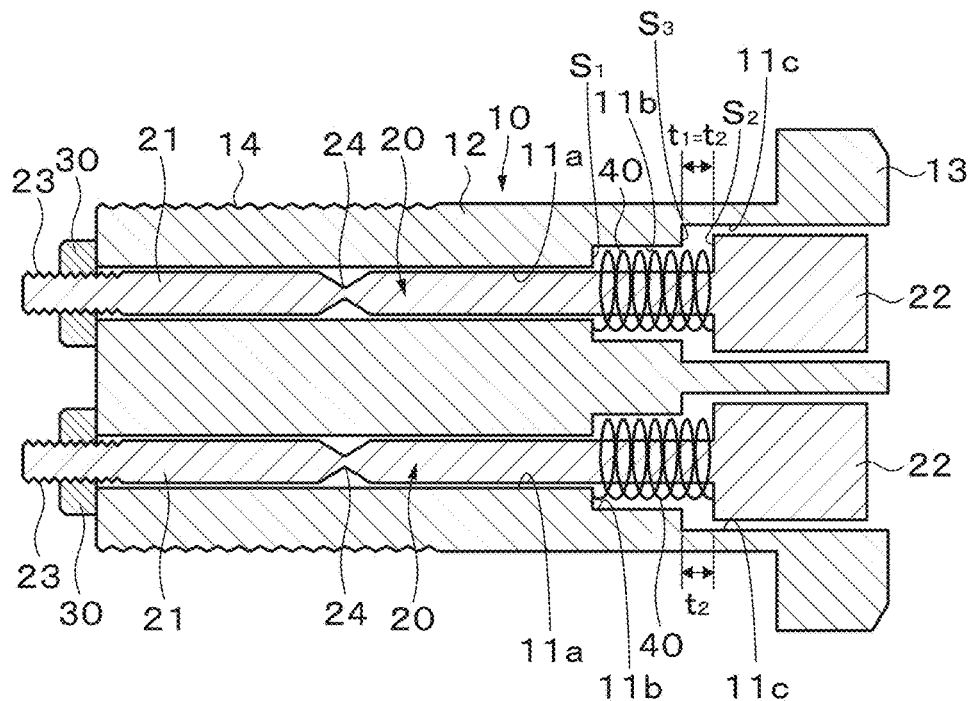
FIG. 23 A longitudinal sectional view showing a failure detection sensor according to the eighth embodiment of the invention.

FIG. 23 shows the failure detection sensor according to the eighth embodiment. The failure detection sensor has substantially the same constitution as the failure detection sensor according to the sixth embodiment. However, $t_1$ of the upper failure detection sensor and $t_2$ of the lower failure detection sensor are selected to be equal, and instead, the second member 20 of the lower failure detection sensor is made to have fracturing characteristics such that it is easy to be fractured as compared with the second member 20 of the upper failure detection sensor. More specifically, materials of the second member 20 and the notch angle θ or depth of the notch 24 of the upper failure detection sensor and the lower failure detection sensor are selected such that the second member 20 of the lower failure detection sensor is easy to be fractured as compared with the second member 20 of the upper failure detection sensor. For example, when materials of the second member 20 and the notch angle θ of the notch 24 of the upper failure detection sensor and the lower failure detection sensor are the same each other, the depth of the notch 24 of the second member 20 of the lower failure detection sensor is set to be large as compared with the depth of the notch 24 of the second member 20 of the upper failure detection sensor. Other than the above is the same as the failure detection sensor according to the sixth embodiment.

[Method of Using the Failure Detection Sensor]

The method of using the failure detection sensor is the same as the failure detection sensor according to the sixth embodiment.

According to the eighth embodiment, the same advantages as the sixth embodiment can be obtained.

9. The Ninth Embodiment

[Failure Detection Sensor]

Figure 24:
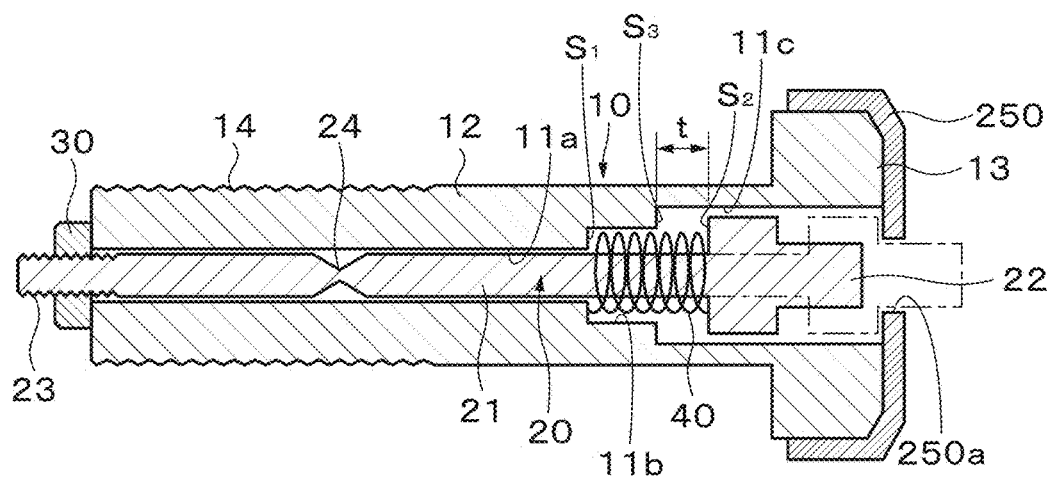
FIG. 24 A longitudinal sectional view showing a failure detection sensor according to the ninth embodiment of the invention.

FIG. 24 shows the failure detection sensor according to the ninth embodiment. The failure detection sensor has substantially the same constitution as the failure detection sensor according to the first embodiment. However, the failure detection sensor is different from the failure detection sensor according to the first embodiment in that the head part 22 of the second member 20 has a two-stage structure with different diameters and the diameter of its front end part is small, and a cap 250 is attached to the head part 13 of the first member 10. Provided at the center of the cap 250 is a hole 250*a* with a diameter a little larger than the diameter of the front end part of the head part 22 of the second member 20 and smaller than the diameter of the part of the head part 22 except the front end part (root part). Other than the above is the same as the failure detection sensor according to the first embodiment.

[Method of Using the Failure Detection Sensor]

A method of using the failure detection sensor is the same as the failure detection sensor according to the first embodiment. As the same as the first embodiment, when the failure detection sensor is attached to the through hole 53 formed in the structural members 51, 52, if the structural members 51, 52 are given a tensile load, the side surface of a step $S_3$ of the first member 10 finally comes in contact with the end surface $S_2$ of the head part 22 of the second member 20, and begins to press it. And when the second member 20 fractures at last, as shown by a dot and space line in FIG. 24, the head part 22 of the fractured piece 70 moves and its front end part protrudes outward from the hole 250*a* of the cap 250. In this case, since the diameter of the root of the head part 22 is larger than the diameter of the hole 250*a* of the cap 250, when the root of the head part 22 comes in contact with the inner surface of the cap 250, movement of the head part 22 stops.

According to the ninth embodiment, the same advantages as the first embodiment can be obtained.

10. The Tenth Embodiment

[Failure Detection Sensor]

FIG. 25 shows the failure detection sensor according to the tenth embodiment. The failure detection sensor has substantially the same constitution as the failure detection sensor according to the first embodiment. However, the length of the male screw 14 cut on the outer peripheral surface of the axial part 12 of the first member 10 is large as compared with that of the failure detection sensor according to the first embodiment. Other constitution is the same as the first embodiment.

[Method of Using the Failure Detection Sensor]

As shown in FIG. 25, in the tenth embodiment, a circular through hole 53 with a diameter slightly larger than the diameter D of the axial part 12 of the first member 10 of the failure detection sensor is formed in the structural members 51, 52 constituting the structure to be detected failure and a female screw 51*a* which can be screwed by the male screw 14 of the axial part 12 of the first member 10 is cut on the inner peripheral surface of the through hole 53 of one of the structural members 51, 52, for example, the structural member 51. And the axial part 12 of the first member 10 is inserted into the through hole 53, and then the male screw 14 of the axial part 12 is screwed into the female screw 51*a* of the structural member 51 by rotating the head part 13 with a hexagonal spanner etc. until the head part 13 comes in contact with the structural member 52. Fastening is carried out with enough fastening torque so that the failure detection sensor is securely fixed to the structural members 51, 52.

As the same as the first embodiment, the second member 20 fractures when the tensile load larger than a certain value is given to the structural members 51, 52.

According to the tenth embodiment, the same advantages as the first embodiment can be obtained.

11. The Eleventh Embodiment

[Failure Detection Sensor]

Figure 26A:
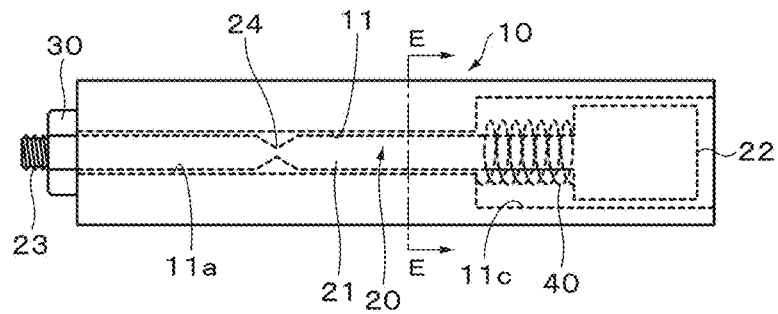
FIG. 26A A front view showing a failure detection sensor according to the eleventh embodiment of the invention.
Figure 26B:
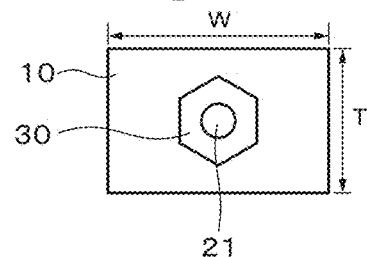
FIG. 26B A left side view showing the failure detection sensor according to the eleventh embodiment of the invention.
Figure 26C:
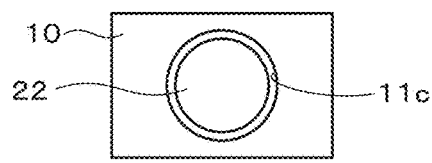
FIG. 26C A right side view showing the failure detection sensor according to the eleventh embodiment of the invention.
Figure 26D:
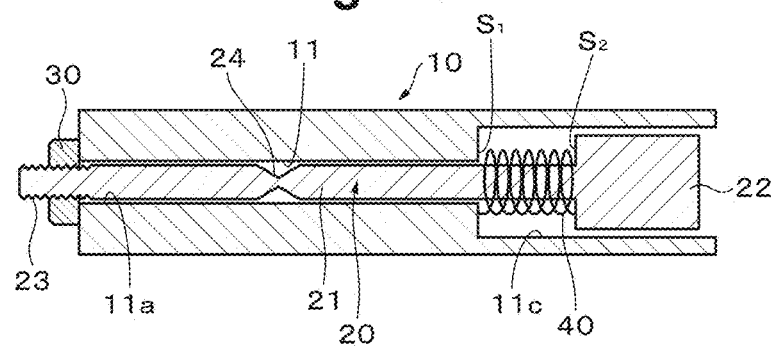
FIG. 26D A longitudinal cross sectional view showing the failure detection sensor according to the eleventh embodiment of the invention.
Figure 26E:
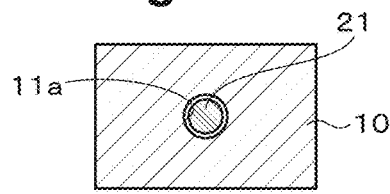
FIG. 26E A cross sectional view showing the failure detection sensor according to the eleventh embodiment of the invention.
Figure 27A:
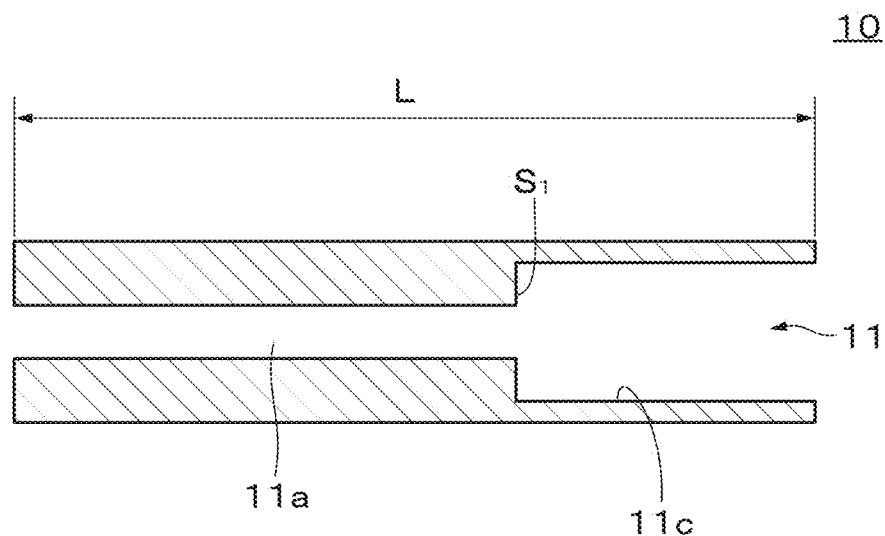
FIG. 27A A longitudinal cross sectional view showing the first member constituting the failure detection sensor according to the eleventh embodiment of the invention.
Figure 27B:
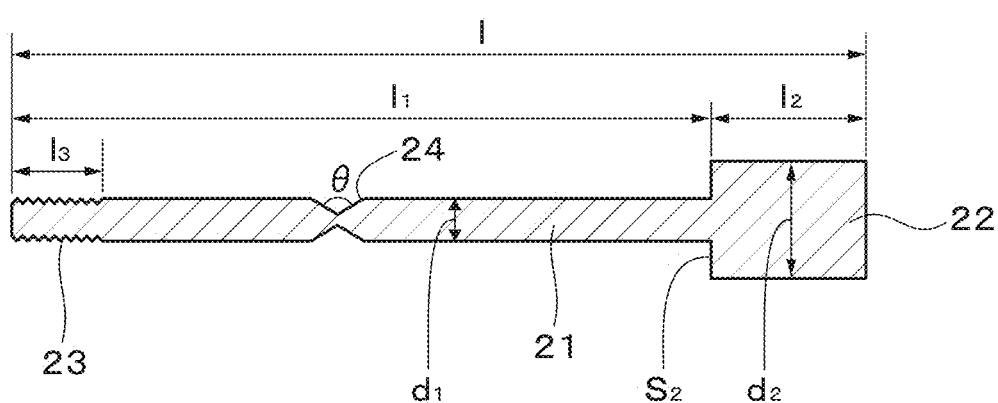
FIG. 27B A longitudinal cross sectional view showing the second member constituting the failure detection sensor according to the eleventh embodiment of the invention.

FIG. 26A, FIG. 26B, FIG. 26C, FIG. 26D and FIG. 26E show the failure detection sensor according to the eleventh embodiment, where FIG. 26A is a front view, FIG. 26B is a left side view, FIG. 26C is a right side view, FIG. 26D is a longitudinal cross sectional view and FIG. 26E is a cross sectional view along the E-E line of FIG. 26A. FIG. 27A shows details of the first member 10, and FIG. 27B shows details of the second member 20. The failure detection sensor is especially suitable for detection of bend fracture, torsion fracture, shear fracture and compression fracture.

As shown in FIG. 26A, FIG. 26B, FIG. 26C, FIG. 26D, FIG. 26E, FIG. 27A and FIG. 27B, the failure detection sensor is different from the failure detection sensor according to the first embodiment in that the first member 10 has a quadratic prism-like shape, not a bolt-like shape, and the hollow part 11 of the first member 10 is composed of only the first part 11*a* and the third part 11*c*. In this case, the compression coil spring 40 is accommodated in the third part 11*c*. Other constitution is the same as the failure detection sensor according to the first embodiment.

[Method of Controlling Failure Sensitivity of the Failure Detection Sensor]

The method of controlling the failure sensitivity (permissible deformation amount) of the failure detection sensor is the same as the fifth embodiment.

[Method of Using the Failure Detection Sensor]

Figure 28A:
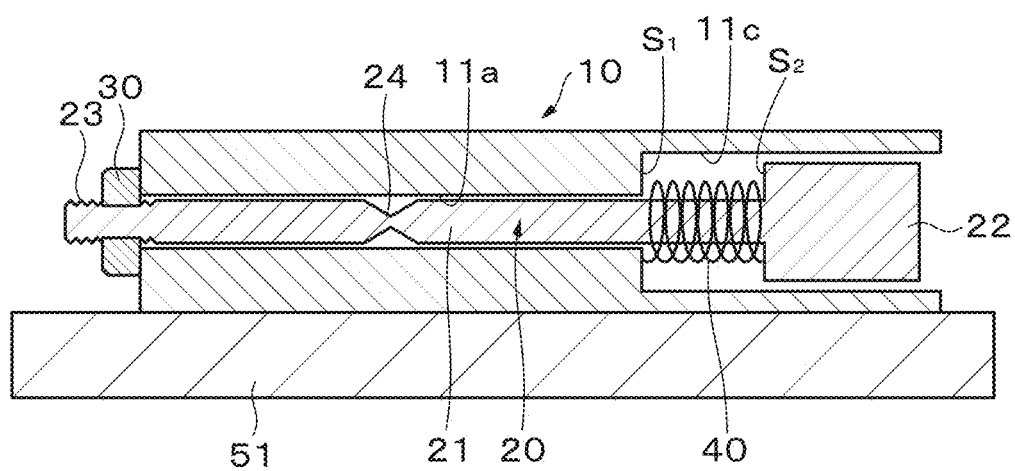
FIG. 28A A longitudinal cross sectional view showing a state in which the failure detection sensor according to the eleventh embodiment of the invention is attached to the structure.
Figure 28B:
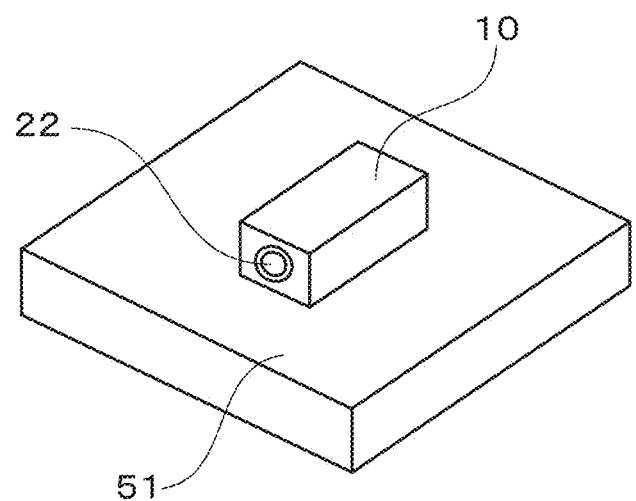
FIG. 28B A perspective view showing the state in which the failure detection sensor according to the eleventh embodiment of the invention is attached to the structure.

Described as an example is a case where the failure detection sensor is applied for detection of bend fracture. However, the failure detection sensor can also be applied to detection of torsion fracture, shear fracture or compression fracture. As shown is FIG. 28A and FIG. 28B, the failure detection sensor is attached to the structural member 51 to be detected failure and fixed. As an attaching method of the failure detection sensor various methods can be used as far as the failure detection sensor can be fixed with the strength enough to suppress detachment of the failure detection sensor from the structural member 51 when mechanical deformation of the structural member 51 occurs. The attaching method is, for example, screw clamp, welding, etc.

Figure 29A:
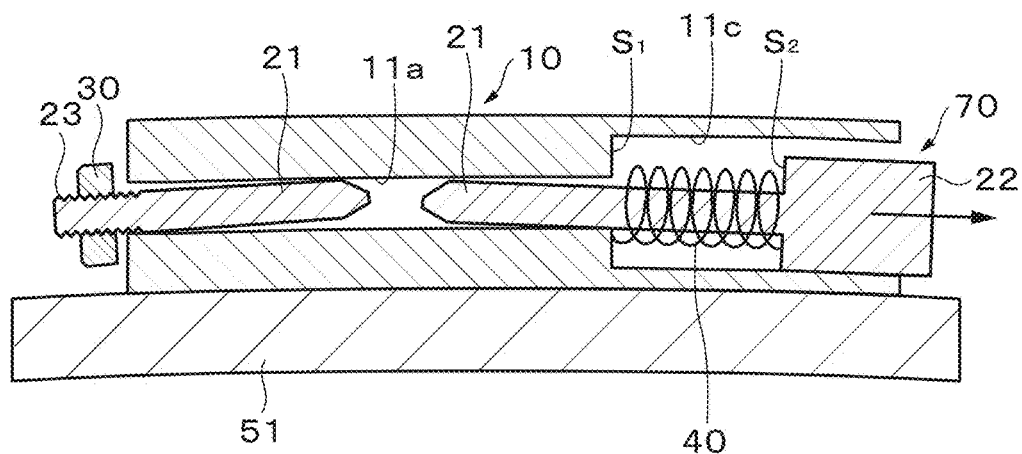
FIG. 29A A longitudinal cross sectional view showing a state in which a strong bending moment acts on the structure to which the failure detection sensor according to the eleventh embodiment of the invention is attached.
Figure 29B:
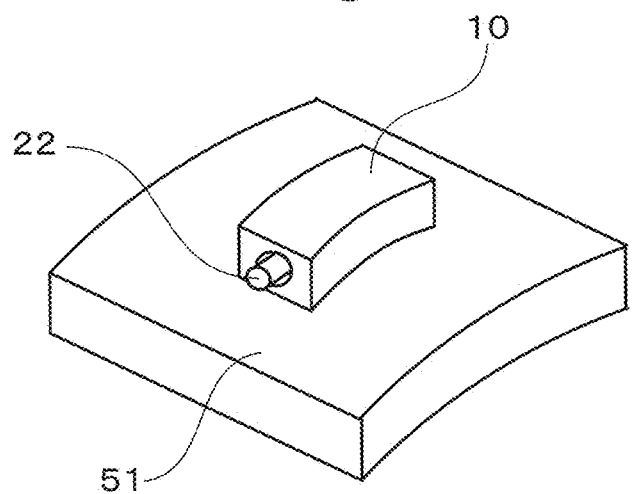
FIG. 29B A perspective view showing the state in which a strong bending moment acts on the structure to which the failure detection sensor according to the eleventh embodiment of the invention is attached.

Described is now a case where the structural member 51 is given a bending moment which bends the structural member 51 upward. When the structural member 51 is given a bending moment, the structural member 51 is bent upward, and finally, the first member 80 is also bent upward. When the structural member 51 is given a larger bending moment, the structural member 51, and thus the first member 10 is bent more. When the degree of bending reaches a certain level, as shown in FIG. 29A and FIG. 29B, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 10 at one end of the second member 20. As a result, the head part 22 of the fractured piece 70 moves outward inside the third part 11c of the hollow part 11 of the first member 10 by the restituitive force of the compression coil spring 40, and protrudes outward. In this case, since the notch 24 is formed over the whole circumference of the second member 20, the part of the notch 24 of the second member 20 securely fractures without depending on direction of bending of the first member 10 and how the second member 20 is bent.

It is easy to recognize visually from the outside, for example, that the head part 22 of the fractured piece 70 protrudes outside the first member 10 as described above. From the result, it is possible to decide that there is the risk of the failure since the structural member 51 is given the bending moment.

As described above, according to the eleventh embodiment, the same advantages as the first embodiment can be obtained with respect to bend fracture, torsion fracture, shear fracture or compression fracture.

12. The Twelfth Embodiment

[Failure Detection Sensor]

Figure 30:
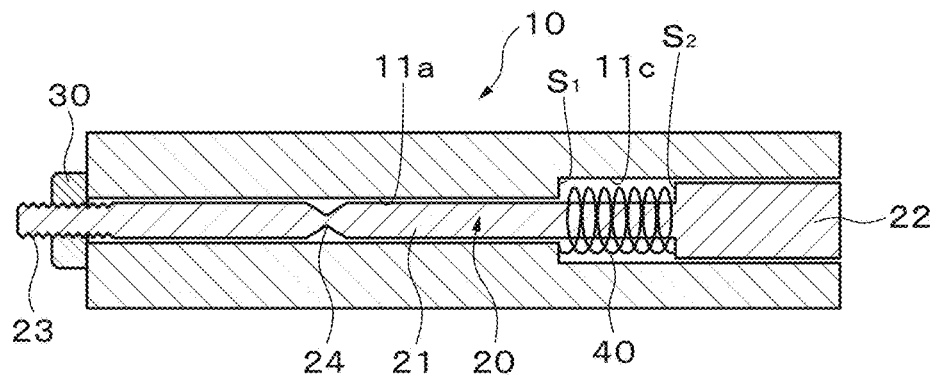
FIG. 30 A longitudinal cross sectional view showing a failure detection sensor according to the twelfth embodiment of the invention.
Figure 31A:
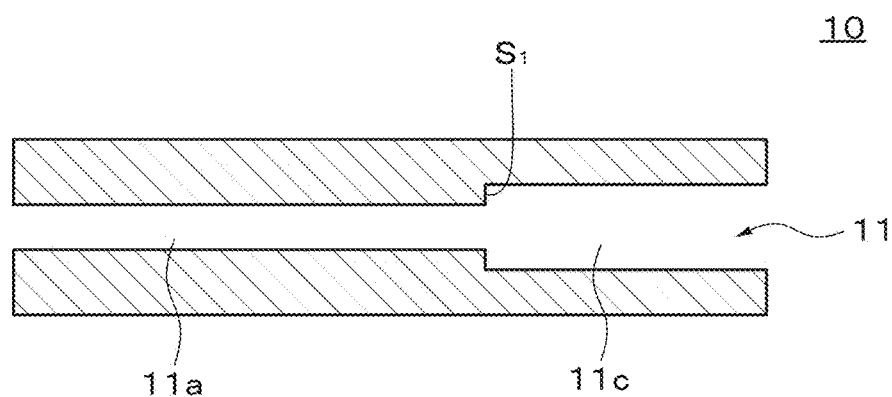
FIG. 31A A longitudinal cross sectional view showing the first member constituting the failure detection sensor according to the twelfth embodiment of the invention.
Figure 31B:
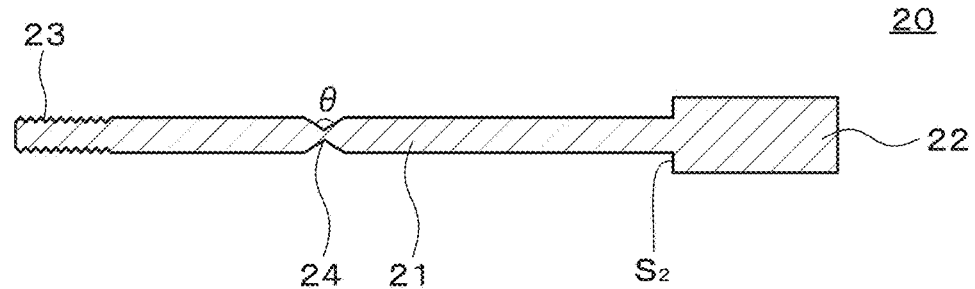
FIG. 31B A longitudinal cross sectional view showing the second member constituting the failure detection sensor according to the twelfth embodiment of the invention.

FIG. 30 shows the failure detection sensor according to the twelfth embodiment. FIG. 31A shows details of the first member 10, and FIG. 31B shows details of the second member 20. The failure detection sensor is especially suitable for detection of compression fracture.

As shown in FIG. 30, FIG. 31A and FIG. 31B, the failure detection sensor is different from the failure detection sensor according to the first embodiment in that the first member 10 has a cylinder-like shape, not a bolt-like shape, and the hollow part 11 of the first member 10 is composed of only the first part 11a and the third part 11c. In this case, the compression coil spring 40 is accommodated in the third part 11c. Other constitution is the same as the failure detection sensor according to the first embodiment.

[Method of Controlling Failure Sensitivity of the Failure Detection Sensor]

The method of controlling the failure sensitivity (permissible deformation amount) of the failure detection sensor is the same as the fifth embodiment.

[Method of Using the Failure Detection Sensor]

Figure 32A:
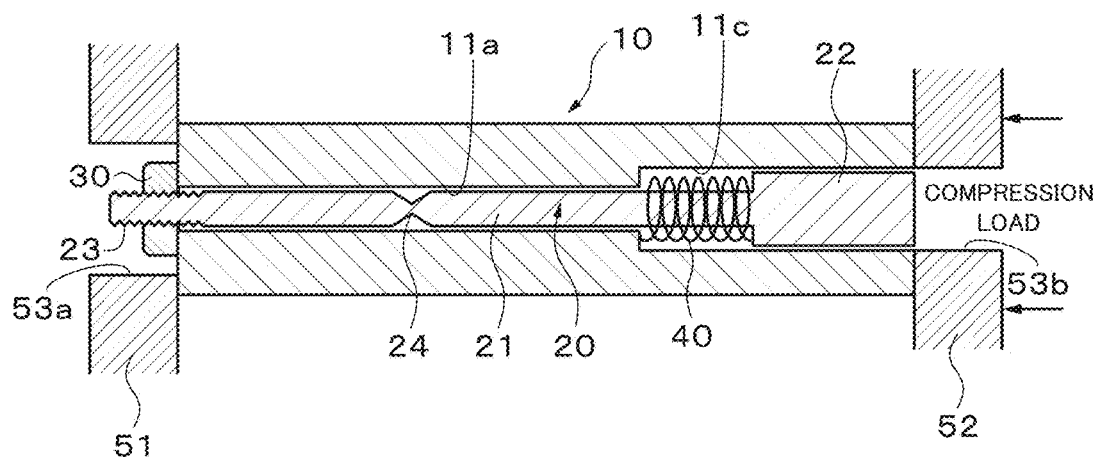
FIG. 32A A cross sectional view showing a state in which the failure detection sensor according to the twelfth embodiment of the invention is attached to junctions of the structure.
Figure 32B:
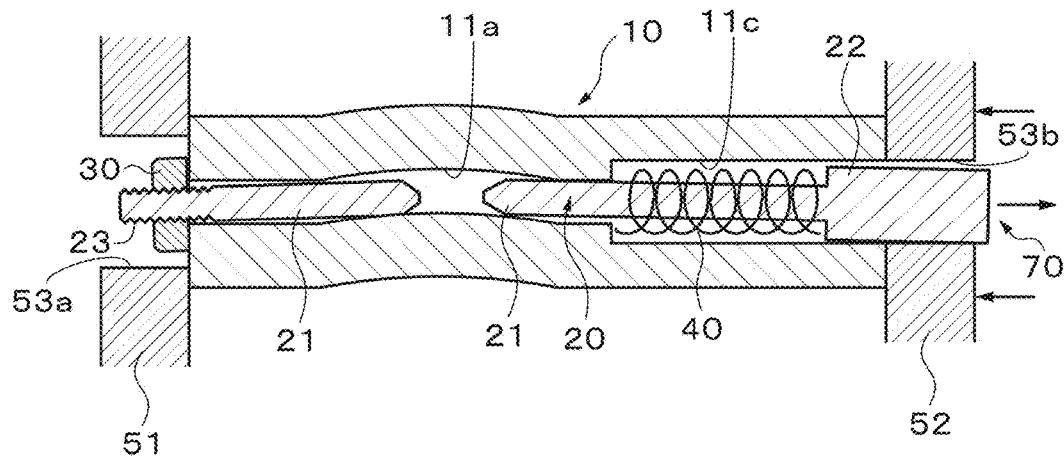
FIG. 32B A cross sectional view showing a state in which a strong compression load is applied to the structure to which the failure detection sensor according to the twelfth embodiment of the invention is attached.

Described is a case where the failure detection sensor is applied for detection of compression fracture. As shown in FIG. 32A and FIG. 32B, the failure detection sensor is placed between the structural members 51, 52 to be detected failure such that its central axis is perpendicular to the structural members 51, 52, and both edges of the failure detection sensor are sandwiched between the structural members 51, 52. Through holes 53a, 53b are formed coaxially in the structural members 51, 52, respectively. Assume that the structural member 51 is fixed to another part of the structure and the structural member 52 is not fixed. The diameter of the through hole 53a is selected to be sufficiently smaller than the diameter D of the first member 10 and sufficiently larger than the size of the nut 30. The diameter of the through hole 53b is selected to be sufficiently smaller than the diameter D of the first member 10 and equal to or larger than the diameter $D_3$ of the third part 11c of the first member 10, and here it is selected to be equal to the diameter $D_3$. The peripheral part of the through hole 53a of the structural member 51 is in contact with one end surface of the first member 10 of the failure detection sensor and the peripheral part of the through hole 53b of the structural member 52 is in contact with the other end surface of the first member 10 of the failure detection sensor.

As shown in FIG. 32A, described now is a case where the structural member 52 is given a compression load. When the structural member 52 is given the compression load, the first member 10 of the failure detection sensor is also given the compression load. When the compression load given to the structural member 52 becomes large to some extent, as shown in FIG. 32B, the first member 10 results in buckling and produces bend deformation. As a result, the second member 20 also produces bend deformation. When bend deformation becomes large to some extent, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 10 at one end of the second member 20. As a result, the head part 22 of the fractured piece 70 moves outward inside the third part 11c of the hollow part 11 of the first member 10 by the restitutive force of the compression coil spring 40, and protrudes outward. In this case, since the notch 24 is formed over the whole circumference of the second member 20, the part of the notch 24 of the second member 20 securely fractures without depending on direction of bending of the first member 10 and how the second member 20 is bent.

It is easy to recognize visually from the outside, for example, that the head part 22 of the fractured piece 70 protrudes outside the first member 10 as described above. From the result, it is possible to decide that there is the risk of the failure since the structural member 52 is given the compression load.

As described above, according to the twelfth embodiment, the same advantage as the first embodiment can be obtained with respect to compression fracture, bend fracture, shear fracture or torsion fracture of the structure.

13. The Thirteenth Embodiment

[Failure Detection Sensor]

Figure 33:
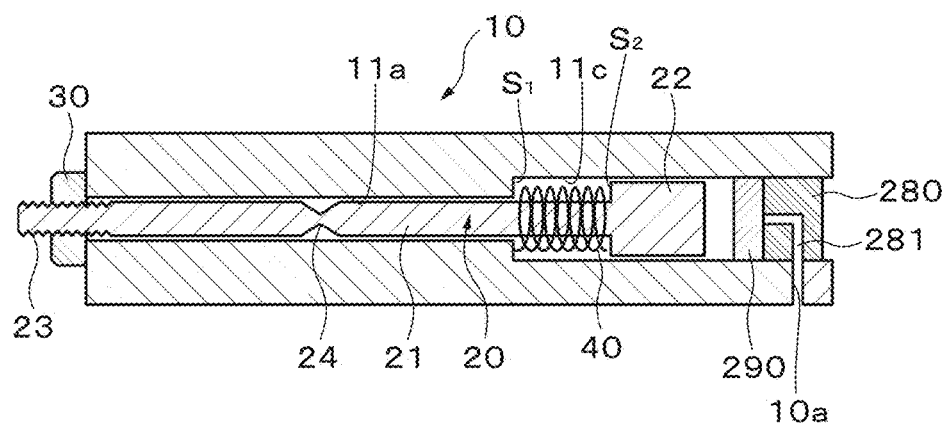
FIG. 33 A longitudinal cross sectional view showing a failure detection sensor according to the thirteenth embodiment of the invention.
Figure 34A:
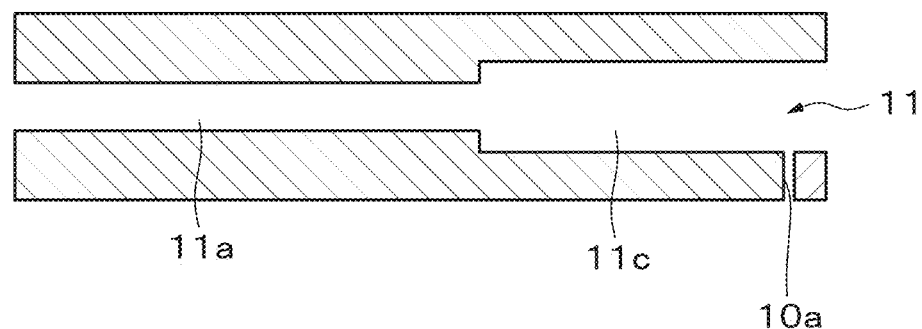
FIG. 34A A longitudinal cross sectional view showing the first member constituting the failure detection sensor according to the thirteenth embodiment of the invention.
Figure 34B:
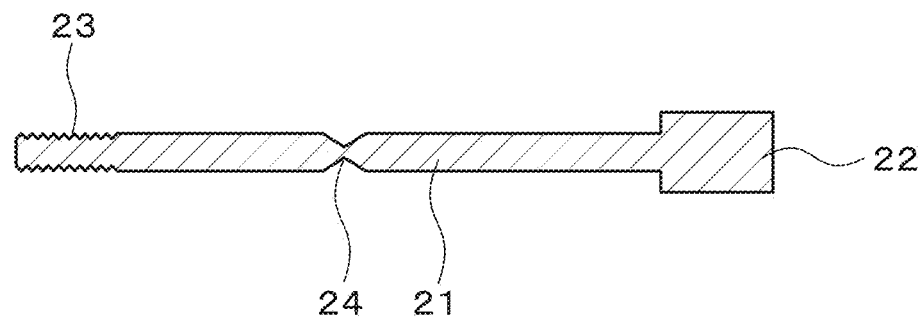
FIG. 34B A longitudinal cross sectional view showing the second member constituting the failure detection sensor according to the thirteenth embodiment of the invention.

FIG. 33 shows the failure detection sensor according to the thirteenth embodiment. FIG. 34A shows details of the first member 10, and FIG. 34B shows details of the second member 20. The failure detection sensor is especially suitable for detection of compression fracture, but can be used for detection of bend fracture, shear fracture or torsion fracture.

As shown in FIG. 33, FIG. 34A and FIG. 34B, the first member 10 and the second member 20 of the failure detection sensor is constituted as substantially the same as the twelfth embodiment. However, the failure detection sensor is different from the twelfth embodiment in that a nozzle 280 is attached to an exit of the third part 11c of the hollow part 11 of the first member 10 so as to stop the exit and a solid colored gel material 290 is attached to one end surface of the nozzle 280 on the side of the head part 22 of the second member 20 so as to face with the head part 22. A through hole 10a which reaches the third part 11c of the hollow part 11 is formed on the outer peripheral part of the first member 10. Formed in the nozzle 280 is an L-shape passage 281 which connects between the center of one end surface of the nozzle 280 on the side of the head part 22 and the through hole 10a on the outer peripheral part of the first member 10. The passage 281 serves as a passage of the gel material 290. Other constitution is the same as the twelfth embodiment.

[Method of Controlling Failure Sensitivity of the Failure Detection Sensor]

The method of controlling the failure sensitivity (permissible deformation amount) of the failure detection sensor is the same as the fifth embodiment.

[Method of Using the Failure Detection Sensor]

Figure 35A:
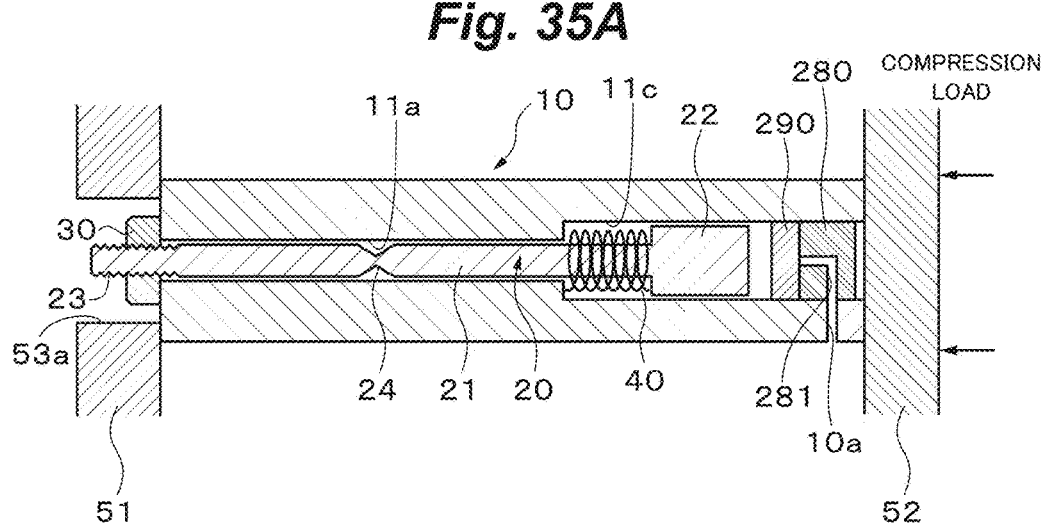
FIG. 35A A cross sectional view showing a state in which the failure detection sensor according to the thirteenth embodiment of the invention is attached to junctions of the structure.
Figure 35B:
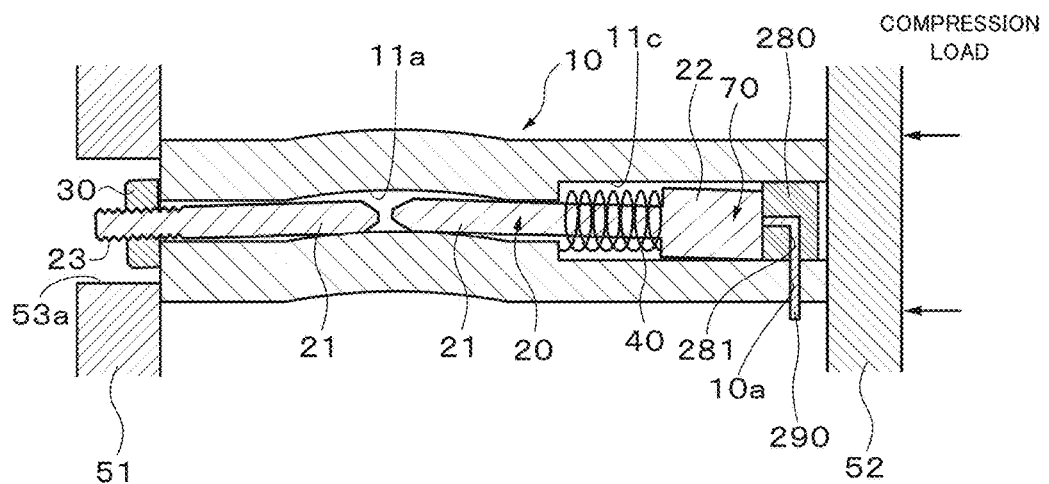
FIG. 35B A cross sectional view showing a state in which a strong compression load is applied to the structure to which the failure detection sensor according to the thirteenth embodiment of the invention is attached.

Described is a case where the failure detection sensor is applied for detection of compression fracture. As shown in FIG. 35A and FIG. 35B, the failure detection sensor is placed between the structural members 51, 52 to be detected failure as the same as the twelfth embodiment. In this case, the through hole 53b is not formed in the structural member 52.

As shown in FIG. 35A, described is a case where the structural member 52 is given a compression load. When the structural member 52 is given the compression load, the first member 10 of the failure detection sensor is also given the compression load. When the compression load given to the structural member 52 becomes large to some extent, as shown in FIG. 35B, the first member 10 results in buckling and produces bend deformation. As a result, the second member 20 also produces bend deformation. When bend deformation becomes large to some extent, the second member 20 fractures at the notch 24 which is a stress concentration site, and is divided into two pieces. At this time, the fractured piece 70 which corresponds to the part of the second member 20 on the side of the head part 22 from the fractured part becomes free from mechanical restriction by the first member 10 at one end of the second member 20. As a result, the head part 22 of the fractured piece 70 moves outward inside the third part 11c of the hollow part 11 of the first member 10 by the restitutive force of the compression coil spring 40. Since the front end of the head part 22 presses the gel material 290, the gel material 290 goes into the passage 281 of the nozzle 280 from its one end and is pushed out from another end, and finally springs out of the through hole 10a of the outer peripheral part of the first member 10.

It is easy to recognize visually from the outside, for example, that the gel material 290 springs out of the first member 10 as described above. From the result, it is possible to decide that there is the risk of the failure since the structural member 52 is given the compression load.

As described above, according to the thirteenth embodiment, the same advantages as the first embodiment can be obtained with respect to detection of compression fracture, bend fracture, shear fracture or torsion fracture of the structure.

14. The Fourteenth Embodiment

[Failure Detection System]

Figure 36:
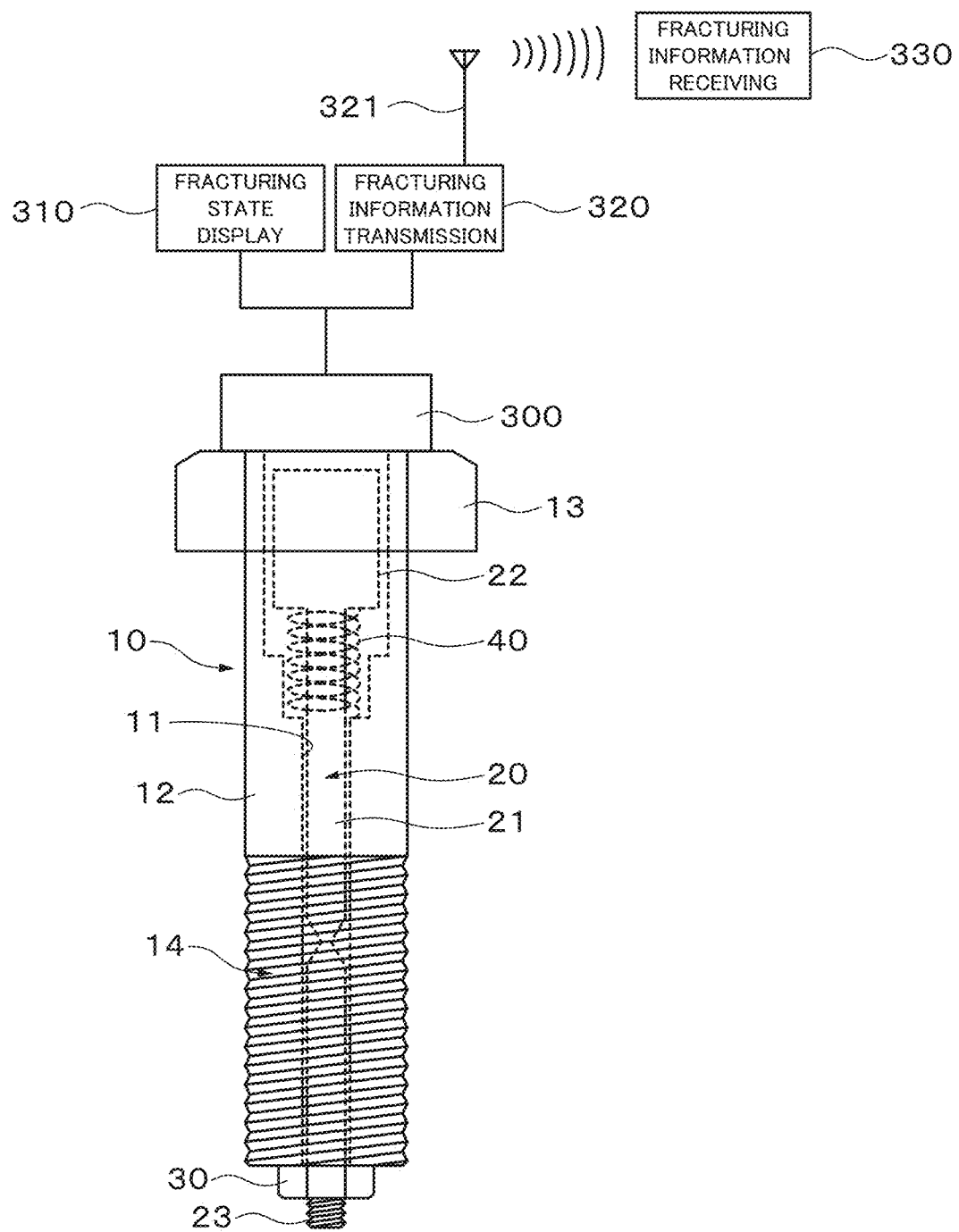
FIG. 36 A schematic view showing a failure detection system according to the fourteenth embodiment of the invention.

FIG. 36 is the failure detection system according to the fourteenth embodiment. The failure detection system uses the failure detection sensor according to the first embodiment.

As shown in FIG. 36, a device for detecting fracture of the second member 300 is attached to the head part 13 of the first member 10 of the failure detection sensor according to the first embodiment. The device for detecting fracture of the second member 300 converts a mechanical signal by fracture of the second member 20 into an electrical conduction or non-conduction signal, and uses it as a fracture signal. More specifically, for example, a closed circuit comprising a power source and a resistor is formed near the front end part of the head part 13 of the first member 10. In this case, wire of the closed circuit is made so that apart of the wire crosses an exit of the third part 11c of the hollow part 11 of the first member 10 in the diameter direction, for example. With this, at first, a current flows in the closed circuit and a voltage between both ends of the resistor is detected. When the front end part of the head part 22 of the fractured piece 70 springs out due to fracture of the second member 20, the head part 22 strikes and cuts the wire. As a result, the closed circuit is made open and no current flows. Therefore, the voltage between both ends of the resistor becomes zero. In this way, by detecting the voltage between both ends of the resistor of the closed circuit, fracture of the second member 20 can be detected. Alternatively, a circuit which connects a power source, a resistor and a push-button switch in series is formed near the front end part of the head part 13 of the first member 10. As the push-button switch, a normally open switch in which a point of contact is closed by pushing, or a normally close switch in which a point of contact opens by pushing. The switch of the circuit is placed such that its manipulation part locates at the front end part of the head part 13. For example, when a normally open switch is used as the switch, the circuit is normally open and no current flows. When the front end of the head part 22 of the fractured piece 70 springs due to fracture of the second member 20, the head part 22 strikes the manipulation part of the switch and closes the point contact of the switch. Therefore, the circuit is closed and a current flows. By detecting the voltage between both ends of the resistor of the closed circuit, fracture of the second member 20 can be detected. Alternatively, at least a part of the head part 22 of the second member 20, for example, the front end part is formed by permanent magnet made of ferromagnetic substance and a coil larger the head part 22 is placed near the front end part of the head part 13 of the first member 10, for example, in parallel with the front end surface of the head part 13. In this case, when the head part 22 of the fractured piece 70 springs out due to fracture of the second member 20, the head part 22 penetrates the coil to increase magnetic flux which penetrates the coil. As a result, a current (induced current) flows in the coil so as to prevent the magnetic flux increasing. Therefore, by detecting the induced current or induced electromotive force, fracture of the second member 20 can be detected and a fracture signal can be easily taken out. Depending on the situation, an electromagnet may be placed at the front end part of the head part 22 instead of forming at least a part of the head part 22 with permanent magnet.

The fracture signal detected by the device for detecting fracture of the second member 300 is transmitted to a fracturing state display device 310 and a fracturing information transmitter 320, respectively. The fracturing state display device 310 and the fracturing information transmitter 320 may be placed near the device for detecting fracture of the second member 30 or may be placed at a place apart from the device for detecting fracture of the second member 300. Transmission of the fracture signal to the fracturing state display device 310 and the fracturing information transmitter 320 may be carried out by wired communication or wireless communication. On reception of the fracture signal, the fracturing state display device 310 displays massages, images, etc. showing fracture of the second member 20, or lights or blinks a lamp, for example. On display, an alarm sound may be made simultaneously to call attention. On reception of the fracture signal, the fracturing information transmitter 320 transmits the fracture signal to the outside from an antenna 321. The fracture signal transmitted from the antenna 321 is received by a receiving set 330 placed outside. As the receiving set 330, for example, a personal computer with a receiving function can be used.

[Method of Using the Failure Detection System]

As the same as the first embodiment, the failure detection sensor is attached to the through hole 53 formed in the structural members 51, 52 of the structure to be detected failure. The fracturing state display device 310, the fracturing information transmitter 320 and the receiving set 330 are placed at the appointed places.

When the second member 20 of the failure detection sensor fractures by the tensile load given to the structural members 51, 52, the fracture signal is detected by the device for detecting fracture of the second member 300. The fracture signal is transmitted to the fracturing state display device 310. The fracturing state display device 310 to which the fracture signal is transmitted displays, for example, a message "risk of failure" with an alarm sound as needed, and further, blinks the message, lights or blinks a lamp as needed to call the administrator of the structure to attention. The administrator who saw the message displayed on the fracturing state display device 310 or lighting or blinking of the lamp can examine the state of the structural members 51, 52 and take necessary measures. The fracturing information transmitter 320 to which the fracture signal is transmitted transmits the fracture signal to the outside from the antenna 321. In this case, when the receiving set 330 receives the fracture information transmitted from the antenna 321, the administrator can go to the place of the structure and examine the state of the structural members 51, 52 to take necessary measures.

According to the fourteenth embodiment, in addition to the same advantages as the first embodiment, it is possible to obtain an additional advantage that it is easy to detect failure of the structural members 51, 52 from the place apart from the structure.

15. The Fifteenth Embodiment

[Failure Detection Sensor]

Figure 37:
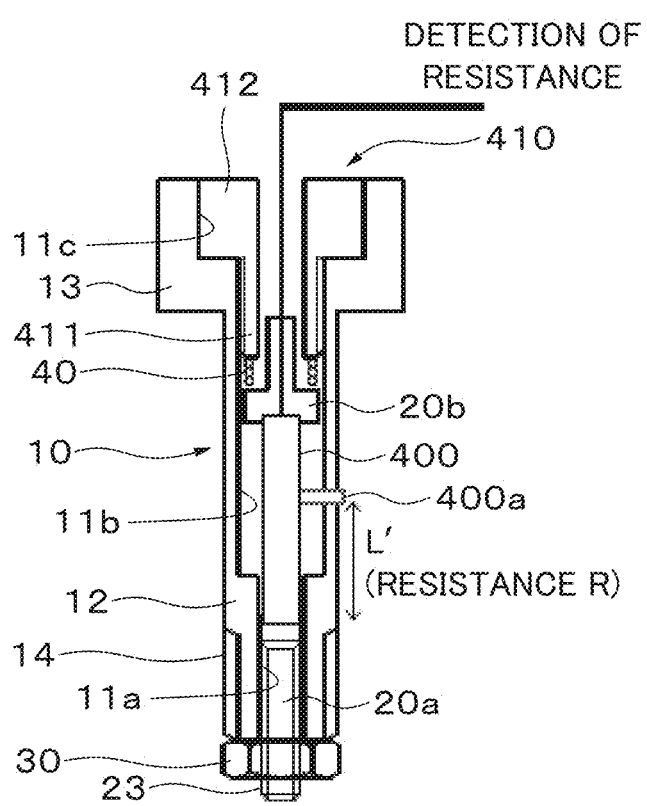
FIG. 37 A schematic view showing a failure detection sensor according to the fifteenth embodiment of the invention.

FIG. 37 shows the failure detection sensor according to the fifteenth embodiment. As shown in FIG. 37, the failure detection sensor comprises the hexagonal bolt-like first member 10 with the hollow part 11 and the circular rod-like second member 20 which is inserted into the hollow part 11 of the first member 10 and constituted by a frontal part 20a and a rear part 20b which are placed so as to sandwich a potentiometer 400. A movable part 400a of the potentiometer 400 is fitted into a through hole formed in the first member 10, and forms one body together with the first member 10.

As shown in FIG. 37, the first member 10 is constituted as the same as the first member 10 of the failure detection sensor according to the first embodiment.

A spring receiver 410 with a bolt-like shape as a whole is attached to the second part 11b and the third part 11c of the hollow part 11 of the first member 10. A male screw is cut on the outer peripheral surface of an axial part 411 of the spring receiver 410, and the male screw is screwed into a female screw cut on the inner peripheral surface of the second part 11b, so that the spring receiver 410 is attached to the first member 10. A head part 412 of the spring receiver 410 is accommodated in the third part 11c of the hollow part 11 of the first member 10. The compression coil spring 40 is attached in a space between the front end of the axial part 411 of the spring receiver 410 and the front end part of the rear part 20b of the second member 20 such that the compression coil spring 40 is penetrated by the rear part 20b and compressed. The frontal part 20a of the second member 20 is inserted into the first part 11a of the hollow part 11 of the first member 10, and protrudes from the end surface of the first member 10. And the nut 30 is fitted to the male screw 23 of the front end of the frontal part 20a.

Materials of the first member 10 are selected, for example, as the same as the first embodiment. Materials of the second member 20 are not particularly limited and selected as needed, for example, as the same as the first embodiment.

[Method of Using the Failure Detection Sensor]

As the same as the first embodiment, the failure detection sensor is inserted into the through hole 53 formed in the structural members 51, 52 to be detected failure and fixed. A length between one end of the potentiometer 400 and the movable part 400a in this state is denoted as L' and a resistance measured by the potentiometer 400 at this time is denoted as R.

Figure 38:
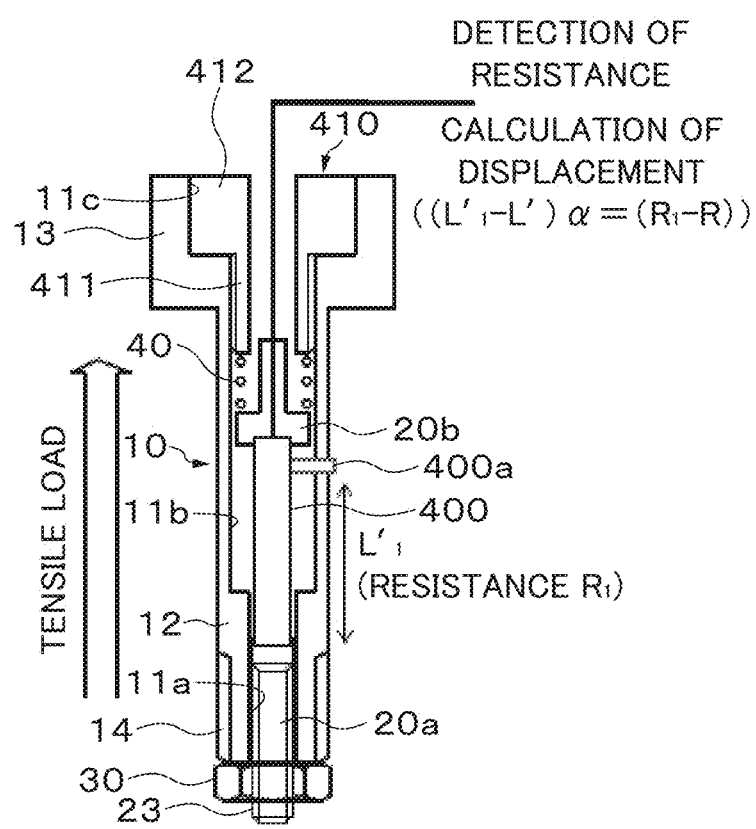
FIG. 38 A schematic view for explaining the operation of the failure detection sensor according to the fifteenth embodiment of the invention.

As shown in FIG. 38, when the structural members 51, 52 are given a tensile load, the first member 10 is also given the tensile load and the axial part 12 is elongated. Suppose that the axial part 12 is elongated, and thus the length between one end of the potentiometer 400 and the movable part 400a becomes $L'_1$. A resistance measured by the potentiometer 400 at this time is denoted as $R_1$. In this time, displacement of the head part 13 of the first member 10, $L'_1 - L'$ is obtained as $(L'_1 - L')\alpha = R_1 - R$. Here, $\alpha$ is a proportional coefficient.

When the displacement $L'_1 - L'$ of the head part 13 of the first member 10 exceeds the predetermined permissible value, it can be decided that there is the risk of the failure since the structural members 51, 52 are given the tensile load. The displacement of the head part 13 can be measured by observing location of the movable part 400a from the outside of the first member 10.

According to the fifteenth embodiment, it is possible to detect the displacement produced by elastic deformation or plastic deformation of the first member 10 as a change of the resistance, and thus detect tensile fracture.

Described now are specific examples of usage of the failure detection sensor according to the first to the fifteenth embodiments.

(1) Examples of Usage of the Failure Detection Sensor for Detecting Tensile Fracture For example, under a viaduct of the road, steel plates are placed on the base and the side of the foundation of the road, and steel plates for reinforcement are fixed to the steel plates with bolts or rivets to realize reinforcement. In this case, a tensile force is applied between the steel plates and there is a fear that tensile fracture results due to deterioration depending on time caused by a long time use. In such a case, as far as the necessary strength is obtained, instead of at least one bolt or rivet, one of the above-mentioned failure detection sensors is attached to a through hole formed in both steel plates and failure is detected. Alternatively, leaving bolts or rivets as it is, a through hole for attachment of the failure detection sensor is formed in a part of both steel plates except the bolts or the rivets and the failure detection sensor is attached to the through hole.

Furthermore, for example, in a factory, there is a case that H-type steels are spanned horizontally under the ceiling to support it and in this case, two H-type steels are joined together. In this case, steel plates for reinforcement are often joined to the upper surface, the lower surface and the side surface of the H-type steels with bolts and nuts such that they straddle on the two H-type steel plates. In this case, since the tensile force is applied between steel plates, there is a fear that tensile fracture results due to deterioration depending on time caused by a long time use. In such a case, as far as the necessary strength is obtained, instead of at least one bolt, one of the above-mentioned failure detection sensors is attached to a through hole formed in both steel plates and failure is detected. Alternatively, leaving bolts as it is, a through hole for attachment of the failure detection sensor is formed in apart of both steel plates except the bolt and the failure detection sensor is attached to the through hole.

(2) Examples of Usage of the Failure Detection Sensor for Detecting Bend Fracture For example, in a road sign, two horizontal columns are attached parallel each other to a post stood vertically to a road with bolts and nuts, and a sign board is attached to those columns. In this case, these columns are cantilevers and there is a fear that bend fracture results due to deterioration depending on time caused by a long time use. Therefore, the risk of the bend fracture can be decided by attaching, for example, the failure detection sensor according to the fourth embodiment on the outer peripheral surface of these columns.

(3) Examples of Usage of the Failure Detection Sensor for Detecting Shear Fracture For example, in a steel tower, a framework is often constructed by joining many equilateral mountain type steels (especially, having a V-shape or L-shape cross section) with bolts and nuts. In this case, since a shear force is applied in these joints, there is a fear that shear fracture results due to deterioration depending on time caused by a long time use. Therefore, the risk of the shear fracture can be decided by attaching, for example, the failure detection sensor according to the first embodiment to the joints.

Furthermore, for example, in a pier of a bridge, a steel support is attached to the side of a concrete foundation installed on the ground and side plates of a steel support attached to the lower portion of the pier are joined with a side plate constituting the former support with bolts and nuts. In this case, since the shear force is applied to the joint, there is a fear that shear fracture results due to deterioration depending on time caused by a long time use. Therefore, the risk of the shear fracture can be detected by attaching, for example, the failure detection sensor according to the first embodiment to the joint.

Described now is a monitoring system which centrally monitors failure of a building using the failure detection sensors. As the failure detection sensors, for example, the failure detection sensor according to one of the first to the fifteenth embodiments can be used.

Figure 39:
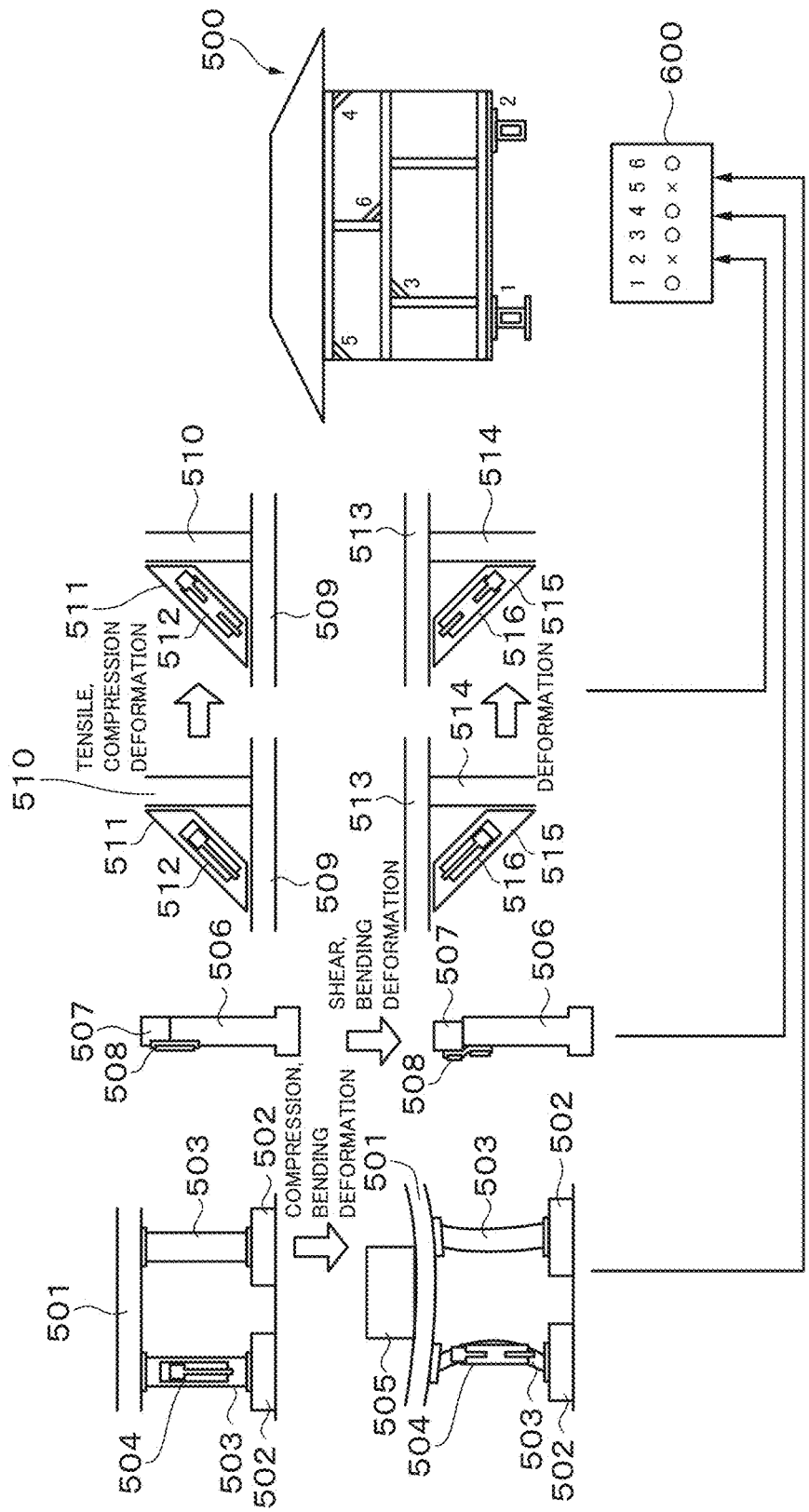
FIG. 39 A schematic view showing a watching system for watching a building using one of the failure detection sensors according to the first to the fifteenth embodiments of the invention.

FIG. 39 shows the monitoring system. As shown in the right side of FIG. 39, suppose now a building 500 built on the ground. As shown in the upper left of FIG. 39, a sleeper (horizontal materials supporting the floorboards) 501 of the building 500 is supported by floor posts (posts under the floor) 503 stood on footings of floor post (cornerstone) 502 fixed to the ground. The floor posts 503 are subject to compression and bend deformation. Therefore, a failure detection sensor 504 is attached to the side of the floor posts 503 such that the longitudinal direction of the failure detection sensor 503 coincides with the longitudinal direction of the floor posts 503. With this, as shown in the lower left of FIG. 39, the risk of the failure of the floor posts 503 when the sleeper 501 is given the weight of a weighty thing 505 can be decided by the failure detection sensor 504. As shown in the upper part of the second column from the left of FIG. 39, a base 507 is laid on the foundation 506 of the building 500. Between the foundation 506 and the base 507, a shear force and bending moment are given. Therefore, a failure detection sensor 508 is attached to the side of the foundation 506 and the base 507 such that the failure detection sensor 508 extends over the foundation 506 and the base 507 and its longitudinal direction coincides with the vertical direction. With this, as shown in the lower part of the second column from the left of FIG. 39, the risk of the shear fracture between the foundation 506 and the base 507 can be detected by the failure detection sensor 508. As shown in the upper part of the third column from the left of FIG. 39, a post 510 is vertically stood on a horizontal frame (or base) 509 of the building 500 and an inclined metal fittings for reinforcement 511 is attached between the horizontal frame 509 and the post 510. In this case, the metal fittings for reinforcement 511 is subject to tensile and compression deformation. Therefore, a failure detection sensor 512 is attached to the side of the metal fittings for reinforcement 511 such that its longitudinal direction coincides with the longitudinal direction of the metal fittings for reinforcement 511. With this, as shown in the upper part of the fourth column from the left of FIG. 39, the risk of the tensile fracture or the compression fracture of the metal fittings for reinforcement 511 can be detected by the failure detection sensor 512. As shown in the lower part of the third column from the left of FIG. 39, a beam 513 of the building 500 is supported by a vertical post 514 and an inclined metal fittings for reinforcement 515 is attached between the beam 513 and the post 514. In this case, the metal fittings 515 is subject to tensile and compression deformation. Therefore, a fracture detection sensor 516 is attached to the side of the metal fittings for reinforcement 515 such that its longitudinal direction coincides with the longitudinal direction of the metal fittings for reinforcement 515. With this, the risk of the tensile fracture or the compression fracture of the metal fittings for reinforcement 515 can be detected by the failure detection sensor 516.

Although not illustrated, each of the failure detection sensors 504, 508, 512, 516 has a device for detecting fracture of the second member as the same as the failure detection sensor according to the fourteenth embodiment. And a fracture signal detected by the device for detecting fracture of the second member of each of the failure detection sensors 504, 508, 512, 516 is transmitted to a monitoring system 600. With this, failure of each part of the building 500 can be centrally monitored by each of the failure detection sensors 504, 508, 512, 516. As an example, in the monitoring system 600, fracture signals by the failure detection sensors at parts shown by numbers 1~6 of the building 500 shown in the right side of FIG. 39 are shown by o, x. Here, o means that no fracture has occurred and x means that fracture has occurred.

Example

A failure detection sensor for detection of tensile fracture and a failure detection sensor for detection of bend fracture were made.

(1) The Failure Detection Sensor for Detection of Tensile Fracture

Figure 40:
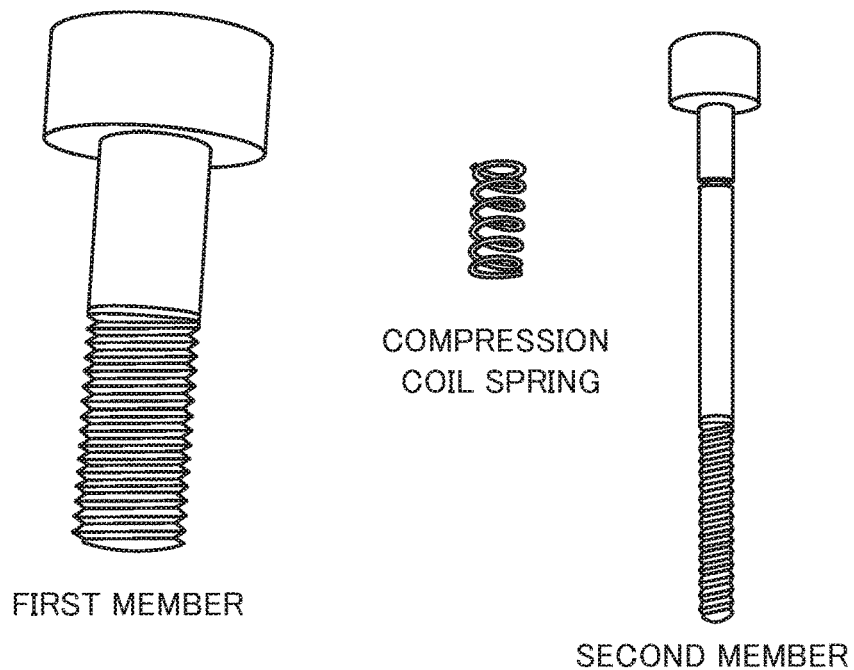
FIG. 40 A substitute picture for a drawing showing parts constituting a failure detection sensor for detecting tensile fracture made in an example.
Figure 41:
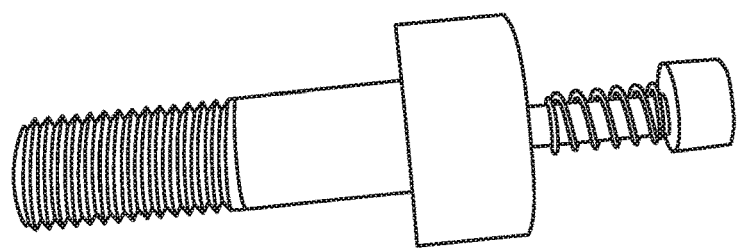
FIG. 41 A substitute picture for a drawing showing the failure detection sensor for detecting tensile fracture made in the example.

FIG. 40 shows a photograph of the first member, the second member and the compression coil spring constituting the failure detection sensor. FIG. 41 shows a photograph of the failure detection sensor assembled from these parts. Constitution of the failure detection sensor is the same as the first embodiment. Sizes of the first member are: L=90 mm, $L_1$=40 mm, $L_2$=65 mm, $L_3$=10 mm, $L_4$=15 mm, D=20 mm, $D_1$=6 mm, $D_2$=12 mm and $D_3$=16 mm. The head part of the first member has a diameter of 40 mm and a thickness of 20 mm. Sizes of the second member are: l=100 mm, $l_1$=85 mm, $l_2$=15 mm, $l_3$=30 mm, d=4 mm, θ=60° and the length from the front end of the second member to the notch is 70 mm. The first member is made of carbon steel for structural purposes and the second member is made of cast iron which is brittle materials.

Figure 42:
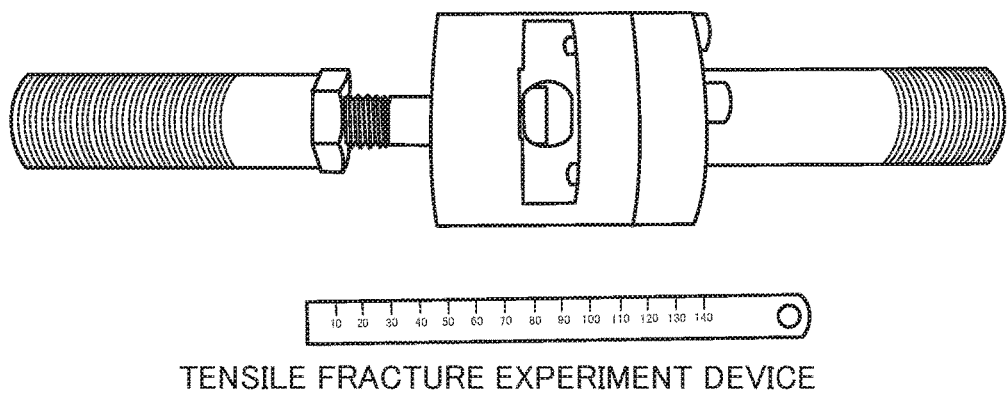
FIG. 42 A substitute picture for a drawing showing a tensile fracture experiment device using the failure detection sensor for detecting tensile fracture shown in FIG. 41.
Figure 43:
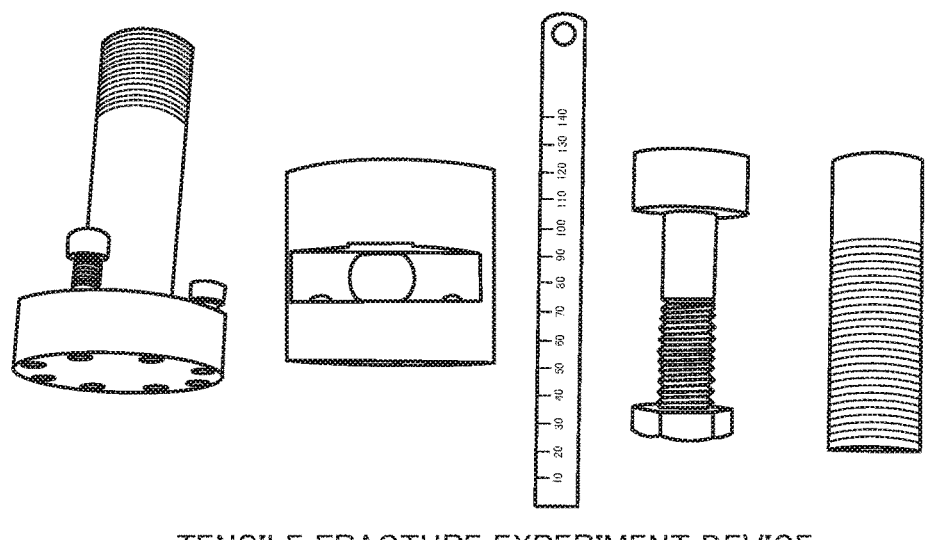
FIG. 43 A substitute picture for a drawing showing parts constituting the tensile fracture experiment device shown in FIG. 42.

FIG. 42 shows the tensile fracture experiment device used for experiment of tensile fracture. The tensile fracture experiment device pulls both ends of the first member in opposite directions each other and has a head part pull member including an engaging part of the head part, the first chuck member for joining with the head part pull member and chucking by the chuck part of the tensile test machine and the second chuck member to which the male screw of the axial part of the first member is fitted. FIG. 43 shows parts constituting the tensile fracture experiment device.

Figure 44:
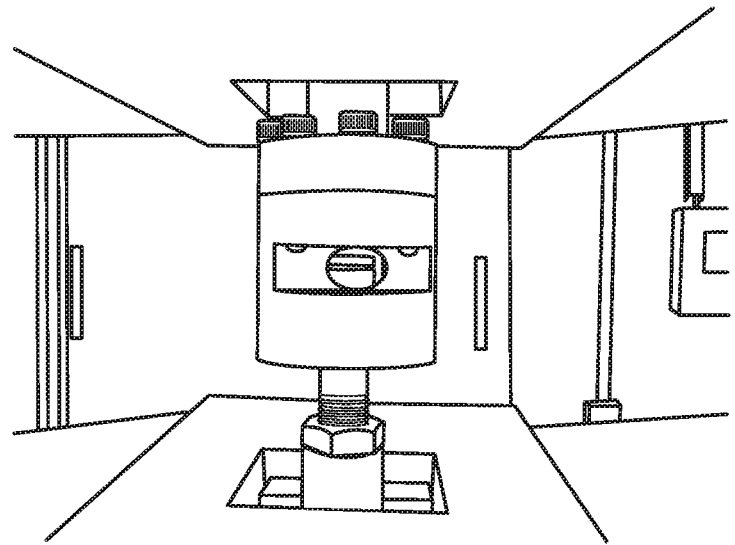
FIG. 44 A substitute picture for a drawing showing a state in which the tensile fracture experiment device shown in FIG. 42 is attached to a tensile test machine and a tensile test is carried out.
Figure 45:
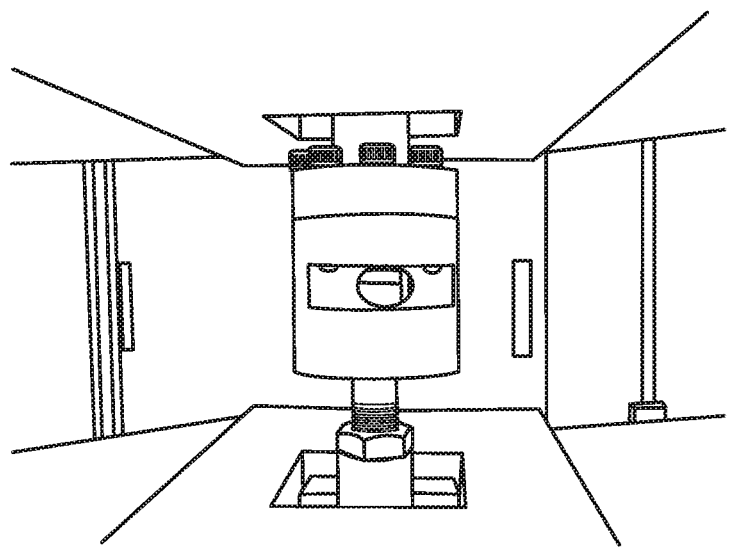
FIG. 45 A substitute picture for a drawing showing the state in which the tensile fracture experiment device shown in FIG. 42 is attached to the tensile test machine and the tensile test is carried out.
Figure 46:
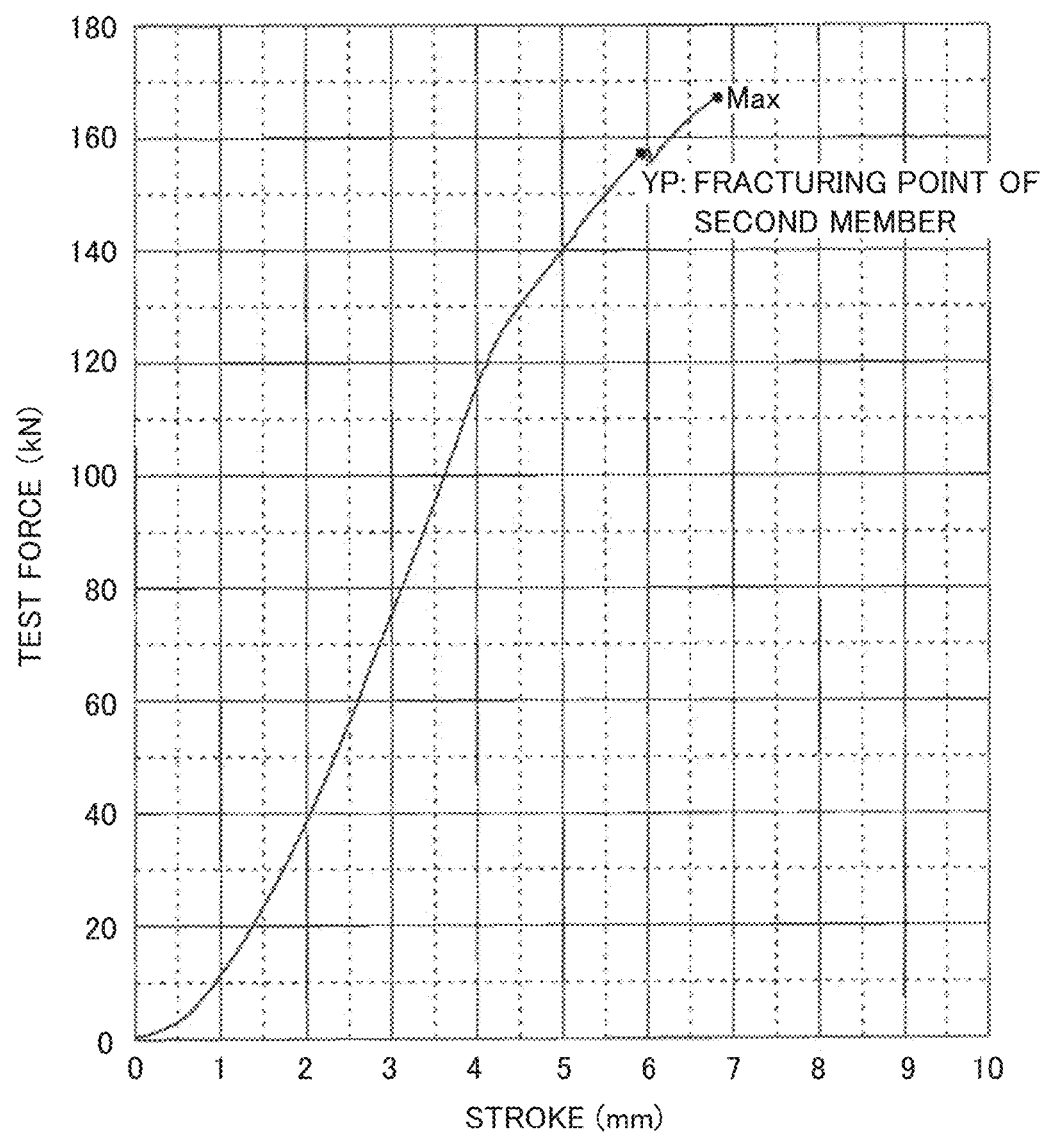
FIG. 46 A schematic view showing the result of the tensile test of the tensile fracture experiment device shown in FIG. 42.
Figure 47:
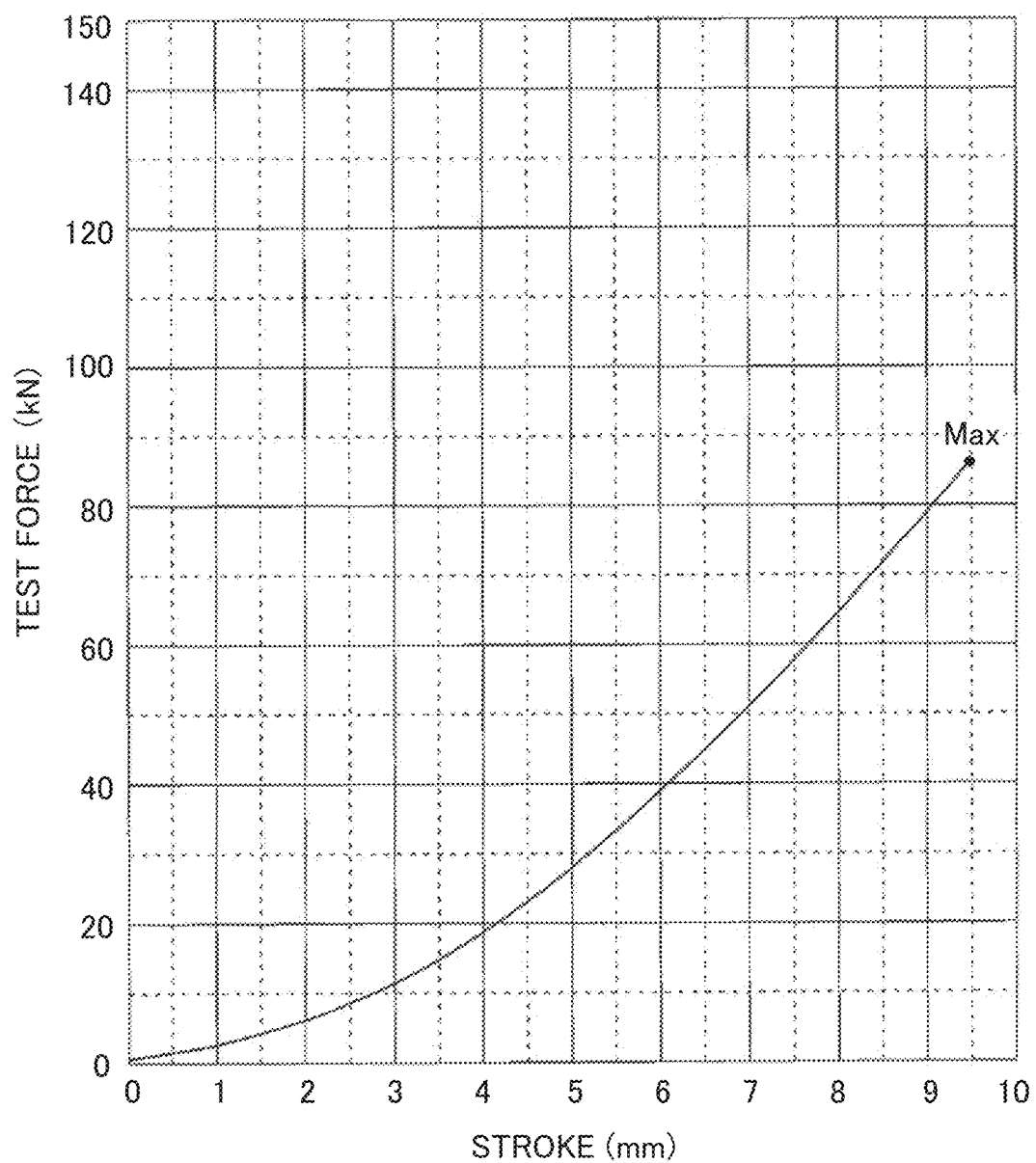
FIG. 47 A schematic view showing the result of the tensile test of the tensile fracture experiment device shown in FIG. 42.
Figure 48:
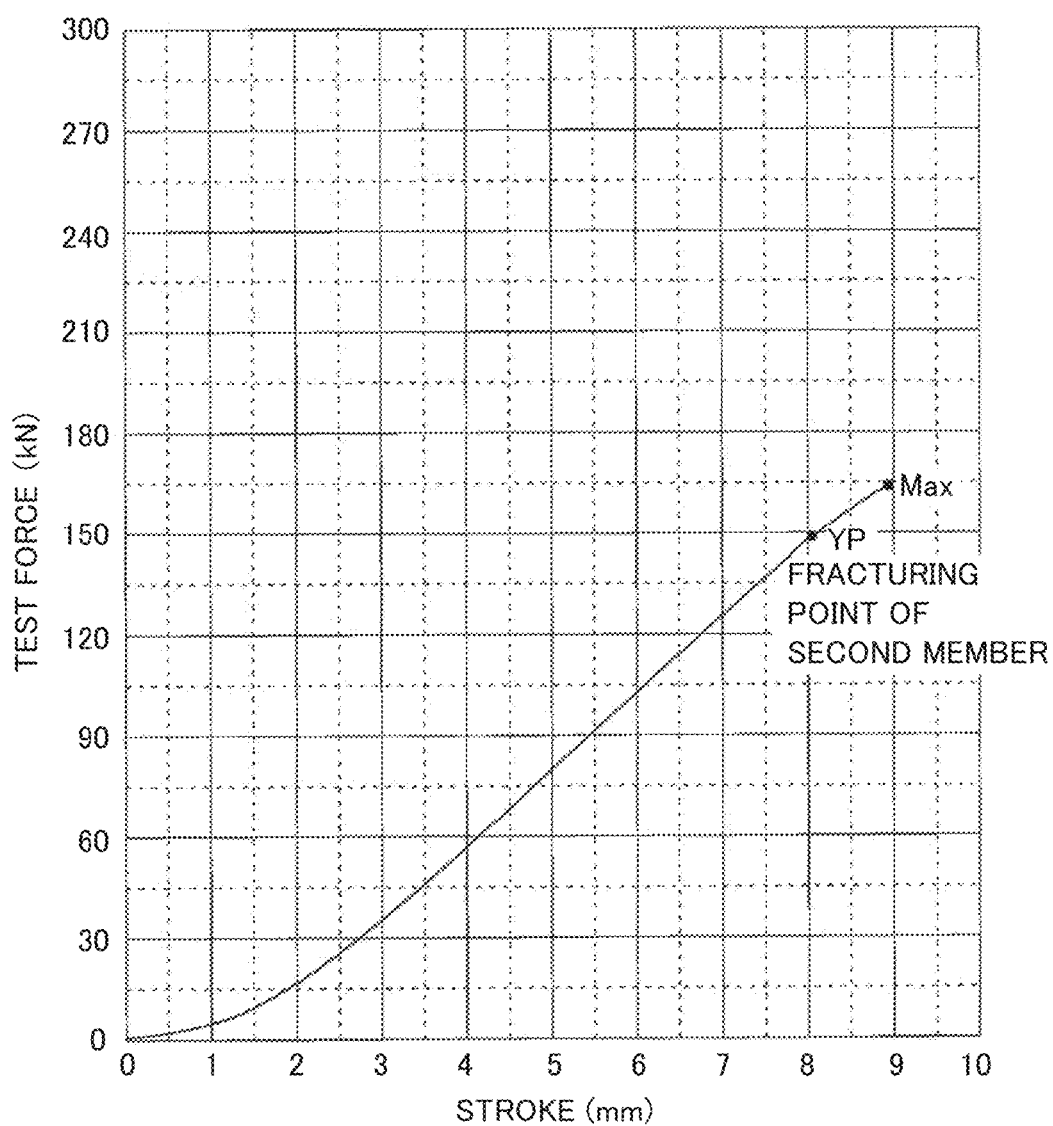
FIG. 48 A schematic view showing the result of the tensile test of the tensile fracture experiment device shown in FIG. 42.
Figure 49:
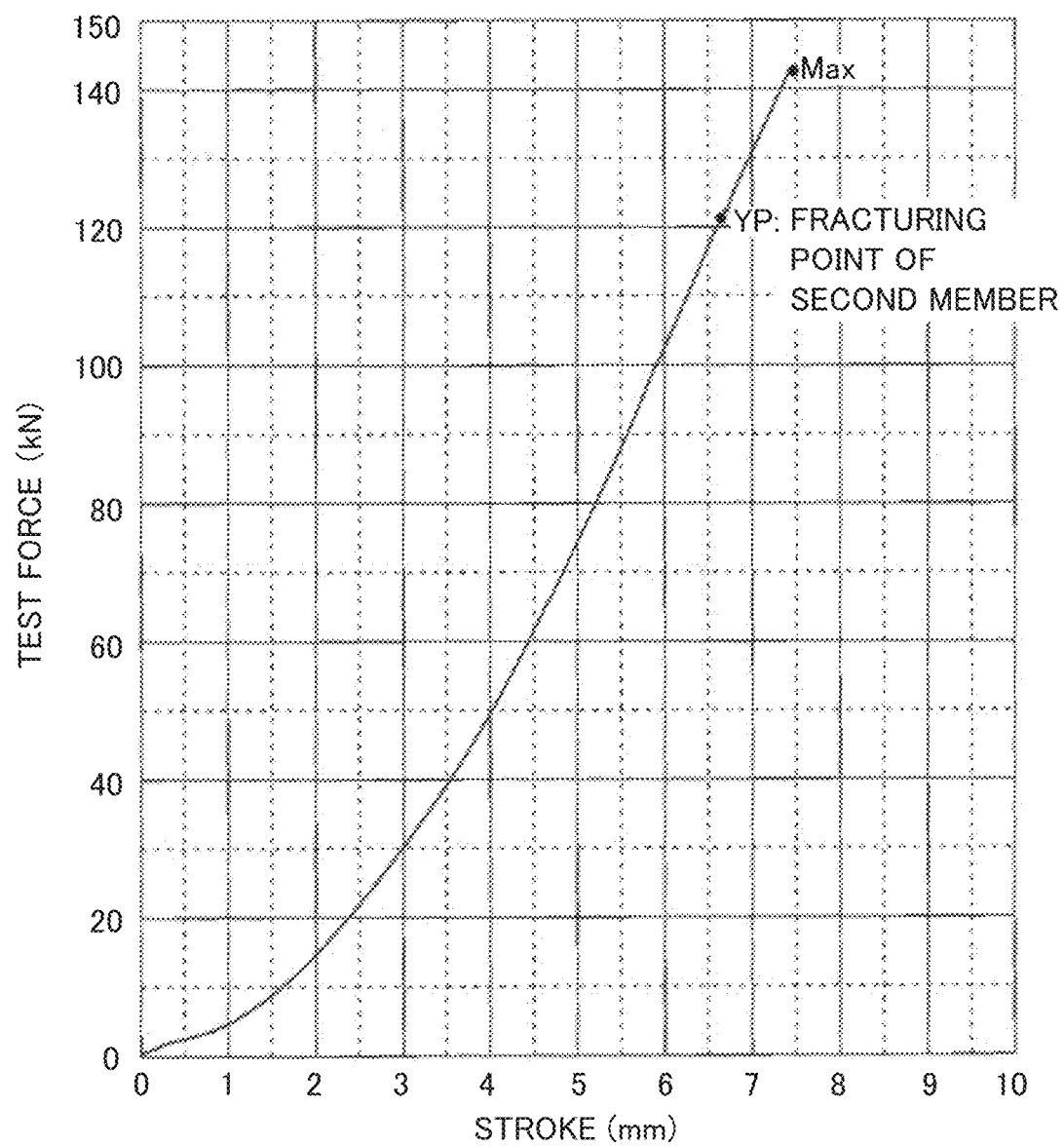
FIG. 49 A schematic view showing the result of the tensile test of the tensile fracture experiment device shown in FIG. 42.

FIG. 44 shows a state in which the tensile fracture experiment device was attached to the tensile test machine. FIG. 45 shows a state in which the tensile fracture experiment device was pulled by giving a tensile load of 150~160 kN. From FIG. 45, it is understood that the head part of the second member accommodated in the hollow part of the first member protruded outside the first member as a result of fracture of the second member.

FIG. 46~FIG. 49 show load-elongation curves when the tensile test of four failure detection sensors was carried out. The vertical axis of FIG. 46~FIG. 49 shows a test force (kN) which is a tensile load and the horizontal axis shows a stroke (mm) showing an elongation of the whole of the tensile fracture experiment device. In the load-elongation curves shown in FIG. 46, FIG. 48 and FIG. 49, an yield point (YP) appeared when the stroke reached about 6 mm and the second member fractured at the YP point. Thereafter the load reached the maximum load Max and the second member fractured. In the load-elongation curve shown in FIG. 47, the second member finally fractured, but the YP point was not observed.

(2) The Failure Detection Sensor for Detection of Bend Fracture

FIG. 50 is a photograph of the second member and the compression coil spring constituting the failure detection sensor and FIG. 51 is a photograph of the failure detection sensor assembled from these parts and the rectangular parallelepiped-like first member with the hollow part. Constitution of the failure detection sensor is the same as the eleventh embodiment. The first member is made of carbon steel for structural purposes and the second member is made of cast iron which is brittle materials.

Figure 52:
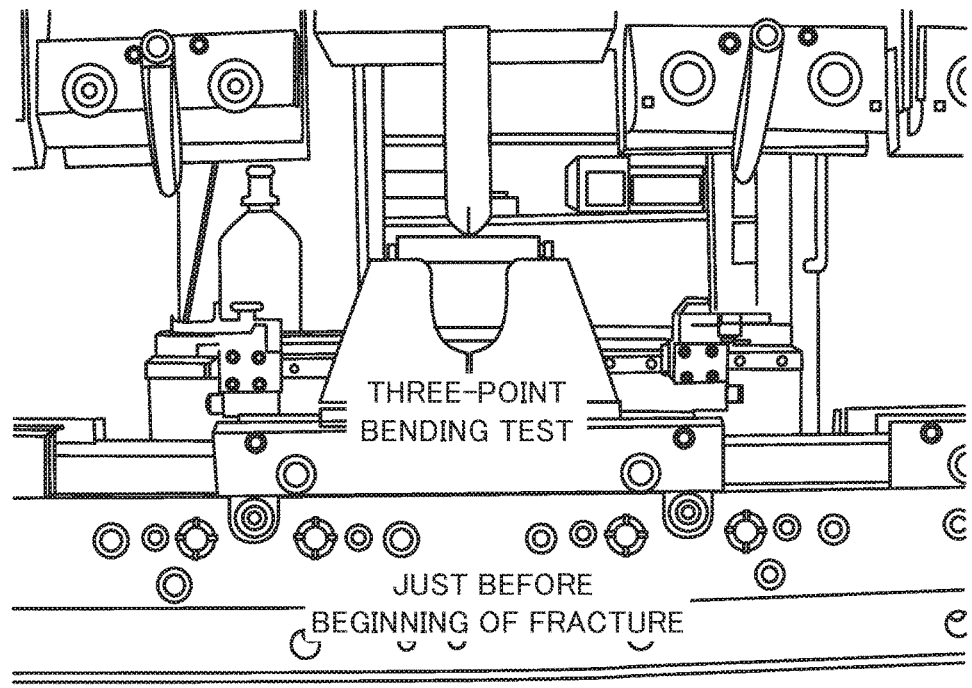
FIG. 52 A substitute picture for a drawing showing a state in which the failure detection sensor for detecting bend fracture shown in FIG. 51 is attached to a bending test machine and a three-point bending test is carried out.
Figure 53:
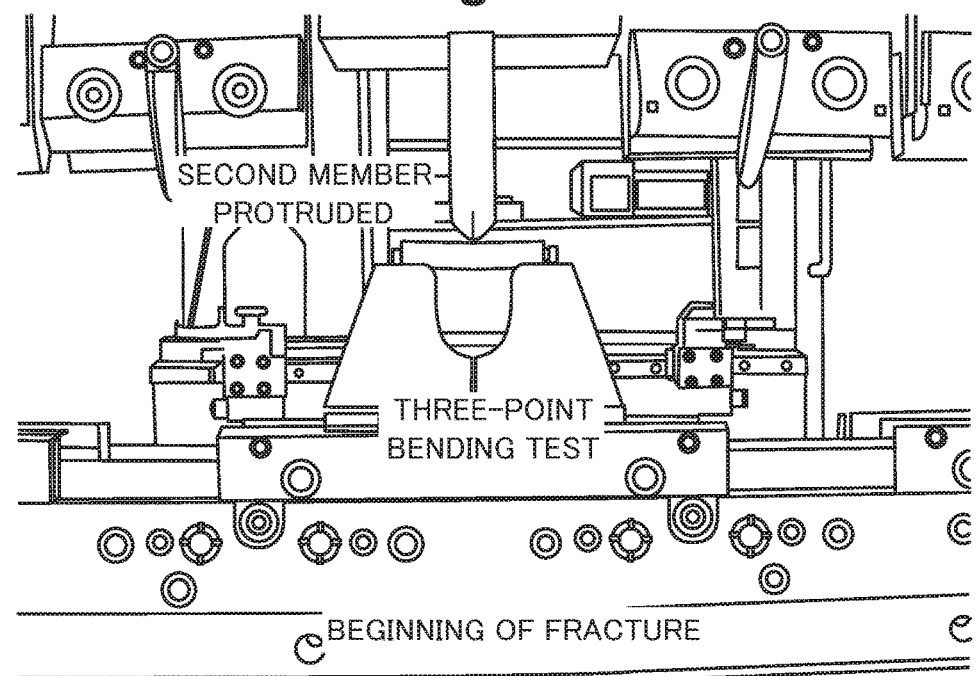
FIG. 53 A substitute picture for a drawing showing the state in which the failure detection sensor for detecting bend fracture shown in FIG. 51 is attached to the bending test machine and the three-point bending test is carried out.
Figure 54:
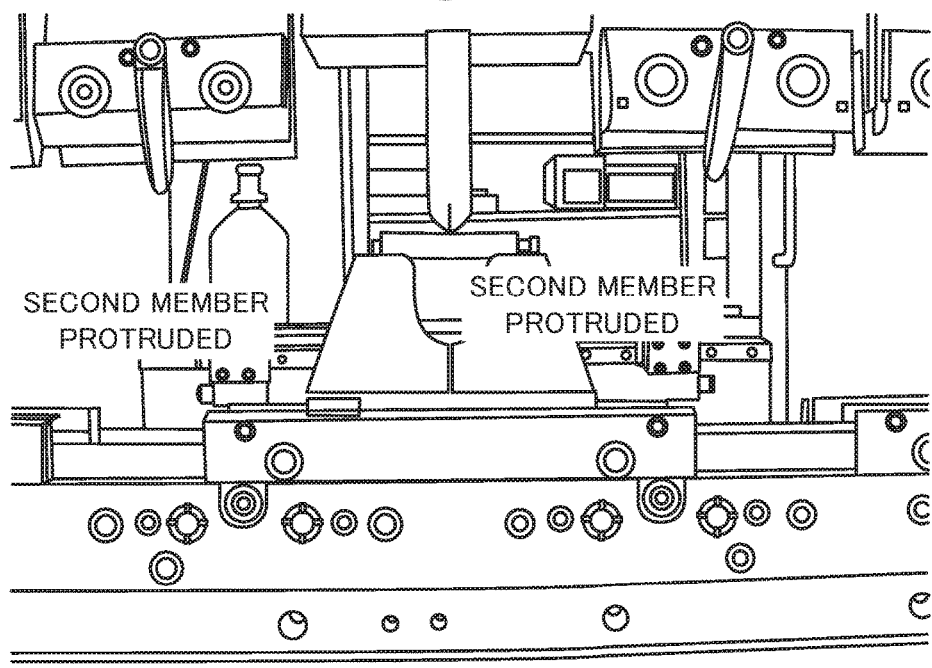
FIG. 54 A substitute picture for a drawing showing the state in which the failure detection sensor for detecting bend fracture shown in FIG. 51 is attached to the bending test machine and the three-point bending test is carried out.
Figure 55:
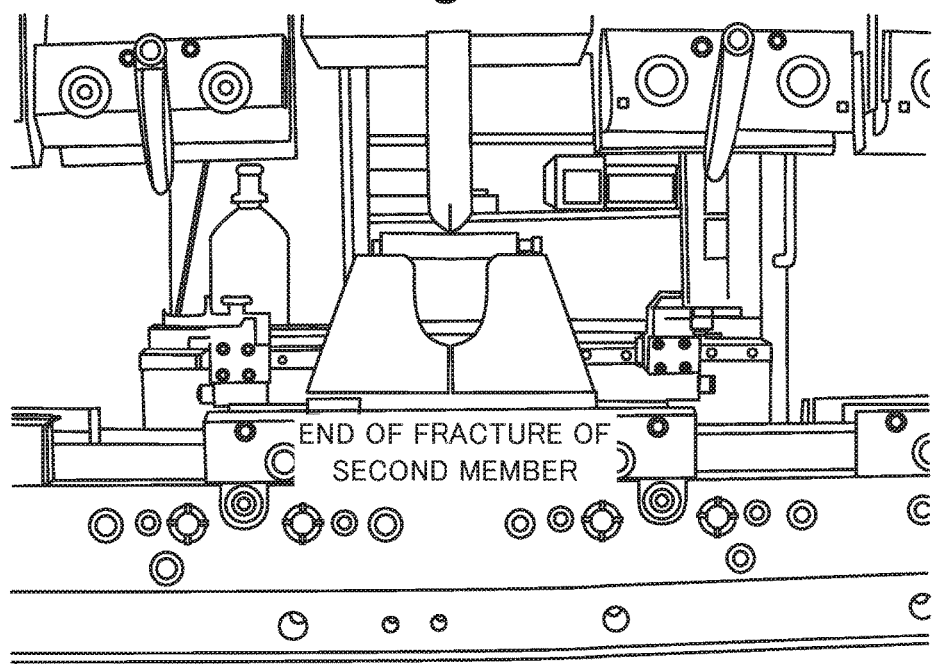
FIG. 55 A substitute picture for a drawing showing the state in which the failure detection sensor for detecting bend fracture shown in FIG. 51 is attached to the bending test machine and the three-point bending test is carried out.

As shown in FIG. 52, the failure detection sensor for detection of bend fracture was attached to the bending test machine and a downward load was given to the central part of the failure detection sensor for detection of bend fracture to bend. FIG. 52 shows a state just before fracture of the second member begins. FIG. 53 shows a state just after fracture of the second member begun. Since the second member begun to elongate, the head part of the second member accommodated in the hollow part of the first member begun to protrude outside the first member. At this time, the load was 45 kN (about 4.5 t). When bending was continued further, as shown in FIG. 54, the head part of the second member protruded from the first member. When bending was continued still further, as shown in FIG. 55, as a result of fracture of the second member, the head part of the second member accommodated in the hollow part of the first member protruded outside the first member.

(3) The Failure Detection Sensor for Detection of Tensile Fracture

Figure 56:
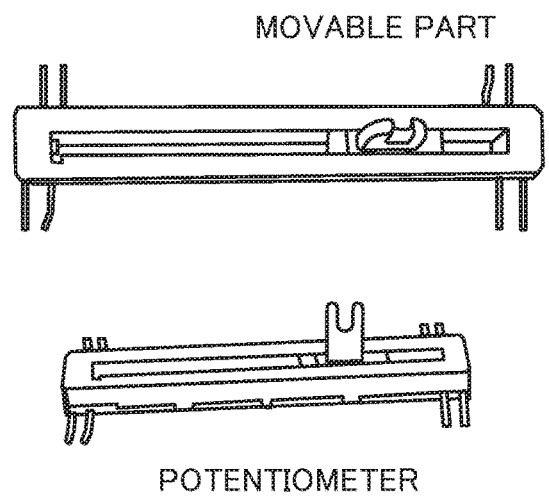
FIG. 56 A substitute picture for a drawing showing a potentiometer used as a failure detection sensor for measuring displacement using the potentiometer made in the example.
Figure 57:
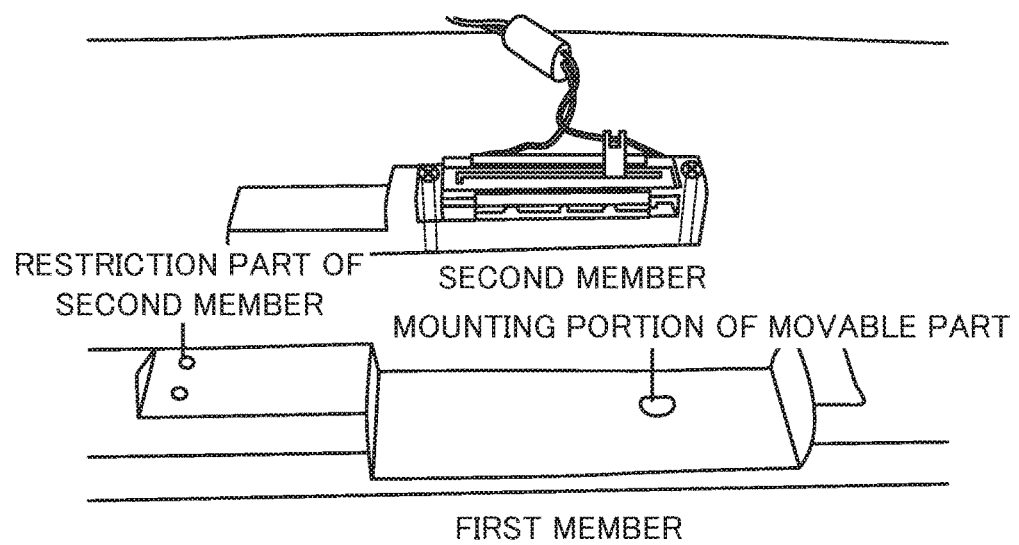
FIG. 57 A substitute picture for a drawing showing the failure detection sensor for measuring displacement using the potentiometer made in the example.
Figure 58:
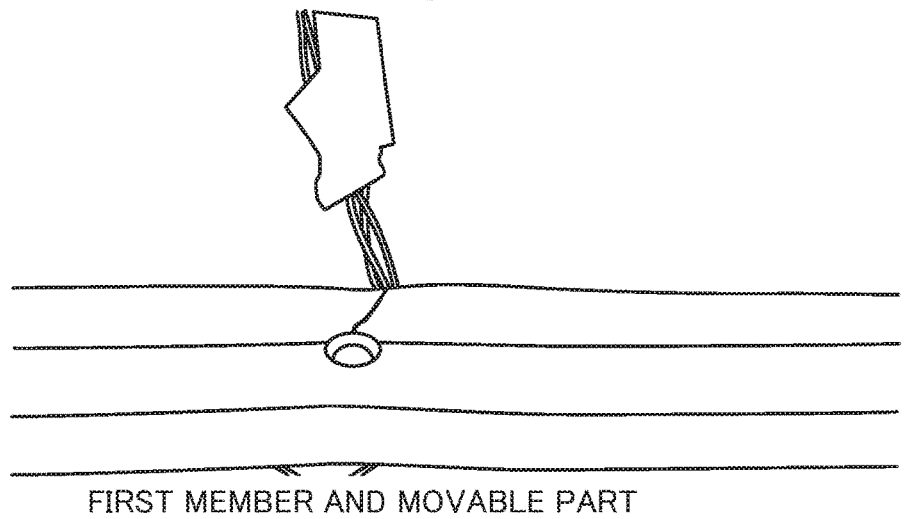
FIG. 58 A substitute picture for a drawing showing an enlarged view of a part of the failure detection sensor shown in FIG. 57.
Figure 59:
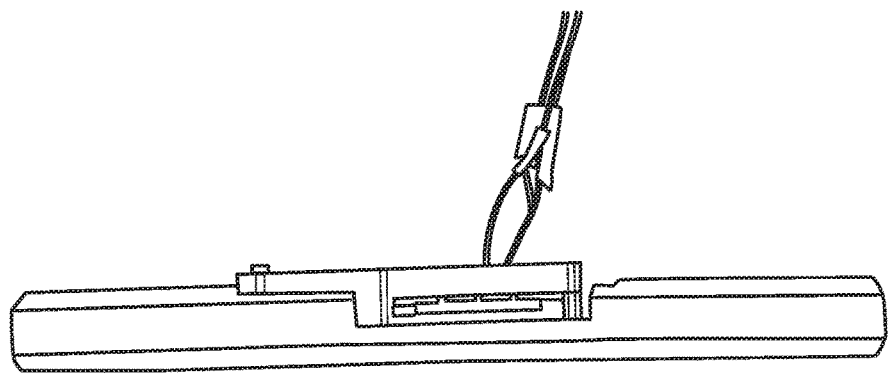
FIG. 59 A substitute picture for a drawing showing a displacement measurement piece of the failure detection sensor for measuring displacement using the potentiometer made in the example.
Figure 60:
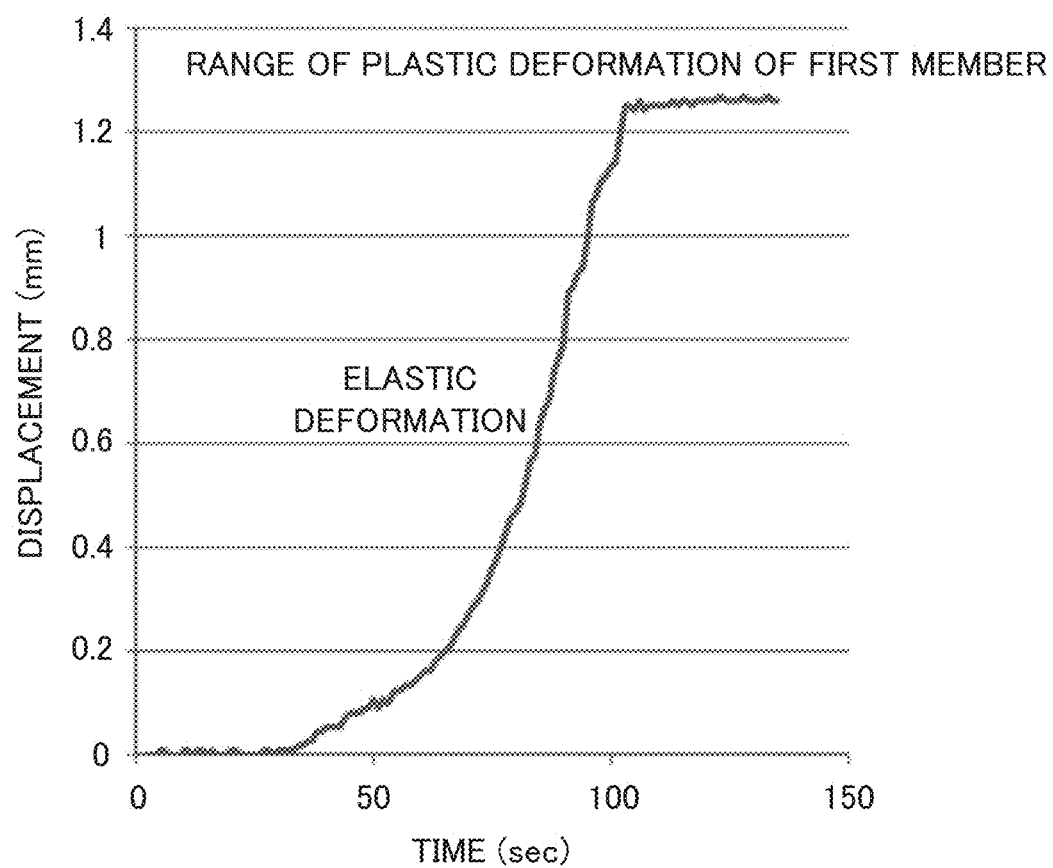
FIG. 60 A schematic view showing the result of measurement of displacement using the failure detection sensor shown in FIG. 57.

The failure detection sensor according to the fifteenth embodiment was made. FIG. 56 shows the potentiometer used. FIG. 57 shows parts constituting the failure detection sensor. FIG. 58 shows a state in which the movable part of the potentiometer accommodated inside the first member was fitted into the through hole formed in the first member and protruded outward. FIG. 59 shows a state in which the failure detection sensor was assembled. FIG. 60 shows the result of measurement of displacement during application of the tensile force to the first member. As shown in FIG. 60, it is understood that the first member produced elastic deformation for about 100 seconds after application of the tensile force and thereafter produced plastic deformation. When deformation begun by application of the tensile force to the first member, it was observed that the movable part of the potentiometer formed with the first member as one body moved with time. As described above, the displacement was obtained based on the equation ($L'_1$−$L'$) α=$R_1$−R from the resistance measured by the potentiometer.

Heretofore, embodiments and examples of the present invention have been explained specifically. However, the present invention is not limited to these embodiments and examples, but contemplates various changes and modifications based on the technical idea of the present invention.

For example, numerical numbers, shapes, structures, materials, etc. presented in the aforementioned embodiments and examples are only examples, and the different numerical numbers, shapes, structures, materials, etc. may be used as necessary.

Figure 61A:
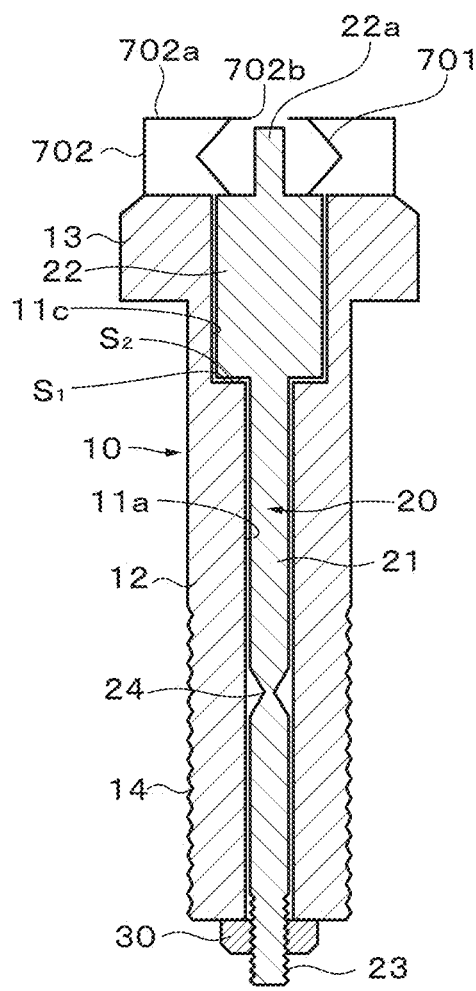
FIG. 61A A longitudinal view showing an example of the failure detection sensor in which a tensile force is applied to the second member using a leaf spring instead of a compression coil spring.
Figure 61B:
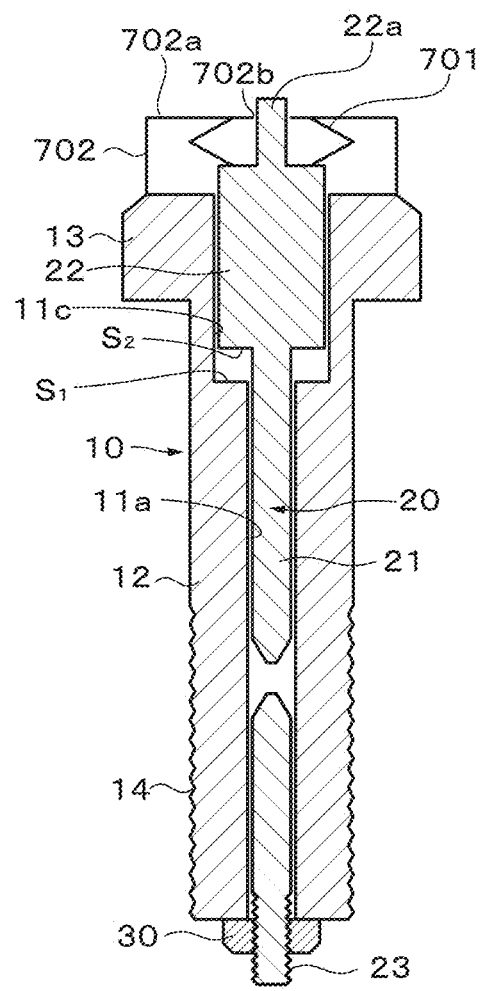
FIG. 61B A longitudinal view showing the example of the failure detection sensor in which a tensile force is applied to the second member using a leaf spring instead of a compression coil spring.

In the first to the fourteenth embodiments described above, the tensile force is applied to the head part 22 of the second member 20 by the compression coil spring 40 penetrated by the axial part 21 of the second member 20. However, in order to apply the tensile force to the head part 22 of the second member 20, for example, following methods may also be used. That is, as shown in FIG. 61A, the failure detection sensor is different from the failure detection sensor according to the first embodiment in that the hollow part 11 of the first member 10 is composed of only the first part 11a and the third part 11c and the compression coil spring 40 is not used. A spring holder 702 in which a leaf spring 701 is held is provided on the front end of the head part 13 of the bolt-like first member 10. The spring holder 702 is fixed to the head part 13 with sufficient strength by welding, gluing, screwing, etc. so that it does not peel off the head part 13 when the tensile force is applied by the leaf spring 701. In this example, the spring holder 702 is formed like a box. One end of the leaf spring 701 is fixed to the head part 22 of the second member 20 and the other end is fixed to the inner surface of the ceiling 702a of the spring holder 702. In this state, the leaf spring 701 is stretched as compared with its natural state. Therefore, the tensile force is applied to the head part 22 of the second member 20 by the leaf spring 701. As a result, the axial part 21 of the second member 20 is pulled on the side of the head part 22. With this, the front end part of the second member 20 is restricted to the front end part of the first member 10. The head part 22 of the second member 20 has a projection 22a with a small diameter on the front end. The projection 22a protrudes outside the third part 11c of the hollow part 11 of the first member 10 and locates inside the spring holder 702. Other constitution of the failure detection sensor is the same as the failure detection sensor according to the first embodiment. The method of using the failure detection sensor is as follows. As the same as the first embodiment, the failure detection sensor is inserted into the through hole 53 formed in the structural members 51, 52 and attached. As shown in FIG. 61B, when the second member 20 fractures at the notch 24 by elastic deformation or plastic deformation of the first member 10, the head part 22 of the fractured piece 70 is pulled to the outside (upward in FIG. 61B) by the tensile force by the leaf spring 701. A hole 702b is formed in the ceiling 702a of the spring holder 702 and the projection 22a of the head 22 protrudes from the hole 702b. It is easy to recognize visually from the outside, for example, that the projection 22a protrudes outside the spring holder 702. From the result, it is possible to decide that there is the risk of the failure since the structural members 51, 52 are given the tensile load. A coil spring may be used instead of the leaf spring 701. Furthermore, by making use of the fact that the projection 22a protrudes outside the spring holder 702, a fracture signal can be easily detected by electromagnetic induction. That is, for example, at least a part, for example, the front end part of the projection 22a is formed by permanent magnet made of ferromagnetic substance and a coil larger than the hole 702b is placed on the ceiling 702a of the spring holder 702 and above the projection 22a in parallel with the ceiling 702a. In this case, when the projection 22a protrudes outside the hole 702b by fracture of the second member 20, the projection 22a penetrates the coil and magnetic flux penetrating the coil increases. Therefore, a current (induced current) flows in the coil so as to prevent the magnetic flux from increasing. As a result, by detecting the induced current or induced electromotive force, fracture of the second member can be detected and a fracture signal can be easily obtained.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXPLANATION OF REFERENCE NUMERALS

10 The first member
11 Hollow part
20 The second member
24 Notch
40 Compression coil spring
51, 52 Structural member
70 Fractured piece
80 The first member
81 Hollow part
100 The third member
101 Hollow part
120 Compression coil spring
300 Device for detecting fracture of the second member
310 Fracturing state display device
320 Fracturing information transmitter
330 Receiving set

The invention claimed is:

1. A failure detection sensor, comprising:
a first member,
a second member provided in parallel with the first member such that one end of the second member is fixed to or restricted by the first member and the other end of the second member is not fixed to or restricted by the first member, having fracturing characteristics such that the second member fractures during elastic deformation or plastic deformation of the first member; and
an energizing mechanism for applying a tensile force to the other end of the second member on the opposite side of the one end.

2. The failure detection sensor according to claim 1, wherein the first member is constituted of a hollow rod and the second member is constituted of an inner rod which is inserted into the hollow part of the hollow rod.

3. The failure detection sensor according to claim 1, wherein the second member has a stress concentration site between the one end and the other end.

4. The failure detection sensor according to claim 1, wherein the second member is made of brittle materials.

5. The failure detection sensor according to claim 1, wherein the first member has a press part which presses the second member in the direction toward the other end from the one end when the first member produces elastic deformation or plastic deformation, and the second member has a part to be pressed by the press part.

* * * * *